US012683008B2

(12) United States Patent (10) Patent No.: US 12,683,008 B2
Lefkofsky et al. (45) Date of Patent: *Jul. 14, 2026

(54) DATA-BASED MENTAL DISORDER RESEARCH AND TREATMENT SYSTEMS AND METHODS

(71) Applicant: Tempus AI, Inc., Chicago, IL (US)

(72) Inventors: Hailey B. Lefkofsky, Chicago, IL (US); Christopher N. Vlangos, Chicago, IL (US)

(73) Assignee: Tempus AI, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/319,212

(22) Filed: May 17, 2023

(65) Prior Publication Data

US 2023/0386643 A1 Nov. 30, 2023

Related U.S. Application Data

(63) Continuation of application No. 17/207,972, filed on Mar. 22, 2021, now Pat. No. 11,682,481, which is a
(Continued)

(51) Int. Cl.
*G16H 20/70* (2018.01)
*G06Q 50/22* (2024.01)
(Continued)

(52) U.S. Cl.
CPC ............ *G16H 20/70* (2018.01); *G16B 20/00* (2019.02); *G16B 30/10* (2019.02); *G16H 10/60* (2018.01);
(Continued)

(58) Field of Classification Search
CPC ........ G16H 20/70; G16H 10/60; G16H 15/00; G16H 20/10; G16H 70/40; G16H 50/70; G16H 50/20; G16B 20/00; G16B 30/10
See application file for complete search history.

(56) References Cited

U.S. PATENT DOCUMENTS 8,401,801 B2 3/2013 Mrazek et al.
8,583,380 B2 11/2013 Stephan
(Continued)

FOREIGN PATENT DOCUMENTS

JP 2007525154 A 9/2007
JP 2018514026 A 5/2018
(Continued)

OTHER PUBLICATIONS

Ibeanu GC, et al. A novel transversion in the intron 5 donor splice junction of CYP2C19 and a sequence polymorphism in exon 3 contribute to the poor metabolizer phenotype for the anticonvulsant drug S-mephenytoin. J Pharmacol Exp Ther. Aug. 1999;290(2):635-40. PMID: 10411572.

(Continued)

*Primary Examiner* — Maroun P Kanaan
(74) *Attorney, Agent, or Firm* — Quarles & Brady LLP

(57) ABSTRACT

A system for personalized depression disorder treatment is disclosed herein. The system includes a server configured to communicate with existing healthcare resources and to receive patient data corresponding to a patient, the server including an analytics module. The system further includes a first database configured to store empirical patient outcomes, and further configured to communicate with the analytics module. Additionally, the system includes a user device having a graphical user interface (GUI) configured to communicate with the server and to display at least one output generated by the analytics module. The analytics module is configured to determine at least one of a personalized depression treatment and a personalized depression state prediction based on the empirical patient outcomes and the patient data.

19 Claims, 42 Drawing Sheets

Related U.S. Application Data continuation of application No. 16/984,072, filed on Aug. 3, 2020, now Pat. No. 10,978,196, which is a continuation-in-part of application No. PCT/US2019/056713, filed on Oct. 17, 2019.

(60) Provisional application No. 62/882,466, filed on Aug. 2, 2019, provisional application No. 62/746,997, filed on Oct. 17, 2018.

(51) Int. Cl.

| | |
|---|---|
| *G16B 20/00* | (2019.01) |
| *G16B 30/10* | (2019.01) |
| *G16H 10/60* | (2018.01) |
| *G16H 15/00* | (2018.01) |
| *G16H 20/10* | (2018.01) |
| *G16H 70/40* | (2018.01) |

(52) U.S. Cl.
CPC ............. *G16H 15/00* (2018.01); *G16H 20/10* (2018.01); *G16H 70/40* (2018.01)

(56) References Cited

U.S. PATENT DOCUMENTS

| | | | |
|---|---|---|---|
| 2007/0031853 A1 | 2/2007 | Stanton | |
| 2008/0118918 A1 | 5/2008 | Licinio | |
| 2009/0306534 A1 | 12/2009 | Pizzagalli | |
| 2011/0236917 A1 | 9/2011 | Goldknopf | |
| 2012/0208706 A1 | 8/2012 | Downing et al. | |
| 2013/0166320 A1* | 6/2013 | Kupershmidt | G16B 20/20 |
| | | | 705/3 |
| 2014/0370582 A1 | 12/2014 | Von Hoff | |
| 2016/0281171 A1 | 9/2016 | Miller | |
| 2018/0089373 A1 | 3/2018 | Matsuguchi et al. | |
| 2018/0095969 A1 | 4/2018 | Jung et al. | |
| 2019/0019573 A1 | 1/2019 | Lake et al. | |
| 2019/0088366 A1 | 3/2019 | Vaughan | |
| 2019/0367968 A1 | 12/2019 | Apte | |
| 2020/0123609 A1* | 4/2020 | Osborn | C12Q 1/6883 |
| 2020/0135303 A1 | 4/2020 | Barber | |
| 2020/0211716 A1 | 7/2020 | Lefkofsky | |

FOREIGN PATENT DOCUMENTS

| | | |
|---|---|---|
| WO | 2007121319 A2 | 10/2007 |
| WO | 2018209161 A1 | 11/2018 |

OTHER PUBLICATIONS

Ibeanu GC, et al. Identification of new human CYP2C19 alleles (CYP2C19*6 and CYP2C19*2B) in a Caucasian poor metabolizer of mephenytoin. J Pharmacol Exp Ther. Sep. 1998;286(3):1490-5. PMID: 9732415.

International Searching Authority. International Search Report and Written Opinion for application PCT/US2020/044795. Mailed on Dec. 1, 2020. 19 pages.

Italiano A, et al. SDHA loss of function mutations in a subset of young adult wild-type gastrointestinal stromal tumors. BMC Cancer. Sep. 14, 2012;12:408. doi: 10.1186/1471-2407-12-408. PMID: 22974104; PMCID: PMC3503624.

Jasperson KW, et al. APC-Associated Polyposis Conditions. Dec. 18, 1998 [updated Feb. 2, 2017]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301519.

Kim, Y., et al. "Molecular mechanisms of bipolar disorder: progress made and future challenges." Frontiers in cellular neuroscience 11 (2017): 30.

Larsen Haidle J, et al. Juvenile Polyposis Syndrome. May 13, 2003 [updated Mar. 9, 2017]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301642.

Lee SJ, et al. Identification of new CYP2C19 variants exhibiting decreased enzyme activity in the metabolism of S-mephenytoin and omeprazole. Drug Metab Dispos. Nov. 2009;37(11):2262-9. doi: 10.1124/dmd.109.028175. Epub Aug. 6, 2009. PMID: 19661214.

Legge, S. E., et al. "Association of genetic liability to psychotic experiences with neuropsychotic disorders and traits." JAMA psychiatry 76.12 (2019): 1256-1265.

Levey, D. F., et al. "Reproducible genetic risk loci for anxiety: results from~ 200,000 participants in the Million Veteran Program." American Journal of Psychiatry 177.3 (2020): 223-232.

Lichter-Konecki U, et al. Ornithine Transcarbamylase Deficiency. Aug. 29, 2013 [updated Apr. 14, 2016]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 24006547.

Lin KM, et al. CYP1A2 genetic polymorphisms are associated with treatment response to the antidepressant paroxetine. Pharmacogenomics. Nov. 2010; 11(11):1535-43. doi: 10.2217/pp. 10.128. PMID: 21121774.

Linehan WM. Evaluation and screening for hereditary renal cell cancers. Can Urol Assoc J. Sep.-Oct. 2013;7 (9-10):324-5. doi: 10.5489/cuaj.1685. PMID: 24319510; PMCID: PMC3854469.

Loeys BL, et al. Loeys-Dietz Syndrome. Feb. 28, 2008 [updated Mar. 1, 2018]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301312.

Lohmann DR, et al. Retinoblastoma. Jul. 18, 2000 [updated Nov. 2, 2018l]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301625.

Majewski IJ, et al. An a-E-catenin (CTNNA1) mutation in hereditary diffuse gastric cancer. J Pathol. Mar. 2013;229 (4):621-9. doi: 10.1002/path.4152. PMID: 23208944.

Marshe, V. S., et al. "Pharmacogenetic implications for antidepressant pharmacotherapy in late-life depression: a systematic review of the literature for response, pharmacokinetics and adverse drug reactions." The American Journal of Geriatric Psychiatry 28.6 (2020): 609-629.

Martin, A. R., et al. "Predicting polygenic risk of psychiatric disorders." Biological psychiatry 86.2 (2019): 97-109.

Mcgarrity TJ, et al. Peutz-Jeghers Syndrome. Feb. 23, 2001 [updated Jul. 14, 2016]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301443.

Mcnally E, et al. Arrhythmogenic Right Ventricular Cardiomyopathy. Apr. 18, 2005 [updated May 25, 2017]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301310.

Mehta, J., et al. "Use of Medical Transcription Data for Real World Clinicogenomic Evidence Generation for Mental Health Disorders in US." Poster PMH72. ISPOR 2018. Baltimore, MD.

Milewicz DM, et al. Heritable Thoracic Aortic Disease Overview. Feb. 13, 2003 [updated Dec. 14, 2017]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301299.

Morita J, et al. A novel single nucleotide polymorphism (SNP) of the CYP2C19 gene in a Japanese subject with lowered capacity of mephobarbital 4'-hydroxylation. Drug Metab Pharmacokinet. Jun. 2004;19(3):236-8. doi: 10.2133/dmpk.19.236. PMID: 15499191.

Nassan, M, et al. "Pharmacokinetic pharmacogenetic prescribing guidelines for antidepressants: a template for psychiatric precision medicine." Mayo Clinic Proceedings. vol. 91. No. 7. Elsevier, 2016.

Nielsen M, et al. MUTYH Polyposis. Oct. 4, 2012 [updated Oct. 10, 2019]. In: Adam MP, Ardinger HH, Pagon RA, Wallace SE, Bean

(56)        References Cited

OTHER PUBLICATIONS

LJH, Stephens K, Amemiya A, editors. GeneReviews [Internet]. Seattle (WA): University of Washington, Seattle; 1993-2020. PMID: 23035301.

NIMH Repository & Genomiocs Resource. PsychENCODE Consortium webpage. Accessed online at https://www.nimhgenetics.org/resources/psychencode on Sep. 14, 2020.

Noetzli L, et al. Germline mutations in ETV6 are associated with thrombocytopenia, red cell macrocytosis and predisposition to lymphoblastic leukemia. Nat Genet. May 2015;47(5):535-538. doi: 10.1038/ng.3253. Epub Mar. 25, 2015. PMID: 25807284; PMCID: PMC4631613.

Nofziger, C., et al. "PharmVar GeneFocus: CYP2D6." Clinical Pharmacology & Therapeutics 107.1 (2020): 154-170.

Northrup H, et al. Tuberous Sclerosis Complex. Jul. 13, 1999 [updated Apr. 16, 2020]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301399.

ONEOME. OneOme RightMed comprehensive test report overview. 2018.

ONEOME. Sample RightMed Test Report. Jun. 19, 2019. 14 pages.

Pantaleo MA, et al. SDHA loss-of-function mutations in KIT-PDGFRA wild-type gastrointestinal stromal tumors dentified by massively parallel sequencing. J Natl Cancer Inst. Jun. 22, 2011;103(12):983-7.

Papakostas, G. I., et al. "Efficacy of Esketamine Augmentation in Major Depressive Disorder: A Meta-Analysis." The Journal of Clinical Psychiatry 81.4 (2020):81(4):19r12889.

Perlis, R. H., et al. "Randomized, controlled, participant-and rater-blind trial of pharmacogenomic test-guided treatment versus treatment as usual for major depressive disorder." Depression and Anxiety (2020).

Petrucelli N, et al. BRCA1- and BRCA2-Associated Hereditary Breast and Ovarian Cancer. Sep. 4, 1998 [updated Dec. 15, 2016]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301425.

Power, R. A., et al. "Genome-wide association for major depression through age at onset stratification: major depressive disorder working group of the psychiatric genomics consortium." Biological Psychiatry 81.4 (2017): 325-335.

Pratt, V. M., et al. "Recommendations for clinical CYP2C19 genotyping allele selection: a report of the association for molecular pathology." The Journal of Molecular Diagnostics 20.3 (2018): 269-276.

PSYCH Congress Newsroom. Care Guided by Pharmacogenomic Testing May Benefit Patients With Possible Gene-Drug Interactions. Oct. 4, 2019. Accessed online at https://www.psychcongress.com/article/care-guided-pharmacogenomic-testing-may-benefit-patients-possible-gene-drug-interactions.

Quantigen Genomic Services. GeneDose Genetic Response Report for patient 2018B-MGL1-12. Nov. 7, 2018. 26 pages.

Quinn, B. MolDx Proposes Coverage for Pharmacogenetics Panel: A Win for AltheaDx. Sep. 12, 2018. Accessed online at http://www.discoveriesinhealthpolicy.com/2018/09/moldx-proposes-coverage-for.html.

Ramos P, et al. Small cell carcinoma of the ovary, hypercalcemic type, displays frequent inactivating germline and somatic mutations in SMARCA4. Nat Genet. May 2014;46(5):427-9.

Raygada M, et al. Counseling patients with succinate dehydrogenase subunit defects: genetics, preventive guidelines, and dealing with uncertainty. J Pediatr Endocrinol Metab. Sep. 2014;27(9-10):837-44. doi: 10.1515/jpem-2013-0369. PMID: 24854530; PMCID: PMC4718145.

Roehrig, C. "Mental disorders top the list of the most costly conditions in the United States: $201 billion." Health Affairs 35.6 (2016): 1130-1135.

Rosenberg H, et al. Malignant Hyperthermia Susceptibility. Dec. 19, 2003 [updated Jan. 16, 2020]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301325.

Rudberg I, et al. Impact of the ultrarapid CYP2C19*17 allele on serum concentration of escitalopram in psychiatric patients. Clin Pharmacol Ther. Feb. 2008;83(2):322-7. doi: 10.1038/sj.clpt.6100291. Epub Jul. 11, 2007. PMID: 17625515.

Rutledge, R. B., et al. "Machine learning and big data in psychiatry: toward clinical applications." Current opinion in neurobiology 55 (2019): 152-159.

Savage SA. Dyskeratosis Congenita. Nov. 12, 2009 [updated Nov. 21, 2019]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301779.

Schrode, N., et al. "Synergistic effects of common schizophrenia risk variants." Nature genetics 51.10 (2019): 1475.

Scott SA, et al. Identification of CYP2C19*4B: pharmacogenetic implications for drug metabolism including clopidogrel responsiveness. Pharmacogenomics J. Aug. 2012;12(4):297-305. doi: 10.1038/tpj.2011.5. Epub Mar. 1, 2011. PMID: 21358751; PMCID: PMC3310336.

Sellick GS, et al. Further evidence that germline CEBPA mutations cause dominant inheritance of acute myeloid leukaemia. Leukemia. Jul. 2005;19(7):1276-8. doi: 10.1038/sj.leu.2403788. PMID: 15902292.

Arloth, J. et al., Genetic Differences in the Immediate Transcriptome Response to Stress Predict Risk-Related Brain Function and Psychiatric Disorders, Neuron, 2015, 86:1189-1202.

European Patent Office, Extended Search Report, Application No. 20851017.2, Jan. 2, 2024, 13 pages.

Sibbing D, et al. Cytochrome 2019*17 allelic variant, platelet aggregation, bleeding events, and stent thrombosis in clopidogrel-treated patients with coronary stent placement. Circulation. Feb. 2, 2010;121(4):512-8. doi: 10.1161/CIRCULATIONAHA.109.885194. Epub Jan. 18, 2010. PMID: 20083681.

Silverman, E. PGx testing: recommended alleles for CYP2C19 panels. Cap Today. Aug. 2018. Accessed online at https://www.captodayonline.com/pgx-testing-recommended-alleles-cyp2c19-panels/.

Sim SC, et al. A common novel CYP2C19 gene variant causes ultrarapid drug metabolism relevant for the drug response to proton pump inhibitors and antidepressants. Clin Pharmacol Ther. Jan. 2006;79(1):103-13. doi: 10.1016/j.clpt.2005.10.002. PMID: 16413245.

Smith ML, et al. Mutation of CEBPA in familial acute myeloid leukemia. N Engl J Med. Dec. 2, 2004;351(23):2403-7. doi: 10.1056/NEJMoa041331. PMID: 15575056.

Solus JF, et al. Genetic variation in eleven phase I drug metabolism genes in an ethnically diverse population. Pharmacogenomics. Oct. 2004;5(7):895-931. doi: 10.1517/14622416.5.7.895. PMID: 15469410.

Soyama A, et al. Single nucleotide polymorphisms and haplotypes of CYP1A2 in a Japanese population. Drug Metab Pharmacokinet. Feb. 2005;20(1):24-33. doi: 10.2133/dmpk.20.24. Erratum in: Drug Metab Pharmacokinet. Apr. 2005;20 (2):152. PMID: 15770072.

Stratakis CA, et al. Carney Complex. Feb. 5, 2003 [updated Aug. 16, 2018]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301463.

Substance Abuse and Mental Health Services Administration. "Projections of national expenditures for treatment of mental and substance use disorders, 2010-2020." HHS Publication No. SMA-14-4883 (2014).

Tawana K, et al. Disease evolution and outcomes in familial AML with germline CEBPA mutations. Blood. Sep. 3, 2015;126(10):1214-23. doi: 10.1182/blood-2015-05-647172. Epub Jul. 10, 2015. PMID: 26162409.

Tervasmäki A, et al. Recurrent CYP2C19 deletion allele is associated with triple-negative breast cancer. BMC Cancer. Dec. 2, 2014;14:902. doi: 10.1186/1471-2407-14-902. PMID: 25466287; PMCID: PMC4265448.

Topka S, et al. Germline ETV6 Mutations Confer Susceptibility to Acute Lymphoblastic Leukemia and Thrombocytopenia. PLoS Genet.

(56) References Cited

OTHER PUBLICATIONS

Jun. 23, 2015;11(6):e1005262. doi: 10.1371/journal.pgen.1005262. PMID: 26102509; PMCID: PMC4477877.

Van Leeuwaarde RS, et al. Von Hippel-Lindau Syndrome. May 17, 2000 [updated Sep. 6, 2018]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301636.

Weiss KH. Wilson Disease. Oct. 22, 1999 [updated Jul. 29, 2016]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301685.

Wiley, F. "Proper Prescribing: Pharmacogenetics testing gains traction but requires a delicate balancing act." Published Oct. 7, 2019. Accessed online on Oct. 10, 2019 at url: https://www.clinicalomics.com/magazine-editions/volume-6-issue-number-5-september-october-2019/proper-prescribing-pharmacogenetics-testing-gains-traction-but-requires-a-delicate-balancing-act/.

Witkowski L, et al. Germline and somatic SMARCA4 mutations characterize small cell carcinoma of the ovary, hypercalcemic type. Nat Genet. May 2014;46(5):438-43. doi: 10.1038/ng.2931. Epub Mar. 23, 2014. PMID: 24658002.

Wray, N. R., et al. "Genome-wide association analyses identify 44 risk variants and refine the genetic architecture of major depression." Nature genetics 50.5 (2018): 668-681.

Wu, W. et al. "An electroencephalographic signature predicts antidepressant response in major depression." Nature biotechnology 38.4 (2020): 439-447.

Xu J, et al. HOXB13 is a susceptibility gene for prostate cancer: results from the International Consortium for Prostate Cancer Genetics (ICPCG). Hum Genet. Jan. 2013;132(1):5-14. doi: 10.1007/s00439-012-1229-4. Epub Oct. 12, 2012. PMID: 23064873; PMCID: PMC3535370.

Yi, Z., et al. "Blood-based gene expression profiles models for classification of subsyndromal symptomatic depression and major depressive disorder." PloS one 7.2 (2012): e31283.

Youngblom E, et al. Familial Hypercholesterolemia. Jan. 2, 2014 [updated Dec. 8, 2016]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 24404629.

Zhang MY, et al. Germline ETV6 mutations in familial thrombocytopenia and hematologic malignancy. Nat Genet. Feb. 2015; 47(2):180-5. doi: 10.1038/ng.3177. Epub Jan. 12, 2015. PMID: 25581430; PMCID: PMC4540357.

Zhou Q, et al. Genetic polymorphism, linkage disequilibrium, haplotype structure and novel allele analysis of CYP2C19 and CYP2D6 in Han Chinese. Pharmacogenomics J. Dec. 2009;9(6):380-94. doi: 10.1038/tpj.2009.31. Epub Jul. 28, 2009. PMID: 19636337.

ADMERA Health. Physician PGx Consultation Form. 2020.

AJMC. Exploring the Role of Genetics, Pharmacogenomic Testing in Psychiatric Disorders. Oct. 5, 2019. Accessed online at https://www.ajmc.com/view/exploring-the-role-of-genetics-pharmacogenomic-testing-in-psychiatric-disorders.

Aklillu E, et al. Genetic polymorphism of CYP1A2 in Ethiopians affecting induction and expression: characterization of novel haplotypes with single-nucleotide polymorphisms in intron 1. Mol Pharmacol. Sep. 2003;64(3):659-69. doi: 10.1124/mol.64.3.659. PMID: 12920202.

Alders, M., et al. Long QT Syndrome. Feb. 20, 2003 [Updated Feb. 8, 2018]. In: Adam MP, Ardinger HH, Pagon RA, et al., editors. GeneReviews [Internet]. Seattle (WA): University of Washington, Seattle; 1993-2020.

Altar, C. A., et al. "Clinical utility of combinatorial pharmacogenomics-guided antidepressant therapy: evidence from three clinical studies." Molecular neuropsychiatry 1.3 (2015): 145-155.

Amare, A. T., et al. "Pharmacogenomics in the treatment of mood disorders: strategies and opportunities for personalized psychiatry." EPMA Journal 8.3 (2017): 211-227.

Arber DA, et al. The 2016 revision to the World Health Organization classification of myeloid neoplasms and acute eukemia. Blood. May 19, 2016;127(20):2391-405. doi: 10.1182/blood-2016-03-643544. Epub Apr. 11, 2016. PMID: 27069254.

Assurex Health. Sample GeneSight Psychotropic Combinatorial Pharmacogenomic Test. 2017. 9 pages.

Benitez, J., et al. "Use of combinatorial pharmacogenomic guidance in treating psychiatric disorders." Personalized Medicine 15.6 (2018): 481-494.

Border, R., et al. "No. support for historical candidate gene or candidate gene-by-interaction hypotheses for major depression across multiple large samples." American Journal of Psychiatry 176.5 (2019): 376-387.

Bousman, C. A., et al. "Antidepressant prescribing in the precision medicine era: a prescriber's primer on pharmacogenetic tools." BMC psychiatry 17.1 (2017): 1-7.

Bradley, P., et al. "Improved efficacy with targeted pharmacogenetic-guided treatment of patients with depression and anxiety: a randomized clinical trial demonstrating clinical utility." Journal of psychiatric research 96 (2018): 100-107.

Byers PH. Vascular Ehlers-Danlos Syndrome. Sep. 2, 1999 [updated Feb. 21, 2019]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301667.

Cai Q, et al. Germline HOXB13 p.Gly84Glu mutation and cancer susceptibility: a pooled analysis of 25 epidemiological studies with 145,257 participates. Oncotarget. Dec. 8, 2015;6(39):42312-21. doi: 10.18632/oncotarget.5994. PMID: 26517352; PMCID: PMC4747227.

Centers for Medicare & Medicaid Services. Local Coverage Determination (LCD): MolDX: Pharmacogenomics Testing (L38294). Version dated Jun. 5, 2020. Accessed online at https://www.cms.gov/medicare-coverage-database/details/lcd-details.aspx?LCDId= 38294&ver=16&name=391*1&UpdatePeriod=889&bc= AAAACAAAAAAA&[cms.gov].

Chekroud, A. M., et al. "Cross-trial prediction of treatment outcome in depression: a machine learning approach." The Lancet Psychiatry 3.3 (2016): 243-250.

Chen, J., et al. "Association of a Reproducible Epigenetic Risk Profile for Schizophrenia With Brain Methylation and Function." JAMA psychiatry (2020).

Chua EW, et al. Novel CYP2D6 and CYP2C19 variants identified in a patient with adverse reactions towards venlafaxine monotherapy and dual therapy with nortriptyline and fluoxetine. Pharmacogenet Genomics. Sep. 2013;23 (9):494-7. doi: 10.1097/FPC. 0b013e328363688d. PMID: 23799451.

Cirino AL, et al. Hypertrophic Cardiomyopathy Overview. Aug. 5, 2008 [updated Jun. 6, 2019]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301725.

De Morais SM, et al. The major genetic defect responsible for the polymorphism of S-mephenytoin metabolism in humans. J Biol Chem. Jun. 3, 1994;269(22):15419-22. PMID: 8195181.

Dietz H. Marfan Syndrome. Apr. 18, 2001 [updated Oct. 12, 2017]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301510.

Dome JS, et al. Wilms Tumor Predisposition. Dec. 19, 2003 [updated Oct. 20, 2016]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301471.

Drogemoller BI, et al. Characterization of the genetic profile of CYP2C19 in two South African populations. Pharmacogenomics. Aug. 2010;11(8):1095-103. doi: 10.2217/pp. 10.90. PMID: 20712527.

Dwight T, et al. Loss of SDHA expression identifies SDHA mutations in succinate dehydrogenase-deficient gastrointestinal stromal tumors. Am J Surg Pathol. Feb. 2013;37(2):226-33. doi: 10.1097/PAS.0b013e3182671155. PMID: 23060355.

Eckerle M. D, et al. Familial Atypical Multiple Mole Melanoma Syndrome. In: Riegert-Johnson DL, Boardman LA, Hefferon T, Roberts M, editors. Cancer Syndromes [Internet]. Bethesda (MD): National Center for Biotechnology Information (US); 2009-. PMID: 21249757.

(56) References Cited

OTHER PUBLICATIONS

Else T, et al. Hereditary Paraganglioma-Pheochromocytoma Syndromes. May 21, 2008 [updated Oct. 4, 2018]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301715.

Eng C. Multiple Endocrine Neoplasia Type 2. Sep. 27, 1999 [updated Aug. 15, 2019]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301434.

Evans DG, et al. Nevoid Basal Cell Carcinoma Syndrome. Jun. 20, 2002 [updated Mar. 29, 2018]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301330.

Evans DG. Neurofibromatosis 2. Oct. 14, 1998 [updated Mar. 15, 2018]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301380.

Ewing CM, et al. Germline mutations in HOXB13 and prostate-cancer risk. N Engl J Med. Jan. 12, 2012;366(2):141-9. doi: 10.1056/NEJMoa1110000. PMID: 22236224; PMCID: PMC3779870.

Fabbri, C., et al. "The genetics of treatment-resistant depression: a critical review and future perspectives." International Journal of Neuropsychopharmacology 22.2 (2019): 93-104.

Fang, Y., et al. "Genomic Prediction of Depression Risk and Resilience Under Stress." bioRxiv (2019): 599456.

Fernandes, B. S., et al. "The new field of 'precision psychiatry'." BMC medicine 15.1 (2017): 1-7.

Fried, E. I., et al. "Depression is not a consistent syndrome: an investigation of unique symptom patterns in the Star* D study." Journal of affective disorders 172 (2015): 96-102.

Fukushima-Uesaka H, et al. Genetic variations and haplotypes of CYP2C19 in a Japanese population. Drug Metab Pharmacokinet. Aug. 2005;20(4):300-7. doi: 10.2133/dmpk.20.300. PMID: 16141610.

GENESIGHT Webpage. Marketing Excerpts. GeneSight.com. 2020.

GENOMIND. Genecept Assay Brochure. Nov. 2018. 1 page.

GENOMIND. Genomind Content. 2020.

GENOMIND. Genomind Professional PGx Express Webpage. Sep. 3, 2019. 3 pages.

GENOMIND. GENOMIND Professional PGx Expresstm Analyzes Two Types of Genes to Inform Treatment. Sep. 2019. 1 page.

Giusti F, et al. Multiple Endocrine Neoplasia Type 1. Aug. 31, 2005 [updated Dec. 14, 2017]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301710.

Golov, A. K., et al. "Novel Approaches for Identifying the Molecular Background of Schizophrenia." Cells 9.1 (2020): 246.

Greden, J. F., et al. "Impact of pharmacogenomics on clinical outcomes in major depressive disorder in the GUIDED trial: a large, patient-and rater-blinded, randomized, controlled study." Journal of psychiatric research 111 (2019): 59-67.

Hall-Flavin, D. K., et al. "Using a pharmacogenomic algorithm to guide the treatment of depression." Translational psychiatry 2.10 (2012): e172-e172.

Hansford S, et al. Hereditary Diffuse Gastric Cancer Syndrome: CDH1 Mutations and Beyond. JAMA Oncol. Apr. 2015; 1(1):23-32. doi: 10.1001/jamaoncol.2014.168. Erratum in: JAMA Oncol. Apr. 2015; 1(1):110. PMID: 26182300.

Hayashi Y, et al. Myeloid neoplasms with germ line RUNX1 mutation. Int J Hematol. Aug. 2017; 106(2):183-188. doi: 10.1007/s12185-017-2258-5. Epub May 22, 2017. PMID: 28534116.

He, Y. et al. "Copy number variants in pharmacogenetic genes." Trends in molecular medicine 17.5 (2011): 244-251.

Hoehe, M. R., et al. "The role of genetics and genomics in clinical psychiatry." Dialogues in clinical neuroscience 20.3 (2018): 169.

Hu LM, et al. Genetic polymorphisms and novel allelic variants of CYP2C19 in the Chinese Han population. Pharmacogenomics. Nov. 2012;13(14):1571-81. doi: 10.2217/pp. 12.141. PMID: 23148634.

Hyde SM, et al. CDC73-Related Disorders. Dec. 31, 2008 [updated Apr. 26, 2018]. In: Adam MP, Ardinger HH, Pagon RA, Wallace SE, Bean LJH, Stephens K, Amemiya A, editors. GeneReviews [Internet]. Seattle (WA): University of Washington, Seattle; 1993-2020. PMID: 20301744.

Australian Patent Office Examination Report No. 3 dated Feb. 20, 2026 for AU 2020326626, 5 pages.

* cited by examiner

"T" EMPUS

Welcome, David Patel ∨

My Patients — 52

Search — 54

| PATIENT NAME | PHYSICIAN | REPORT TYPE | REPORT DATE | STATUS |
|---|---|---|---|---|
| Dwayne Holder | David Patel | Risk Assessment | 06/25/17 | In Progress |
| Barbara Jensen | David Patel | Diagnostic | 06/25/17 | ⊘ Delivered |
| Arnold Lawrence | David Patel | Diagnostic | 06/25/17 | ⊘ Delivered |
| Terry Wood | David Patel | Diagnostic | 06/06/17 | ⊘ Delivered |
| Jonathan Andrews | Maria Stone | Risk Assessment | 06/06/17 | ⊘ Delivered |
| Mary Beth Anderson | Maria Stone | Risk Assessment | 06/06/17 | ⊘ Delivered |
| George Warren | Maria Stone | Diagnostic | 06/06/17 | ⊘ Delivered |

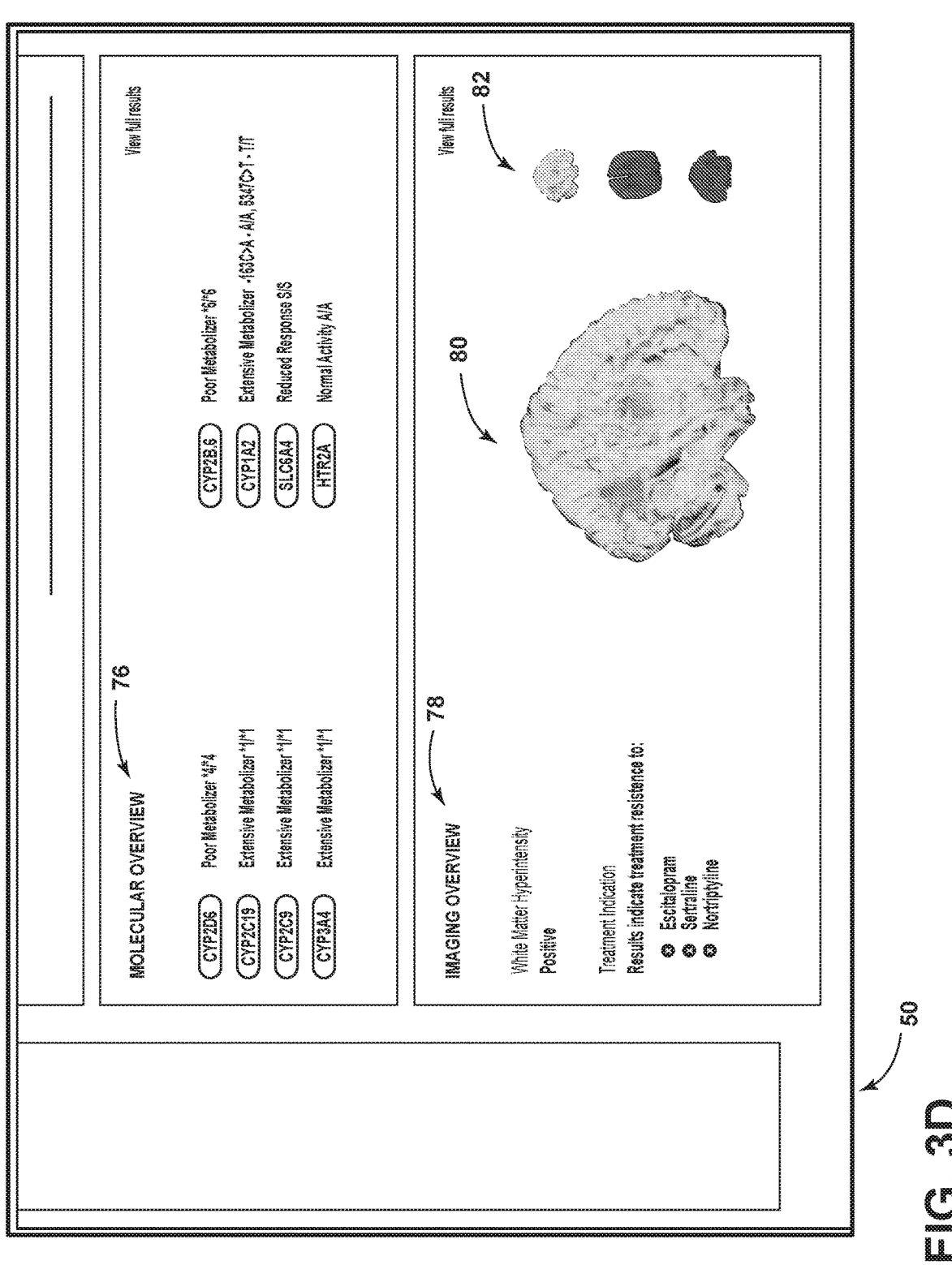

MOLECULAR OVERVIEW  76

| CYP2D6 | Poor Metabolizer *4/*4 |
| CYP2C19 | Extensive Metabolizer *1/*1 |
| CYP2C9 | Extensive Metabolizer *1/*1 |
| CYP3A4 | Extensive Metabolizer *1/*1 |

| CYP2B6 | Poor Metabolizer *6/*6 |
| CYP1A2 | Extensive Metabolizer -163C>A - A/A, 534*C>T - T/T |
| SLC6A4 | Reduced Response S/S |
| HTR2A | Normal Activity A/A |

View full results

IMAGING OVERVIEW  78

White Matter Hyperintensity
Positive

Treatment Indication
Results indicate treatment resistence to:
- Escitalopram
- Sertraline
- Nortriptyline

80

82

View full results

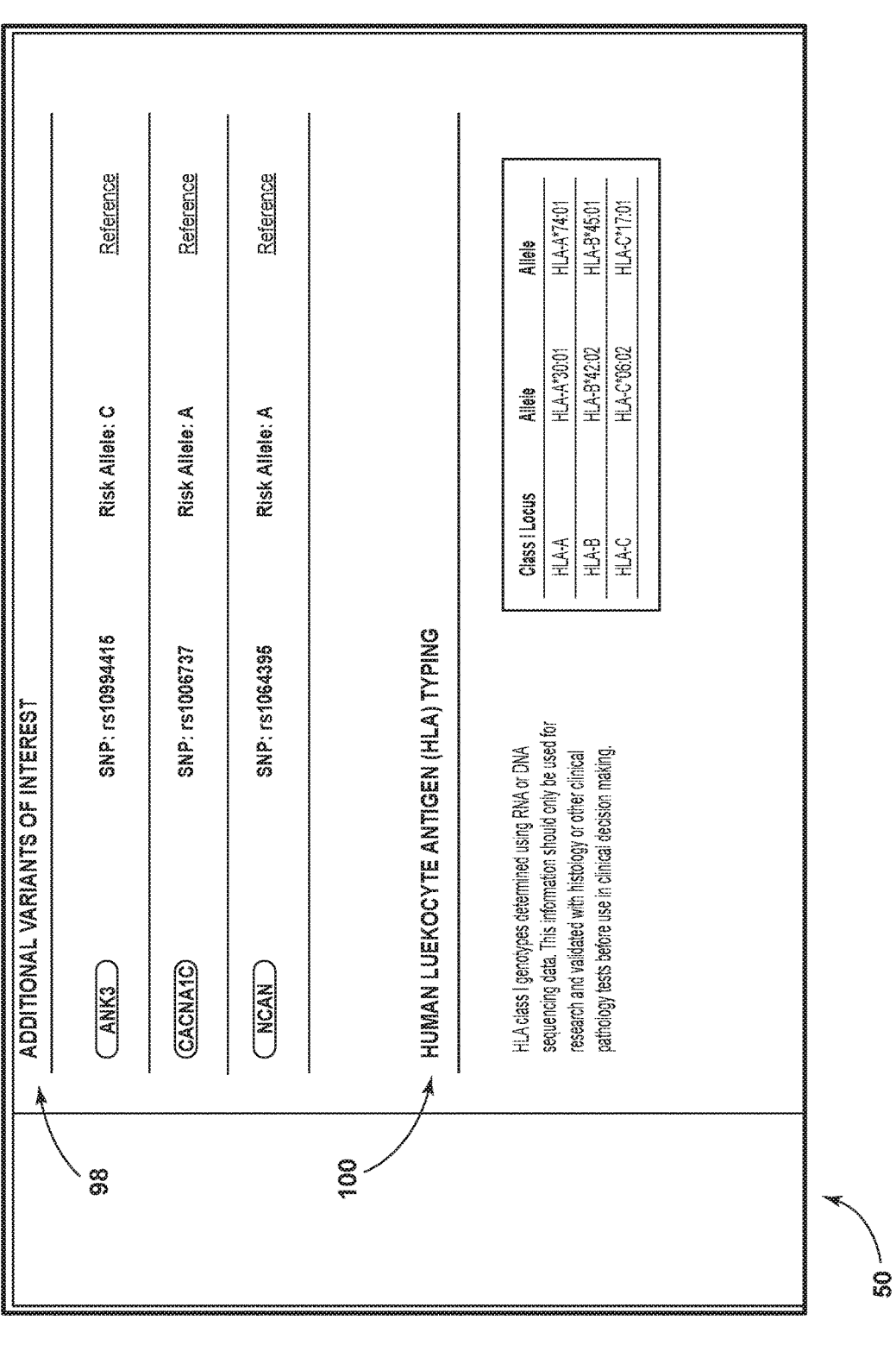

ADDITIONAL VARIANTS OF INTEREST

ANK3     SNP: rs10994415     Risk Allele: C     Reference

CACNA1C     SNP: rs1006737     Risk Allele: A     Reference

NCAN     SNP: rs1064395     Risk Allele: A     Reference

HUMAN LUEKOCYTE ANTIGEN (HLA) TYPING

HLA class I genotypes determined using RNA or DNA sequencing data. This information should only be used for research and validated with histology or other clinical pathology tests before use in clinical decision making.

| Class I Locus | Allele | Allele |
|---|---|---|
| HLA-A | HLA-A*30:01 | HLA-A*74:01 |
| HLA-B | HLA-B*42:02 | HLA-B*45:01 |
| HLA-C | HLA-C*06:02 | HLA-C*17:01 |

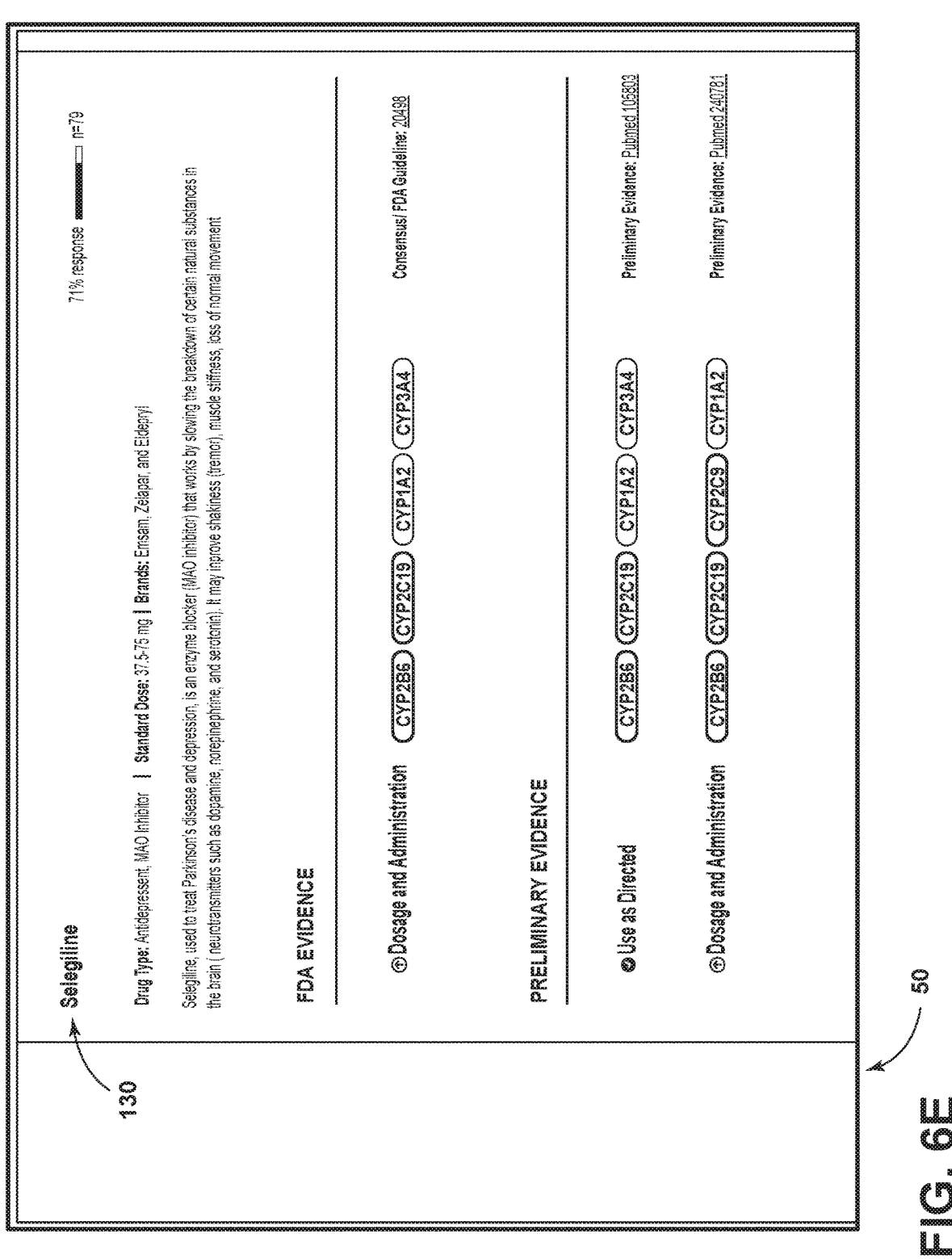

Selegiline

Drug Type: Antidepressant, MAO Inhibitor   |   Standard Dose: 37.5-75 mg   |   Brands: Emsam, Zelapar, and Eldepryl Selegiline, used to treat Parkinson's disease and depression, is an enzyme blocker (MAO inhibitor) that works by slowing the breakdown of certain natural substances in the brain ( neurotransmitters such as dopamine, norepinephrine, and serotonin). It may improve shakiness (tremor), muscle stiffness, loss of normal movement 71% response ▬▬▬▬ ☐ n=79

FDA EVIDENCE

⊕ Dosage and Administration    ( CYP2B6 ) ( CYP2C19 ) ( CYP1A2 ) ( CYP3A4 )    Consensus/ FDA Guideline: 20498

PRELIMINARY EVIDENCE

● Use as Directed    ( CYP2B6 ) ( CYP2C19 ) ( CYP1A2 ) ( CYP3A4 )    Preliminary Evidence: Pubmed 105809

⊕ Dosage and Administration    ( CYP2B6 ) ( CYP2C19 ) ( CYP2C9 ) ( CYP1A2 )    Preliminary Evidence: Pubmed 240781

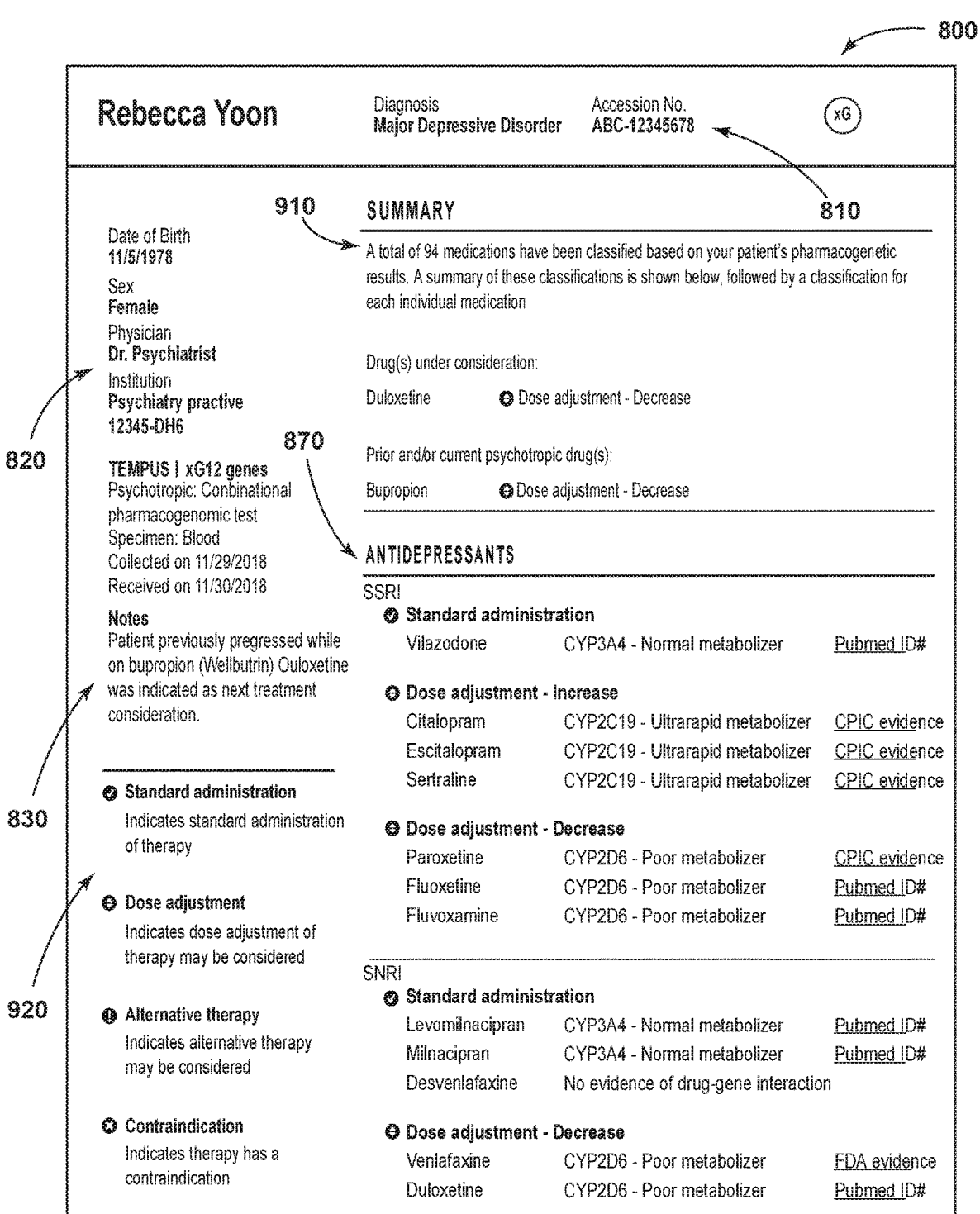

Rebecca Yoon

Diagnosis
Major Depressive Disorder

Accession No.
ABC-12345678 xG

910

SUMMARY

810

Date of Birth
11/5/1978

Sex
Female

Physician
Dr. Psychiatrist

Institution
**Psychiatry practive
12345-DH6**

A total of 94 medications have been classified based on your patient's pharmacogenetic results. A summary of these classifications is shown below, followed by a classification for each individual medication Drug(s) under consideration:

Duloxetine          ⊖ Dose adjustment - Decrease

870

Prior and/or current psychotropic drug(s):

Bupropion          ⊖ Dose adjustment - Decrease

820

TEMPUS | xG12 genes
Psychotropic: Conbinational
pharmacogenomic test
Specimen: Blood
Collected on 11/29/2018
Received on 11/30/2018

ANTIDEPRESSANTS

SSRI

Notes
Patient previously pregressed while on bupropion (Wellbutrin) Ouloxetine was indicated as next treatment consideration.

⊘ Standard administration

| | | |
|---|---|---|
| Vilazodone | CYP3A4 - Normal metabolizer | Pubmed ID# |

⊕ Dose adjustment - Increase

| | | |
|---|---|---|
| Citalopram | CYP2C19 - Ultrarapid metabolizer | CPIC evidence |
| Escitalopram | CYP2C19 - Ultrarapid metabolizer | CPIC evidence |
| Sertraline | CYP2C19 - Ultrarapid metabolizer | CPIC evidence |

830

⊘ Standard administration
Indicates standard administration of therapy

⊕ Dose adjustment
Indicates dose adjustment of therapy may be considered

⊖ Dose adjustment - Decrease

| | | |
|---|---|---|
| Paroxetine | CYP2D6 - Poor metabolizer | CPIC evidence |
| Fluoxetine | CYP2D6 - Poor metabolizer | Pubmed ID# |
| Fluvoxamine | CYP2D6 - Poor metabolizer | Pubmed ID# |

SNRI

⊘ Standard administration

| | | |
|---|---|---|
| Levomilnacipran | CYP3A4 - Normal metabolizer | Pubmed ID# |
| Milnacipran | CYP3A4 - Normal metabolizer | Pubmed ID# |
| Desvenlafaxine | No evidence of drug-gene interaction | |

920

⊕ Alternative therapy
Indicates alternative therapy may be considered

⊗ Contraindication
Indicates therapy has a contraindication

⊖ Dose adjustment - Decrease

| | | |
|---|---|---|
| Venlafaxine | CYP2D6 - Poor metabolizer | FDA evidence |
| Duloxetine | CYP2D6 - Poor metabolizer | Pubmed ID# |

Figure 9B:
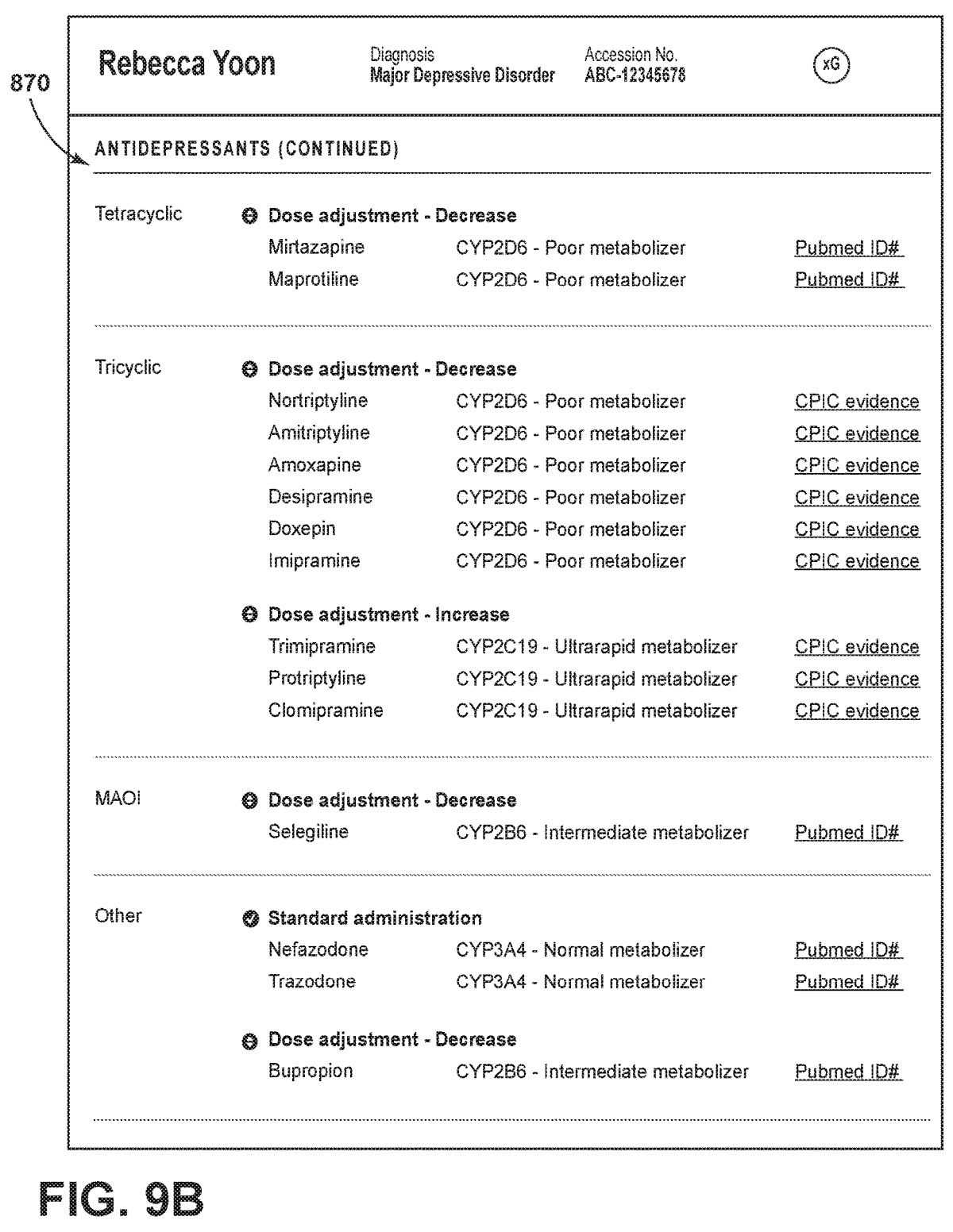

| Rebecca Yoon | Diagnosis Major Depressive Disorder | Accession No. ABC-12345678 | (xG) |

ANTIDEPRESSANTS (CONTINUED)

Tetracyclic    ⊕ Dose adjustment - Decrease

| Mirtazapine | CYP2D6 - Poor metabolizer | Pubmed ID# |
| Maprotiline | CYP2D6 - Poor metabolizer | Pubmed ID# |

Tricyclic    ⊕ Dose adjustment - Decrease

| Nortriptyline | CYP2D6 - Poor metabolizer | CPIC evidence |
| Amitriptyline | CYP2D6 - Poor metabolizer | CPIC evidence |
| Amoxapine | CYP2D6 - Poor metabolizer | CPIC evidence |
| Desipramine | CYP2D6 - Poor metabolizer | CPIC evidence |
| Doxepin | CYP2D6 - Poor metabolizer | CPIC evidence |
| Imipramine | CYP2D6 - Poor metabolizer | CPIC evidence |

⊕ Dose adjustment - Increase

| Trimipramine | CYP2C19 - Ultrarapid metabolizer | CPIC evidence |
| Protriptyline | CYP2C19 - Ultrarapid metabolizer | CPIC evidence |
| Clomipramine | CYP2C19 - Ultrarapid metabolizer | CPIC evidence |

MAOI    ⊕ Dose adjustment - Decrease

| Selegiline | CYP2B6 - Intermediate metabolizer | Pubmed ID# |

Other    ⊘ Standard administration

| Nefazodone | CYP3A4 - Normal metabolizer | Pubmed ID# |
| Trazodone | CYP3A4 - Normal metabolizer | Pubmed ID# |

⊕ Dose adjustment - Decrease

| Bupropion | CYP2B6 - Intermediate metabolizer | Pubmed ID# |

Figure 9C:
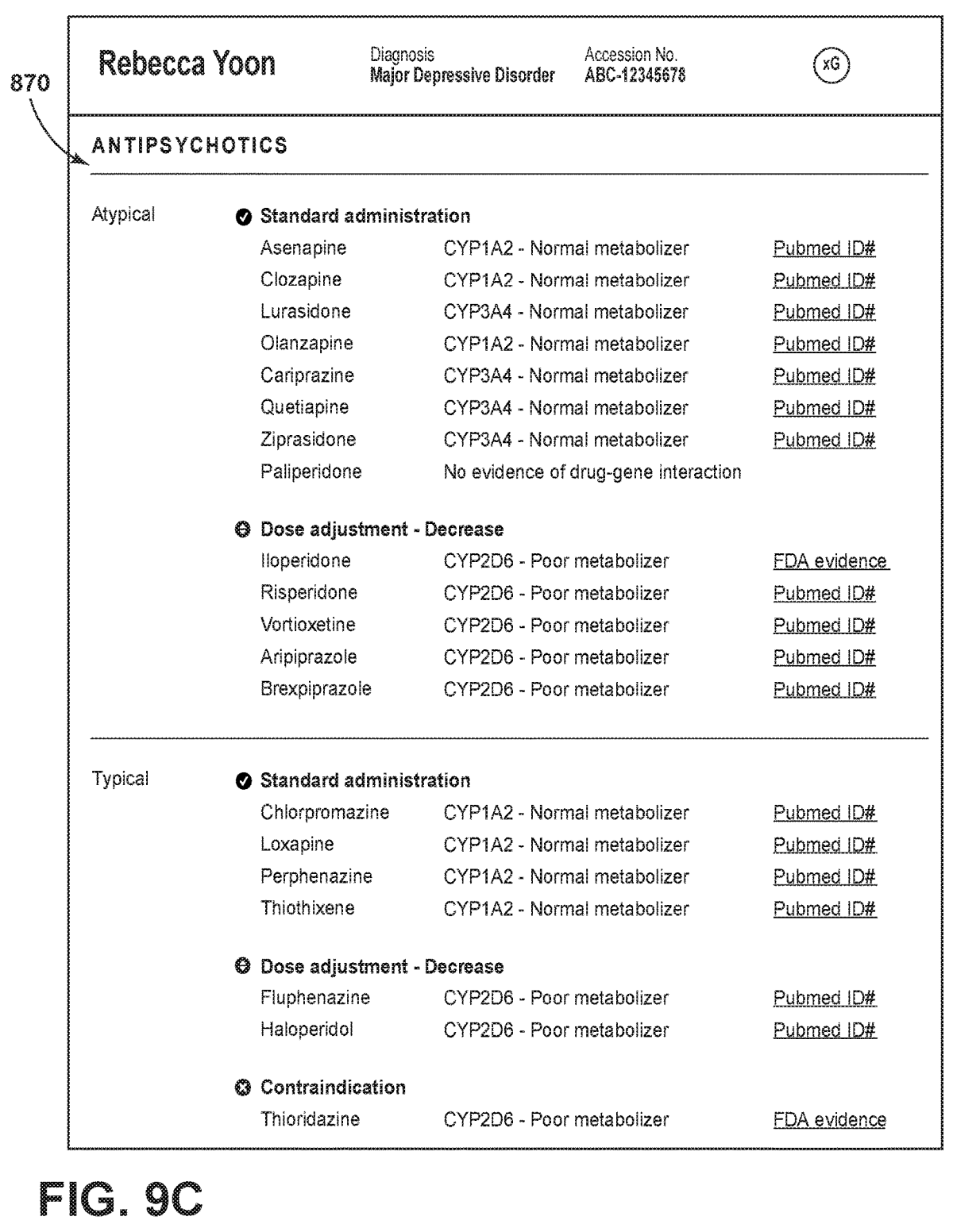

Rebecca Yoon    Diagnosis    Accession No.    (xG)
Major Depressive Disorder    ABC-12345678

ANTIPSYCHOTICS

Atypical    ✔ Standard administration

Asenapine    CYP1A2 - Normal metabolizer    Pubmed ID#
Clozapine    CYP1A2 - Normal metabolizer    Pubmed ID#
Lurasidone    CYP3A4 - Normal metabolizer    Pubmed ID#
Olanzapine    CYP1A2 - Normal metabolizer    Pubmed ID#
Cariprazine    CYP3A4 - Normal metabolizer    Pubmed ID#
Quetiapine    CYP3A4 - Normal metabolizer    Pubmed ID#
Ziprasidone    CYP3A4 - Normal metabolizer    Pubmed ID#
Paliperidone    No evidence of drug-gene interaction ⊖ Dose adjustment - Decrease

Iloperidone    CYP2D6 - Poor metabolizer    FDA evidence
Risperidone    CYP2D6 - Poor metabolizer    Pubmed ID#
Vortioxetine    CYP2D6 - Poor metabolizer    Pubmed ID#
Aripiprazole    CYP2D6 - Poor metabolizer    Pubmed ID#
Brexpiprazole    CYP2D6 - Poor metabolizer    Pubmed ID#

Typical    ✔ Standard administration

Chlorpromazine    CYP1A2 - Normal metabolizer    Pubmed ID#
Loxapine    CYP1A2 - Normal metabolizer    Pubmed ID#
Perphenazine    CYP1A2 - Normal metabolizer    Pubmed ID#
Thiothixene    CYP1A2 - Normal metabolizer    Pubmed ID#

⊖ Dose adjustment - Decrease

Fluphenazine    CYP2D6 - Poor metabolizer    Pubmed ID#
Haloperidol    CYP2D6 - Poor metabolizer    Pubmed ID#

⊗ Contraindication

Thioridazine    CYP2D6 - Poor metabolizer    FDA evidence

| Rebecca Yoon | Diagnosis<br>Major Depressive Disorder | Accession No.<br>ABC-12345678 | (xG) |

ANTICONVULSANTS

| Sodium channel inhibitor | ⊘ Standard administration | | |
| | Lamotrigine | UGT1A4 - Normal metabolizer | Pubmed ID# |
| | ❶ Alternative therapy – Adverse effects | | |
| | Oxcarbazepine | HLA-A*1502 - Present | CPIC evidence |
| | ⊗ Contraindication | | |
| | Carbamazepine | HLA-A*1502 - Present | FDA evidence |
| GABA augmenting agent | ⊘ Standard administration | | |
| | Chlordiazepoxide | CYP3A4 - Normal metabolizer | Pubmed ID# |
| Gabapentinoid | Standard administration | | |
| | Gabapentin | No evidence of drug-gene interaction | |
| Hydantoin derivative | ❶ Alternative therapy – Adverse effects | | |
| | Phenytoin | HLA-A*1502 - Present | CPIC evidence |
| Alpha-2-delta ligand | ⊘ Standard administration | | |
| | Pregabalin | CYP3A4 - Normal metabolizer | Pubmed ID# |
| Sulfamate | ⊘ Standard administration | | |
| | Topiramate | No evidence of drug-gene interaction | |
| Sulfonamide | ⊘ Standard administration | | |
| | Zonisamide | CYP3A4 - Normal metabolizer | Pubmed ID# |
| Other | ⊘ Standard administration | | |
| | Valproate | UGT1A4 - Normal metabolizer | Pubmed ID# |

Rebecca Yoon

Diagnosis
Major Depressive Disorder

Accession No.
ABC-12345678

(xG)

▲ ANXIOLYTICS

Benzodiazepine | ✓ Standard administration

| Clonazepam | UGT1A4 - Normal metabolizer | Pubmed ID# |
| Triazolam | CYP3A4 - Normal metabolizer | Pubmed ID# |

⊖ Dose adjustment - Decrease

| Lorazepam | UGT2B15 - Intermediate metabolizer | Pubmed ID# |
| Oxazepam | UGT2B15 - Intermediate metabolizer | Pubmed ID# |

⊖ Dose adjustment - Increase

| Diazepam | CYP2C19 - Ultrarapid metabolizer | CPIC evidence |
| Temazepam | CYP2C19 - Ultrarapid metabolizer | CPIC evidence |

❶ Alternative therapy - Adverse effects

| Clorazepate | HLA-A*1502 - Present | CPIC evidence |

⊗ Contraindication

| Alprazolam | HLA-B*1502 - Present | FDA evidence |

Other | ✓ Standard administration

| Buspirone | CYP3A4 - Normal metabolizer | Pubmed ID# |

Figure 9F:
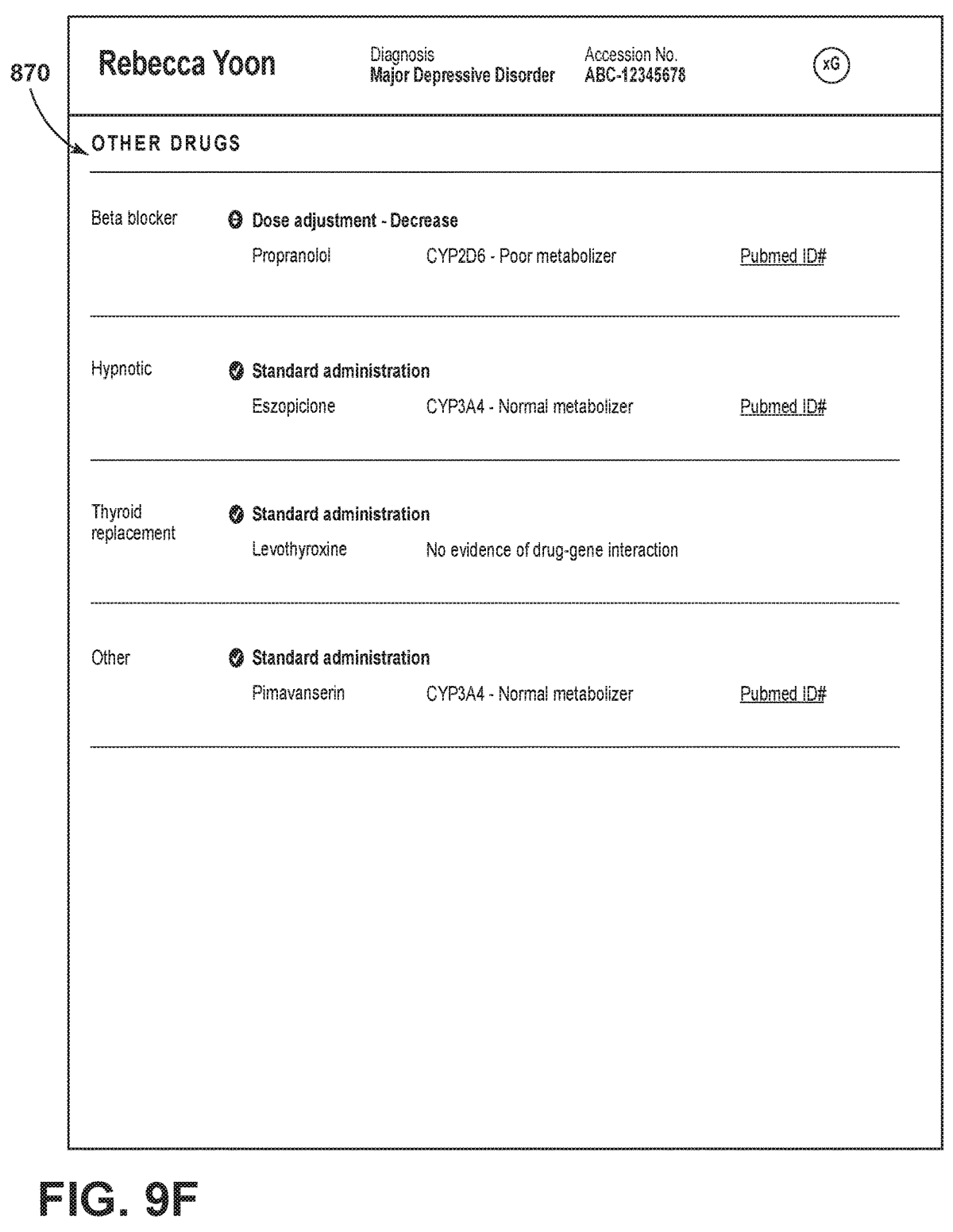

| Rebecca Yoon | Diagnosis<br>Major Depressive Disorder | Accession No.<br>ABC-12345678 | (xG) |

OTHER DRUGS

Beta blocker 🕈 Dose adjustment - Decrease

Propranolol   CYP2D6 - Poor metabolizer   Pubmed ID#

Hypnotic  ⊘ Standard administration

Eszopiclone   CYP3A4 - Normal metabolizer   Pubmed ID#

Thyroid   ⊘ Standard administration
replacement
     Levothyroxine   No evidence of drug-gene interaction Other   ⊘ Standard administration

Pimavanserin   CYP3A4 - Normal metabolizer   Pubmed ID#

Rebecca Yoon    Diagnosis    Accession No.
Major Depressive Disorder    ABC-12345678

---

PHARMACOGENOMIC RESULT DETAILS ( CYP2D6 )    *4/*5    Poor metabolizer

This person carries a CYP2D6 *4 allele and a CYP2D6 *5 allele. Both *4 and *5 alleles are predicted to have no CYP2D6 activity Therefore, this patient's genotype (*4/*5) is consistent with a poor metabolizer phenotype for CYP2D6 substrates. This patient may be at risk for a poor therapeutic response to drugs that are activated by CYP2D6, and at an increased risk to develop adverse effects when exposed to drugs that are inactivated by CYP2D6. Dose adjustments or alternative therapeutic agents not metabolized by CYP2D6 may be considered.

( CYP2C19 )    *17/*17  Ultrarapid metabolizer

This person carries two CYP2C19 *17 alleles. *17 alleles are predicted to have increased CYP2C19 activity. Therefore, this patient's genotype (*17/*17) is consistent with an ultrarapid metabolizer phenotype for CYP2 C19 substrates. This patient may be at risk for reduced efficacy or adverse effects to drugs that are metabolized by CYP2C19. Dose adjustments or alternative therapeutic agents not metabolized by CYP2C19 may be considered.

( CYP2C9 )    *1/*2    Intermediate metabolizer

This person carries one normal function CYP2C9 allele (*1) and one decreased function CYP2C9 allele (*2). Therefore, this pati ent's genotype (*1/*2) is consistent with an intermediate metabolizer phenotype for CYP2C9 substrates. This patient may be at risk for an adverse res ponse to drugs that are affected by CYP2C9. Dose adjustments or alternative therapeutic agents not affected by CYP2C9 may be considered.

( CYP2B6 )    *1/*6    Intermediate metabolizer

This person carries one normal function CYP2B6 allele (*1) and one no function CYP2B6 allele (*6). Therefore, this patient's genotype (*1/*6) is consistent with an intermediate metabolizer phenotype for CYP 2B6 substrates. Dose adjustments or alternative therapeutic agent s not affected by CYP2B6 may be considered.

( CYP1A2 )    *1/*1    Extensive/normal metabolizer

This person carries two CYP2B6 *1 alleles. *1 alleles are predicted to have normal CYP1A2 activity. Therefore, this patient's genotype (*1/*1) is consistent with an extensive (normal) metabolizer phenotype for CYP1A2. There is no reason to selectively adjust most medicati ons metabolized by CYP1A2.

( CYP3A4 )    *1/*1    Extensive/normal metabolizer

This person carries two CYP3A4 *1 alleles. *1 alleles are predicted to have normal CYP3A4 activity. Therefore, this patient's genotype (*1/*1) is consistent with an extensive (normal) metabolizer phenotype for CYP3A4. There is no reason to selectively adjust most medicati ons metabolized by CYP3A4.

( UGT1A4 )    *1/*1    Extensive/normal metabolizer

This person carries two UGT1A4 *1 alleles. *1 alleles are predicted to have normal UGT1A4 activity. Therefore, this patient's genotype (*1/*1) is consistent with an extensive (normal) metabolizer phenotype for UGT1A4. There is no reason to selectively adjust most medicatio ns metabolized by UGT1A4.

Rebecca Yoon      Diagnosis      Accession No.
                  Major Depressive Disorder   ABC-12345678

PHARMACOGENOMIC RESULT DETAILS (CONTINUED)

( UGT2B15 )   *2/*2   Intermediate metabolizer

This person carries two UGT2B15 *2 alleles. *2 alleles are predicted to have decreased UGT2B15 activity. Therefore, this patient's genotype (*2/*2) is consistent with an intermediate metabolizer phenotype for UGT2B15 substrates. Dose adjustments or alternative therapeutic agent not affected by UGT2B15 may be considered.

( SLC6A4 )   S/S   Reduced responder

This person is apparently homozygous for the short promoter (S) allele of the serotonin transporter SLC6A4. Homozygous carriers of the SLCA4 short promoter allele have a decreased likelihood to achieve remission using selective serotonin reuptake inhibitors, and may have an increased risk to develop adverse effects. SSRI alternative therapies may be considered.

( HTR2A )   G/G   Increased sensitivity

This person is apparently homozygous for the promoter G allele c.-998G>A (rs6311, also previously known as -1438A>G) in the serotonin transporter HTR2A. Homozygous carriers of this G allele may be at an increased risk to develop adverse effects when treated with certain selective serotonin reuptake inhibitors. Alternative therapeutic agents may be considered.

( HLA-A*13:01 )   Present  Increased risk

This patient carries the HLA-A *13:01 allele. This genotype has been associated with an increased risk of developing maculopapular exanthema, drug reaction with eosinophilia and systemic symptoms (DRESS), and Stevens-Johnson syndrome (STS) and toxic epidermal necrolysis in patients treated with drugs such as carbamazepine. Alternative therapeutic agents may be considered ( HLA-B*15:02 )   Present  Increased risk This patient carries the HLA-B *15:02 allele. This genotype has been associated with an increased risk of developing Stevens-Johnson syndrome (STS) and toxic epidermal necrolysis in patients treated with drugs such as carbamazepine. Alternative therapeutic agents may be considered.

940

SECONDARY FINDINGS DETAILS

( BRCA2 )   c.4965C>G  p.Tyr1655*  NM_00059.3  Chr13:32913457  Stop gain

This patient has a heterozygous germline pathogenic variant in BRCA2. BRCA2 encodes a nuclear phosphoprotein which helps maintain DNA stability through homologous recombination based DNA double stranded break repair and involvement in DNA damage checkpoint control. Germline pathogenic variants in BRCA2 are associated with an increased risk of development of breast, ovarian and fallopian tube cancers in women. Men with pathogenic variants in BRCA2 are at an increased risk to develop breast and prostate cancer, and both men and women are at an increased risk to develop pancreatic cancer. Genetic counseling and appropriate cancer screening are recommended for this patient and any potentially affected family members.

FIG. 9H

| Sample Patient B | Diagnosis Major depressive disorder | Patient ID XG-P-00013 | MOLECULAR RESULTS  |

| Date of Birth 1/1/1990 | Sex Female | Ordering Provider Psychiatrist Name | Institution Psychiatry Clinic |

Tempus|nP

Specimen: Saliva
Collected On: 01/01/2020
Received On: 01/03/2020

SUMMARY

Molecular results and associated phenotypes for the 15 genes analyzed are summarized below.
Please see Assay Methodology and Limitations for more information regarding these results.

PHARMACOGENOMIC RESULTS

1004          1008

| Gene | Genotype | Phenotype |
|------|----------|-----------|
| CYP1A2 | *1A/*1F | Normal Metabolizer |
| CYP2B6 | *1/*6 or *4/*9 | Intermediate Metabolizer |
| CYP2C19 | *1/*1 | Normal Metabolizer |
| CYP2C9 | *1/*1 | Normal Metabolizer |
| CYP2D6 | *4/*4 | Poor Metabolizer |
| CYP3A4 | *1/*1 | Normal Metabolizer |
| CYP3A5 | *1/*3 | Intermediate Metabolizer |
| HLA-A | HLA-A*31:01 Negative | Normal |
| HLA-B | HLA-B:*15:02 Negative | Normal |
| HTR2A | rs6311 -1438G/G | Increased Risk |
| SLC6A4 | Short/Short | Poor Function |
| UGT1A4 | *1/*1 | Normal Metabolizer |
| UGT2B15 | *2/*2 | Poor Metabolizer |

ADDITIONAL GENOTYPING RESULTS

| Gene | Variant | Results |
|------|---------|---------|
| COMT | rs4680 (V158M) | Val/Val Homozygous |
| MTHFR | rs1801131 (A1298C) | A/C Heterozygous |
| MTHFR | rs1801133 (C677T) | C/T Heterozygous |

FIG. 10          1000

Sample Patient B

Diagnosis
Major depressive disorder

REFERENCE INFORMATION   (nP)

| Date of Birth | Sex | Ordering Provider | Institution |
|---|---|---|---|
| 1/1/1990 | Female | Psychiatrist Name | Psychiatry Clinic |

CLASSIFICATIONS

⊘ Standard administrations

No sufficient evidence suggesting alternative administration was identified. Evidence supporting standard administration based on gene-drug interactions will be cited as such.

⊖ Dosing Considerations

Tempus classifies medications as "dose adjustment" when evidence suggests that a higher or lower dose may increase efficacy or lower risk for adverse reactions.

⊕ Additional risks to consider

Therapies with this classification may pose a higher risk for adverse reactions or evidence may suggest this medication to be less effectively processed by a patient. Therefore, the provider may want to consider alternative medications if applicable.

⊗ Contraindications

Only medications with an explicit FDA contraindication associated with your patient's PGx results will be labeled as contraindicated. This is designed to help differentiate the potential significance of a contraindication finding.

1020

ANTIDEPRESSANTS

SUMMARY

Tempus classifies medications into the categories listed below based on known gene-drug interactions. Evidence supporting the designated medication classification is cited with each gene-drug interaction. These results have been personalized to your patient based on the molecular results delivered separately and does not include information based on drug-drug interactions for drugs that the patient may currently be prescribed. The medications listed below are not specific to the patient's condition or diagnosis, including whether specific patient characteristics are within the labeled use of the medications. FDA labels for indications of use, dosing guidelines, and other pertinent information related to treatment should be reviewed before prescribing medications.

NOTE: The information provided is solely related to gene-drug interactions and does not include information regarding drug-drug interactions or account for current medication regimens.

Drug(s) under consideration:

| Lorazepam | ⊖ Dosing consideration - Decrease |
|---|---|

Prior and/or current psychotropic drug(s):

Medications will only be listed if they are analyzed for gene-drug interactions.

| Fluoxetine | ⊘ Standard administration |
|---|---|
|  | ⊕ Additional risks to consider |
| Paroxetine | ⊘ Standard administration |
|  | ⊕ Additional risks to consider |

1012

| SSRI | 1024 ⊘ Standard administration | 1028 | 1032 |
|---|---|---|---|
| 1016 |  Vilazodone | CYP3A4 - Normal Metabolizer | FDA |
|  | 1036 Conflicting Evidence | 1040 | 1044 |
|  |  Citalopram |  | |
|  | ⊘ Standard administration | CYP2C19 - Normal Metabolizer | CPIC |
|  | ⊘ Standard administration | HTR2A - Increased Risk | PMID: 24021217 |

1048 Evidence suggests that side effect risk is meaningfully increased but not clinically impactful (PMID: 2402121); evidence with regard to efficacy is conflicting/insufficient to recommend therapeutic changes (PMIDs: 25980509, 22522758, 31066578, 30178121, 26766959, 19937159)

| ⊕ Additional risks to consider | SLC6A4 - Poor Function | PMID: 28654193 |
|---|---|---|

1052

Escitalopram

| ⊘ Standard administration | CYP2C19 - Normal Metabolizer | CPIC |
|---|---|---|
| ⊘ Standard administration | HTR2A - Increased Risk | PMID: 24021217 |

ANTIDEPRESSANTS (CONTINUED)                                              Sample Patient B

SSRI (continued)        Conflicting Evidence (continued)

Escitalopram (continued)

🛈 Additional risks to consider        SLC6A4 - Poor Function          PMID: 28654193

Fluoxetine

✅ Standard administration            CYP2D6 - Poor Metabolizer       FDA

✅ Standard administration            HTR2A - Increased Risk          PMID: 24021217

Evidence suggests that side e    ffect risk is meaningfully increased but
not clinically impactful (PMID:    2402121); evidence with regard to
efficacy is conflicting/insu    fficient to recommend therapeutic changes
(PMIDs: 25980509, 22522758, 31066578, 30178121, 26766959, 19937159)

🛈 Additional risks to consider        SLC6A4 - Poor Function          PMID: 28654193

Fluvoxamine

✅ Standard administration            HTR2A - Increased Risk          PMID: 24021217

Evidence suggests that side e    ffect risk is meaningfully increased but
not clinically impactful (PMID:    2402121); evidence with regard to
efficacy is conflicting/insu    fficient to recommend therapeutic changes
(PMIDs: 25980509, 22522758, 31066578, 30178121, 26766959, 19937159)

⊖ Dosing consideration - Decrease      CYP2D6 - Poor Metabolizer       CPIC

🛈 Additional risks to consider        SLC6A4 - Poor Function          PMID: 28654193

Paroxetine

✅ Standard administration            HTR2A - Increased Risk          PMID: 24021217

Evidence suggests that side e    ffect risk is meaningfully increased but
not clinically impactful (PMID:    2402121); evidence with regard to
efficacy is conflicting/insu    fficient to recommend therapeutic changes
(PMIDs: 25980509, 22522758, 31066578, 30178121, 26766959, 19937159)

🛈 Additional risks to consider        CYP2D6 - Poor Metabolizer       CPIC

🛈 Additional risks to consider        SLC6A4 - Poor Function          PMID: 28654193

Sertraline

✅ Standard administration            CYP2C19 - Normal Metabolizer    CPIC

✅ Standard administration            HTR2A - Increased Risk          PMID: 24021217

Evidence suggests that side e    ffect risk is meaningfully increased but
not clinically impactful (PMID:    2402121); evidence with regard to
efficacy is conflicting/insu    fficient to recommend therapeutic changes
(PMIDs: 25980509, 22522758, 31066578, 30178121, 26766959, 19937159)

🛈 Additional risks to consider        SLC6A4 - Poor Function          PMID: 28654193

---

SNRI          ✅ Standard administration

1056        Desvenlafaxine      CYP3A4 - Normal Metabolizer      FDA

Levomilnacipran     CYP3A4 - Normal Metabolizer      FDA

Milnacipran         no relevant genes identified     FDA

⊖ Dosing consideration - Decrease

Venlafaxine         CYP2D6 - Poor Metabolizer        FDA

Conflicting Evidence

Duloxetine

✅ Standard administration            CYP1A2 - Normal Metabolizer      FDA

FIG. 12                        ↖ 1000

ANTIDEPRESSANTS (CONTINUED)                                                                 Sample Patient B

| SNRI (continued) | Conflicting Evidence (continued) | | |
|---|---|---|---|
| Tetracyclic 1056 | ⊘ Standard administration | | |
| | Maprotiline | CYP2D6 - Poor Metabolizer | FDA |
| | Mirtazapine | CYP2D6 - Poor Metabolizer | PMID: 15538128 |

| Tricyclic | ⊘ Standard administration | | |
|---|---|---|---|
| | Amoxapine | no relevant genes identified | FDA |
| | ⊖ Dosing consideration - Decrease | | |
| | Protriptyline | CYP2D6 - Poor Metabolizer | FDA |
| | | Classification based on studies that show drug concentration changes in the blood | |
| | ❗ Additional risks to consider | | |
| | Amitriptyline | CYP2D6 - Poor Metabolizer | CPIC |
| | | CYP2C19 - Normal Metabolizer | CPIC |
| | Clomipramine | CYP2C19 - Normal Metabolizer | CPIC |
| | | CYP2D6 - Poor Metabolizer | CPIC |
| | Desipramine | CYP2D6 - Poor Metabolizer | CPIC |
| | Doxepin | CYP2D6 - Poor Metabolizer | CPIC |
| | | CYP2C19 - Normal Metabolizer | CPIC |
| | Imipramine | CYP2D6 - Poor Metabolizer | CPIC |
| | | CYP2C19 - Normal Metabolizer | CPIC |
| | Nortriptyline | CYP2D6 - Poor Metabolizer | CPIC |
| | Trimipramine | CYP2D6 - Poor Metabolizer | CPIC |
| | | CYP2C19 - Normal Metabolizer | CPIC |

| GABA Modulator | ⊘ Standard administration | | |
|---|---|---|---|
| | Brexanolone | no relevant genes identified | FDA |

| MAOI | ⊘ Standard administration | | |
|---|---|---|---|
| | Isocarboxazid | no relevant genes identified | FDA |
| | Phenelzine | no relevant genes identified | FDA |
| | Selegiline | no relevant genes identified | FDA |
| | Tranylcypromine | no relevant genes identified | FDA |

| NMDA receptor antagonist | ⊘ Standard administration | | |
|---|---|---|---|
| | Esketamine | no relevant genes identified | FDA |

| Other | Standard administration | | |
|---|---|---|---|
| | Bupropion | CYP2B6 - Intermediate Metabolizer | PMID: 23344581  PMID: 25565674 |
| | Nefazodone | no relevant genes identified | FDA |

FIG. 13

1000

| ANTIDEPRESSANTS (CONTINUED) | | | Sample Patient B |
|---|---|---|---|

Other (continued)    ⊖ Dosing consideration - Decrease

| | Vortioxetine | CYP2D6 - Poor Metabolizer | FDA |
|---|---|---|---|
| | | Classification based on inhibitor or inducer studies (PMID: 27040602, 23327581) | |

_1060_

ANTIPSYCHOTICS

Atypical    ⊘ Standard administration

| | Asenapine | CYP1A2 - Normal Metabolizer | FDA |
|---|---|---|---|
| | Cariprazine | CYP3A4 - Normal Metabolizer | FDA |
| | Lurasidone | CYP3A4 - Normal Metabolizer | FDA |
| | Olanzapine | CYP1A2 - Normal Metabolizer | FDA |
| | Paliperidone | CYP3A4 - Normal Metabolizer | FDA |
| | Pimavanserin | CYP3A4 - Normal Metabolizer | FDA |
| | Quetiapine | CYP3A4 - Normal Metabolizer | FDA |
| | | CYP3A5 - Intermediate Metabolizer | PMID: 25254417 |
| | Risperidone | CYP2D6 - Poor Metabolizer | FDA |
| | Ziprasidone | CYP3A4 - Normal Metabolizer | FDA |

⊖ Dosing consideration - Decrease

| | Brexpiprazole | CYP2D6 - Poor Metabolizer | FDA |
|---|---|---|---|

Conflicting Evidence

Aripiprazole

⊘ Standard administration    CYP3A4 - Normal Metabolizer    FDA

⊖ Dosing consideration - Decrease CYP2D6 - Poor Metabolizer    FDA
　　　　　　　　　　　　　　　Classification based on inhibitor or inducer studies (PMID: 27040602, 23327581)

Clozapine

⊘ Standard administration    CYP1A2 - Normal Metabolizer    PMID: 12618594

⊖ Dosing consideration - Decrease  CYP2D6 - Poor Metabolizer    FDA
　　　　　　　　　　　　　　　Classification based on studies that show drug concentration changes in the blood Iloperidone ⊘ Standard administration    CYP3A4 - Normal Metabolizer    FDA ⊖ Dosing consideration - Decrease CYP2D6 - Poor Metabolizer    FDA
　　　　　　　　　　　　　　　Classification based on studies that show drug concentration changes in the blood Typical    ⊘ Standard administration

| | Chlorpromazine | CYP1A2 - Normal Metabolizer | FDA |
|---|---|---|---|
| | | CYP2D6 - Poor Metabolizer | FDA |
| | Fluphenazine | CYP1A2 - Normal Metabolizer | FDA |
| | Loxapine | no relevant genes identified | FDA |
| | Thiothixene | no relevant genes identified | FDA |
| | Trifluoperazine | no relevant genes identified | FDA |

FIG. 14          _1000_

| ANTIPSYCHOTICS (CONTINUED) | | | Sample Patient B |
|---|---|---|---|
| Typical (continued) | ⊖ Dosing consideration - Decrease | | |
| | Haloperidol | CYP2D6 - Poor Metabolizer | DPWG |
| | | Classification based on studies that show drug concentration changes in the blood | |
| | ⊗ Contraindication | | |
| | Thioridazine | CYP2D6 - Poor Metabolizer | FDA |
| | ❶ Additional risks to consider | | |
| | Perphenazine | CYP2D6 - Poor Metabolizer | FDA |

1064

ANTICONVULSANTS

| Hydantoin derivative | ✓ Standard administration | | |
|---|---|---|---|
| | Phenytoin | CYP2C9 - Normal Metabolizer | CPIC |
| | | HLA-B*15:02 - Negative | CPIC |
| Carbamate | ✓ Standard administration | | |
| | Felbamate | no relevant genes identified | FDA |
| SV2A inhibtor | ✓ Standard administration | | |
| | Levetiracetam | no relevant genes identified | FDA |
| Sulfonamide | ✓ Standard administration | | |
| | Zonisamide | CYP3A4 - Normal Metabolizer | FDA |
| Benzodiazepine | ✓ Standard administration | | |
| | Clobazam | CYP2C19 - Normal Metabolizer | FDA |
| Gabapentinoid | ✓ Standard administration | | |
| | Gabapentin | no relevant genes identified | FDA |
| Alpha-2-delta ligand | ✓ Standard administration | | |
| | Pregabalin | no relevant genes identified | FDA |
| AMPA receptor antagonist | ✓ Standard administration | | |
| | Perampanel | CYP3A4 - Normal Metabolizer | FDA |
| Barbiturate | ✓ Standard administration | | |
| | Phenobarbital | no relevant genes identified | FDA |

| ANTICONVULSANTS (CONTINUED) | | | Sample Patient B |
|---|---|---|---|
| Sulfamate | ⊘ Standard administration | | |
| | Topiramate | no relevant genes identified | FDA |
| NSAID | ⊘ Standard administration | | |
| | Aspirin | no relevant genes identified | FDA |
| Cannabinoid-derived | ⊘ Standard administration | | |
| | Epidiolex | CYP2C19 - Normal Metabolizer | FDA |
| | | CYP3A4 - Normal Metabolizer | FDA |
| Other | ⊘ Standard administration | | |
| | Lacosamide | no relevant genes identified | FDA |
| | Lamotrigine | HLA-B*15:02 – Negative | PMID: 30015149 |
| | | UGT1A4 - Normal Metabolizer | FDA |

1068

ANXIOLYTICS

| | | | |
|---|---|---|---|
| Benzodiazepine | ⊘ Standard administration | | |
| | Alprazolam | CYP3A4 - Normal Metabolizer | FDA |
| | | CYP3A5 - Intermediate Metabolizer | FDA |
| | Chlordiazepoxide | no relevant genes identified | FDA |
| | Clonazepam | CYP3A4 - Normal Metabolizer | FDA |
| | Clorazepate | no relevant genes identified | FDA |
| | Diazepam | CYP2C19 - Normal Metabolizer | FDA |
| | | CYP3A4 - Normal Metabolizer | FDA |
| | Temazepam | no relevant genes identified | FDA |
| | Triazolam | CYP3A4 - Normal Metabolizer | FDA |
| | ⊖ Dosing consideration - Decrease | | |
| | Lorazepam | UGT2B15 - Poor Metabolizer | PMID: 15961980 |
| | Oxazepam | UGT2B15 - Poor Metabolizer | PMID: 15044558 PMID: 19916996 |
| | | Classification based on studies that show drug concentration changes in the blood | |
| Other | ⊘ Standard administration | | |
| | Buspirone    1072 | CYP3A4 - Normal Metabolizer | FDA |

MOOD STABILIZERS

| | | | |
|---|---|---|---|
| Antimanic | ⊘ Standard administration | | |
| | Lithium | no relevant genes identified | FDA |

MOOD STABILIZERS (CONTINUED)                                                    Sample Patient B Anticonvulsant          ⊘ Standard administration
                          Oxcarbazepine        HLA-A*31:01 - Negative              CPICCPIC
                                               HLA-B*15:02 - Negative              CPIC
                          Valproic Acid        no relevant genes identified       FDA

1076
ANTIMANICS

Mood stabilizer         ⊘ Standard administration
                          Carbamazepine        HLA-A*31:01 - Negative              CPIC
                                               HLA-B*15:02 - Negative              CPIC
                              1080
HYPNOTICS Other                   ⊘ Standard administration
                          Eszopiclone          CYP3A4 - Normal Metabolizer        FDA
                          Ramelteon            CYP1A2 - Normal Metabolizer        FDA
                          Zolpidem             CYP3A4 - Normal Metabolizer        FDA
                              1084
VMAT2 INHIBITORS Other                   ⊖ Dosing consideration - Decrease
                          Deutetrabenazine     CYP2D6 - Poor Metabolizer          FDA
                          Tetrabenazine        CYP2D6 - Poor Metabolizer          FDA
                                               Classification based on studies that show drug
                                               oncentration changes in the blood
                        Conflicting Evidence
                          Valbenazine
                            ⊘ Standard administration      CYP3A4 - Normal Metabolizer    FDA
                            ⊖ Dosing consideration - Decrease CYP2D6 - Poor Metabolizer   FDA
                                                         Classification based on studies that show drug
                                                         concentration changes in the blood
                              1088
ADHD MEDICATIONS Stimulant               ⊘ Standard administration
                          Methylphenidate      no relevant genes identified       FDA ⊖ Dosing consideration - Decrease
                          Dextroamphetamine    CYP2D6 - Poor Metabolizer          FDA
                                               Classification based on inhibitor or inducer studies (PMID: 27040602, 23327581)

Dextroamphetamine/   CYP2D6 - Poor Metabolizer          FDA
                          Amphetamine
                                               Classification based on inhibitor or inducer studies (PMID: 27040602, 23327581)

FIG. 17             1000

ADHD MEDICATIONS (CONTINUED)                                                    Sample Patient B Stimulant (continued)    ⊖ Dosing consideration - Decrease (continued)

Lisdexamfetamine    CYP2D6 - Poor Metabolizer              FDA
                                             Classification based on inhibitor or inducer studies (PMID: 27040602, 23327581)

Non-stimulant            ⊖ Dosing consideration - Decrease

Atomoxetine         CYP2D6 - Poor Metabolizer              FDA CPIC

OTHER                              1092

Antiplatelet - P2Y12     ⊘ Standard administration
inhibitor
                         Clopidogrel         CYP2C19 - Normal Metabolizer           FDA Opioid analgesic         ❶ Additional risks to consider Codeine             CYP2D6 - Poor Metabolizer              CPIC
                         Tramadol            CYP2D6 - Poor Metabolizer              DPWG Antiestrogen -           ❶ Additional risks to consider
Selective estrogen
receptor modulator       Tamoxifen           CYP2D6 - Poor Metabolizer              CPIC Anxiolytic - beta-       ⊘ Standard administration
blocker
                         Propranolol         CYP2D6 - Poor Metabolizer              FDA NMDA receptor            ❶ Additional risks to consider
antagonist
                         Dextromethorphan and  CYP2D6 - Poor Metabolizer            FDA
                         Quinidine Classification based on studies that show drug concentration changes in the blood Antifungal - triazole    ⊘ Standard administration Voriconazole        CYP2C19 - Normal Metabolizer           CPIC

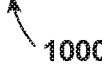

DATA-BASED MENTAL DISORDER RESEARCH AND TREATMENT SYSTEMS AND METHODS

CROSS-REFERENCE TO RELATED APPLICATIONS

This application is a continuation of U.S. patent application Ser. No. 17/207,972, filed Mar. 22, 2021, which is a continuation of U.S. patent application Ser. No. 16/984,072, filed Aug. 3, 2020, now U.S. Pat. No. 10,978,196, which claims benefit of U.S. Provisional Application 62/882,466, filed Aug. 2, 2019, and claims benefit of International Application PCT/US2019/056713, filed Oct. 17, 2019, which claims the benefit of U.S. Application 62/746,997 filed Oct. 17, 2018, the content of which is incorporated herein by reference in their entireties.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The instant application contains a table that has been submitted in ASCII format via EFS-web and is hereby incorporated by reference in its entirety. Said ASCII copy, created on Aug. 2, 2019, is named TABLE-1-List-of-Genes.txt and is 147,138 bytes in size.

LENGTHY TABLES

The patent contains a lengthy table section. A copy of the table is available in electronic form from the USPTO web site (https://seqdata.uspto.gov/docdetail?docId=US12683008B2). An electronic copy of the table will also be available from the USPTO upon request and payment of the fee set forth in 37 CFR 1.19(b)(3).

TECHNICAL FIELD

The present invention relates to systems and methods for obtaining and employing data related to clinical, physical, and genomic patient characteristics as well as diagnosis, treatments and treatment efficacy to provide a suite of tools to healthcare providers, researchers, and other interested parties enabling those entities to make clinical decisions, develop new mental disorder state-treatment-results insights, and improve overall patient healthcare.

BACKGROUND

There have been more than 50 FDA approved antipsychotic and antidepressant therapies available in the last 40 years, yet patients are still subjected to trial and error methodologies to find a successful treatment. Despite an abundance of available drugs and clinical trials comparing efficacy across these commonly used antidepressants, more than 70% of patients still fail to respond to their first therapy and between 10 and 30% fail to respond to medication at all. Knowledge about treatment results is often based on analysis of empirical data developed over decades or even longer time periods, during which physicians and/or researchers have recorded treatment results for many different patients and reviewed those results to identify generally successful, ailment specific treatments. Researchers and physicians give medicine to patients or treat an ailment in some other fashion, observe results and, if the results are good, use the treatments again for similar ailments. If treatment results are bad, a physician forgoes prescribing the associated treatment for a next encountered similar ailment and instead tries some other treatment. Treatment results are sometimes published in medical journals and/or periodicals so that many physicians can benefit from a treating physician's insights and treatment results.

In treatment of at least some mental disorders, such as depression states, treatment and results data is simply inconclusive. For example, in treatment of some depression states seemingly indistinguishable patients with similar conditions often react differently to similar treatment plans so that there is no cause and effect between patient conditions and disparate treatment results. For instance, two women may be the same age, indistinguishably physically fit and diagnosed with the same depression state (such as similar physical symptoms, mental symptoms, BDI-II score, PHQ-9 score, etc.). Here, the first woman may respond to a depression treatment plan well and may find symptom relief quickly and with minimal side effects, while the second woman, administered the same treatment plan, may suffer several severe adverse side effects and may never find relief from her initial depression symptoms. Disparate treatment results for seemingly similar depression states exacerbate efforts to develop treatment and results data sets and prescriptive activities.

Recognizing that different patients experience different results given effectively the same treatments in some cases, researchers and physicians often develop additional guidelines around how to optimize ailment treatments based on specific patient mental disorder, such as depression state. For instance, while a first treatment may be best for a younger, relatively healthy woman suffering from depression, a second treatment associated with fewer adverse side effects may be optimal for an older, relatively frail man with the same depression diagnosis.

In these cases, unfortunately, there are factors involved in the mental disorder (e.g., depression state factors), that have cause and effect relationships to specific treatment results that are simply currently unknown, and therefore those factors cannot be used to optimize specific patient treatments at this time. Furthermore, more than seventy percent of patients do not respond to the first line of drug treatments. With more than 43,800,000 American patients having mental health related diagnosis, there exists a need to learn from the greater than seventy percent ineffective first line of drug treatments to improve therapy selection on an initial basis.

Genetic testing has been explored to some extent as another mental disorder (e.g., depression) factor (such as another patient condition) that can affect mental disorder (e.g., depression) treatment efficacy. It is believed that there are likely many DNA and treatment result cause-and-effect relationships that have yet to be discovered. One problem with genetic testing is that the testing is expensive and can be cost prohibitive in many cases—oftentimes, insurance companies refuse to cover the cost.

Another problem with genetic testing for treatment planning is that, if genetic testing is performed, often there is no clear linkage between resulting genetic factors and treatment efficacy. In other words, in most cases, how genetic test results can be used to prescribe better treatment plans for patients is not fully known, so the extra expense associated with genetic testing in specific cases cannot be justified. Thus, while promising, genetic testing as part of mental disorder treatment planning has been minimal or sporadic at best.

For some mental disorders (e.g., such as some depression states), treatments and associated results are generally consistent and acceptable (such as minimal or at least understood side effects). In other cases, however, treatment results associated with other depression states is underdeveloped and/or inaccessible for several reasons.

First, there are many factors that affect treatment efficacy including many different types of patient conditions where different conditions render some treatments more efficacious for one patient than other treatments or for one patient as opposed to other patients. Clearly capturing specific patient conditions that do or may have a cause and effect relationship to treatment results is not easy, and some causal conditions may not be appreciated and captured at all.

Second, for most depression states, there are several different treatment options where each general option can be customized for a specific mental disorder (e.g., a specific depression state) and patient condition set. The plethora of treatment and customization options in many cases makes it difficult to accurately capture treatment and results data in a normalized fashion as there are no clear standardized guidelines for how to capture that type of information.

Third, in most cases patient treatments and results are not published for general consumption and therefore are simply not accessible to be combined with other treatment and results data to provide a more fulsome overall data set. In this regard, many physicians see treatment results that are within an expected range of efficacy and may conclude that those results cannot add to the overall depression treatment knowledge base; those results often are not published. The problem here is that the expected range of efficacy can be large (such as 20% of patients experience a significant reduction in symptoms, 40% of patients experience a moderate reduction in symptoms, 20% experience a mild reduction in symptoms, and 20% do not respond to a treatment plan) so that all treatment results are within an expected efficacy range and treatment result nuances are simply lost.

Fourth, currently there is no easy way to build on and supplement many existing illness-treatment-results databases. As such, as more data is generated, the new data and associated results cannot be added to existing databases as evidence of treatment efficacy or to challenge efficacy. Thus, for example, if a researcher publishes a study in a medical journal, there is no easy way for other physicians or researchers to supplement the data captured in the study. Without data supplementation over time, treatment and results corollaries cannot be tested and confirmed or challenged.

Fifth, the knowledge base around depression treatments is always growing with different clinical trials in different stages around the world so that if a physician's knowledge is current today, her knowledge will be dated within months. Thousands of articles relevant to mental disorders, broadly, or depression states specifically, are published each year and many are verbose and/or intellectually thick so that the articles are difficult to read and internalize, especially by extremely busy physicians that have limited time to absorb new materials and information. Distilling publications down to those that are pertinent to a specific physician's practice takes time and is an inexact endeavor in many cases.

Sixth, in most cases there is no clear incentive for physicians to memorialize a complete set of treatment and results data and, in fact, the time required to memorialize such data can operate as an impediment to collecting that data in a useful and complete form. To this end, prescribing and treating physicians know what they know and painstakingly capturing a complete set of mental disorder details (e.g., depression state), treatment, and results data without getting something in return (such as a new insight, a better prescriptive treatment tool, etc.) may be perceived as burdensome to the physician.

In addition to problems associated with collecting and memorializing treatment and results data sets, there are problems with digesting or consuming recorded data to generate useful conclusions. For instance, recorded mental disorder (e.g., depression state) treatment and results data is often incomplete. In most cases physicians are not researchers and they do not follow clearly defined research techniques that enforce tracking of all aspects of depression states, treatments and results. As a result, data that is recorded is often missing key information such as, for instance, specific patient conditions that may be of current or future interest, reasons why a specific treatment was selected and other treatments were rejected, specific results, etc. In many cases where cause and effect relationships exist between depression state factors and treatment results, if a physician fails to identify and record a causal factor, the results cannot be tied to existing cause and effect data sets and therefore simply cannot be consumed and added to the overall depression knowledge data set in a meaningful way.

Another impediment to digesting collected data is that physicians often capture mental disorder (e.g., depression state), treatment and results data in forms that make it difficult if not impossible to process the collected information so that the data can be normalized and used with other data from similar patient treatments to identify more nuanced insights and to draw more robust conclusions. For instance, many physicians prefer to use pen and paper to track patient care and/or use personal shorthand or abbreviations for different depression state descriptions, patient conditions, treatments, results and even conclusions. Using software to glean accurate information from hand written notes is difficult at best and the task is exacerbated when hand written records include personal abbreviations and shorthand representations of information that software simply cannot identify with the physician's intended meaning.

To be useful, the mental disorder, treatment, and results data and conclusions based thereon have to be rendered accessible to physicians, researchers and other interested parties. For example, in the case of depression treatments where depression states, treatments, results and conclusions are extremely complicated and nuanced, physician and researcher interfaces have to present massive amounts of information and show many data corollaries and relationships. When massive amounts of information are presented via an interface, interfaces often become extremely complex and intimidating, which can result in misunderstanding and underutilization.

Although treatments for many mental disorders, such as depression, exist, they are overwhelmingly directed towards alleviating and treating symptoms as opposed to "curing"

the disorder. With no proven best or even somewhat effica-cious treatment option to choose from, in many cases, physicians turn to clinical trials.

By way of example, depression research is progressing all the time at many hospitals and research institutions where clinical trials are always being performed to test new medi-cations and treatment plans. A depression patient without other effective treatment options can opt to participate in a clinical trial if the patient's depression state meets trial requirements and if the trial is not yet fully enrolled (for example, there is often a limit to the number of patients that can participate in a trial).

At any time there are several thousand clinical trials progressing around the world, and identifying trial options for specific patients can be a daunting endeavor. Matching a patient mental disorder, such as depression state, to a subset of ongoing trials is complicated and time consuming. Paring down matching trials to a best match given location, patient and physician requirements and other factors exacerbates the task of considering trial participation. In addition, consid-ering whether or not to recommend a clinical trial to a specific patient given the possibility of trial treatment effi-cacy where the treatments are by their very nature experi-mental, especially in light of specific patient conditions, is a daunting activity that most physicians do not take lightly.

One other problem with current depression treatment planning processes is that it is difficult to integrate new pertinent treatment factors, treatment efficacy data and insights into existing planning databases. In this regard, known treatment planning databases have been developed with a predefined set of factors and insights and changing those databases often requires a substantial effort on the part of a software engineer to accommodate and integrate the new factors or insights in a meaningful way where those factors and insights are correctly correlated with other known factors and insights. In some cases the required substantial effort simply means that the new factor or insight will not be captured in the database or used to affect planning while in other cases the effort means that the new factor or insight is only added to the system at some delayed time required to apply the effort.

One other problem with existing depression treatment efficacy databases and systems is that they are simply incapable of optimally supporting different types of system users. To this end, data access, views and interfaces needed for optimal use are often dependent upon what a system user is using the system for. For instance, physicians often want treatment options, results and efficacy data distilled down to simple recommendations while a researcher often requires much more detailed data access to develop new hypothesis related to depression state, treatment and efficacy relation-ships. In known systems, data access, views and interfaces are often developed with one consuming client in mind such as, for instance, psychiatrists, general practitioners, radiolo-gists, a treatment researcher, etc., and are therefore opti-mized for that specific system user type which means that the system is not optimized for other user types.

Pharmacogenomics is the study of the role of the human genome in drug response. Aptly named by combining phar-macology and genomics, pharmacogenomics analyzes how the genetic makeup of an individual affects their response to drugs. It deals with the influence of genetic variation on drug response in patients by correlating gene expression pharma-cokinetics (drug absorption, distribution, metabolism, and elimination) and pharmacodynamics (effects mediated through a drug's biological targets). Although both terms relate to drug response based on genetic influences, pharmacogenetics focuses on single drug-gene interactions, while pharmacogenomics encompasses a more genome-wide association approach, incorporating genomics and epi-genetics while dealing with the effects of multiple genes on drug response. One aim of pharmacogenomics is to develop rational means to optimize drug therapy, with respect to the patients' genotype, to ensure maximum efficiency with minimal adverse effects. Pharmacogenomics and pharmaco-genetics may be used interchangeably throughout the dis-closure.

The human genome consists of twenty-three pairs of chromosomes, each containing between 46 million and 250 million base pairs (for a total of approximately 3 billion base pairs), each base pair having complementary nucleotides (the pairing that is commonly described with a double helix). For each chromosome, the location of a base pair may be referred to by its locus, or index number for the base pair in that chromosome. Typically, each person receives one copy of a chromosome from their mother and the other copy from their father.

Conventional approaches to bring pharmacogenomics into precision medicine for the treatment, diagnosis, and analysis of mental disorders such as depression include the use of single nucleotide polymorphism (SNP) genotyping and detection methods (such as through the use of a SNP chip). SNPs are one of the most common types of genetic variation. A SNP is a genetic variant that only spans a single base pair at a specific locus. When individuals do not have the same nucleotide at a particular locus, a SNP may be defined for that locus. SNPs are the most common type of genetic variation among people. Each SNP represents a difference of a single DNA building block. For example, a SNP may describe the replacement of the nucleotide cyto-sine (C) with the nucleotide thymine (T) at a locus.

Furthermore, different nucleotides may exist at the same locus within an individual. A person may have one nucleo-tide in a first copy of a particular chromosome and a distinct nucleotide in the second copy of that chromosome, at the same locus. For instance, loci in a person's first copy of a chromosome may have this nucleotide sequence-AAGCCTA, and the second copy may have this nucleotide sequence at the same loci-AAGCTTA. In other words, either C or T may be present at the 5th nucleotide position in that sequence. A person's genotype at that locus can be described as a list of the nucleotides present at each copy of the chromosome, at that locus. SNPs with two nucleotide options typically have three possible genotypes (a pair of matching nucleotides of the first type, one of each type of nucleotide, and a pair of matching nucleotides of the second type—AA, AB, and BB). In the example above, the three genotypes would be CC, CT, and TT. In a further example, at locus 68,737,131 the rs16260 variant is defined for gene CDH1 (in chromosome 16) where (C; C) is the normal genotype where C is expected at that locus, and (A; A) and (A; C) are variations of the normal genotype.

While SNPs occur normally throughout a person's DNA, they occur almost once in every 1,000 nucleotides on average, which means there are roughly 4 to 5 million SNPs in a person's genome. There have been more than 100 million SNPs detected in populations around the world. Most commonly, these variations are found in the DNA between genes (regions of DNA known as "introns"), where they can act as biological markers, helping scientists locate genes that are associated with disease (such as mental disorders).

SNPs are not the only genetic variant possible in the human genome. Any deviation in a person's genome sequences when compared to normal, reference genome sequences may be referred to as a variant. In some cases, a person's physical health can be affected by a single variant, but in other cases it is only affected by a combination of certain variants located on the same chromosome. When variants in a gene are located on the same chromosome, the variants are in the same allele of the gene. An allele may be defined as a continuous sequence of a region of a DNA molecule that has been observed in an individual organism, especially when the sequence of that region has been shown to have variations among individuals. When certain genetic tests, like NGS, detect more than one variant in a gene, it is possible to know whether those variants are in the same allele. Some genetic tests do not have this capability.

Certain groups of variants that exist together in the same chromosome may form a specific allele that is known to alter a person's health. Occasionally, a single allele may not affect a person's health, unless that person also has a specific combination of alleles. Sometimes an allele or allele combination is reported or published in a database or other record with its health implications (for instance, that having the allele or allele combination causes a person to be an ultrafast metabolizer; intermediate metabolizer; or poor metabolizer; etc.). Exemplary records include those from the American College of Medical Genetics and Genomics (ACMG), the Association for Molecular Pathology (AMP), or the Clinical Pharmacogenetics Implementation Consortium (CPIC). These published alleles may each have a designated identifier, and one category of identifiers is the * (star) allele system. For example, for each gene, each star allele may be numbered *1, *2, *3, etc., where *1 is generally the reference or normal allele. As an example, the CYP2D6 gene has over 100 reported variant alleles.

Developed before Next Generation Sequencing (NGS), microarray assays have been a common genetic test for detecting variants. Microarray assays use biochips with DNA probes bound to the biochip surface (usually in a grid pattern). Mass arrays can also be used in genetic testing. Some of these biochips are called SNP chips. A solution with DNA molecules from one or more biological samples is introduced to the biochip surface. Each DNA molecule from a sample has a fluorescent dye or another type of dye attached. Often the color of the dye is specific to the sample, and this allows the assay to distinguish between two samples if multiple samples are introduced to the biochip surface at the same time.

If the solution contains a DNA sequence that is complementary to one of the probes affixed to the biochip, the DNA sequence will bind to the probe. After all unbound DNA molecules are washed away, any sample DNA bound to the probe will fluoresce or create another visually detectable signal. The location and sequence of each probe is known, so the location of the visually detectable signal indicates what bound, complementary DNA sequence was present in the samples and the color of the dye indicates from which sample the DNA sequence originated. The probe sequences on the biochip each only contain one sequence, and the probes bind specifically to one complementary sequence in the DNA, meaning that most probes can only detect one type of mutation or genetic variant. This also means that a microarray will not detect a sequence that is not targeted by the probes on the biochip. It cannot be used to find new variants. This is one reason that next generation sequencing is more useful than microarrays.

The fact that a probe only detects one specific DNA sequence means that the microarray cannot determine whether two detected variants are in the same allele unless the loci of the variants are close enough that a single probe can span both loci. In other words, the number of nucleotides between the two variants plus the number of nucleotides within each variant must be smaller than the number of nucleotides in the probe otherwise the microarray cannot detect whether two variants are in the same DNA strand, which means they are in the same allele.

Also, each probe will bind to its complementary sequence within a unique temperature range and range of concentrations of components in the DNA solution introduced to each biochip. Because it is difficult to simultaneously achieve optimal binding conditions for all probes on a microarray (such as the microarrays used in SNP Chips), any DNA from a sample has the potential to hybridize to probes that are not perfectly complementary to the sample DNA sequence and cause inaccurate test results.

Furthermore, disadvantages of microarrays include the limited number of probes present to target biomarkers due to the surface area of the biochip, the misclassification of variants that do not bind to probes as a normal genotype, and the overall misclassification of the genotype of the patient. Due to the limited processing efficiency of SNP chips, conventional microarray approaches are inefficient in detecting biomarkers and their many included variations.

Taqman assays have limitations similar to those of microarrays. If a taqman assay probe is an exact match for a complementary sequence in a DNA molecule from a sample, the DNA molecule gets extended, similar to NGS. However, instead of reporting what the sequence of each nucleotide type is in the DNA extension, the assay only reports whether extension occurred or not. This leads to the same limitations as SNP chips. Other genetic tests, such as dot blots and southern blots, have similar limitations.

Accordingly there is a need in the art to address the shortcomings described above. With respect to psychiatric disorders such as depression, in many cases, patient conditions related to the disorder may be gleaned from clinical medical records, via a medical examination, genetic analysis, and/or via a patient interview, and may be used to develop a personalized treatment plan for a specific ailment. Thus, there is a need in the art for a system to collect data on as many factors as possible that have any cause-effect relationship with treatment results and use those factors to design optimal personalized treatment plans.

In addition, what is needed are well designed interfaces that make complex data sets simple to understand and digest. For instance, in the case of mental disorders such as depression states, treatments, and results, it would be useful to provide interfaces that enable physicians to consider de-identified patient data for many patients where the data is specifically arranged to trigger important treatment and results insights. It would also be useful if interfaces had interactive aspects so that the physicians could use filters to access different treatment and results data sets, again, to trigger different insights, to explore anomalies in data sets, and to better think out treatment plans for their own specific patients.

Also, it would be advantageous to have a tool that could help physicians identify clinical trial options for specific patients with specific psychiatric disorder, such as specific depression states and to access information associated with trial options.

Thus, what is needed is a system that is capable of efficiently capturing all treatment relevant data including factors relevant to the psychiatric disorder, for example, depression state factors, treatment decisions, treatment efficacy and exploratory factors (such as factors that may have a causal relationship to treatment efficacy) and structuring that data to optimally drive different system activities including memorialization of data and treatment decisions, database analytics and user applications and interfaces. In addition, the system should be highly and rapidly adaptable so that it can be modified to absorb new data types and new treatment and research insights as well as to enable development of new user applications and interfaces optimized to specific user activities.

BRIEF SUMMARY OF THE DISCLOSURE

One implementation of the present disclosure is a system for personalized psychiatric disorder treatment. In one embodiment, the psychiatric disorder is a depression disorder. The system includes a server configured to communicate with existing healthcare resources and to receive patient data corresponding to a patient, the server including an analytics module. The system further includes a first database configured to store empirical patient outcomes, and further configured to communicate with the analytics module. Additionally, the system includes a user device having a graphical user interface (GUI) configured to communicate with the server and to display at least one output generated by the analytics module. The analytics module is configured to determine at least one of a personalized depression treatment and a personalized depression state prediction based on the empirical patient outcomes and the patient data.

Another implementation of the present disclosure is a method for analyzing clinical data. The method includes combining molecular data with clinical data from a patient diagnosed with a psychiatric illness, to generate combined patient data. The method further includes comparing the combined patient data to a knowledge database to generate information. Additionally, the method includes generating a clinical report with information that relates to the comparison, and providing the clinical report to a physician.

Another implementation of the present disclosure is a method including receiving a list of clinical trial criteria from one or more clinical trials directed to psychiatric disorders, such as depression clinical trials, and receiving patient data from a patient's medical record from an electronic health record system. The method further includes deriving one or more patient metrics, each patient metric corresponding to a clinical trial criteria from the list of clinical trial criteria. Additionally, the method includes comparing each patient metric to the list of clinical trial criteria, and indicating the patient qualifies for one or more of the clinical trials if each criteria of the corresponding list of clinical trial criteria is met.

In one aspect, the present disclosure provides a method for generating treatment information for a patient diagnosed with at least one psychiatric illness. The method includes, at a computer system having one or more processors, and memory storing one or more programs for execution by the one or more processors, obtaining molecular data from a multi-gene panel sequencing reaction upon a sample from the patient, the molecular data including a plurality of nucleic acid sequences obtained from whole exome sequence data, mass array data, sequence data from one or more introns, the introns being associated with metabolic genes, and sequence data from one or more promoter regions, the promoter regions being associated with the metabolic genes, aligning the molecular data to a human reference sequence, providing a first set of clinical data associated with the patient, the first set of clinical data including a listing of prior medications and a listing of the one or more diagnoses, generating a first report from a therapy engine based on the molecular data and the first set of clinical data, the report providing, for each one of at least a portion of the plurality of nucleic acid sequences in the patent molecular data, in a laboratory results section of the report, a phenotype associated with the nucleic acid sequence, and in a supplemental section of the report, a listing of one or more drugs associated with the nucleic acid sequence and a classification for each drug in the listing. the listing of the one or more drugs being determined at least in part by the listing of prior medications, the method further including causing the report to be presented to a user, obtaining a second set of clinical data associated with the patient, the second set of clinical data describing clinical activity of the patient subsequent to presentation of the report, and updating the therapy engine with at least a portion of the second set of clinical data.

In some embodiments, the classification can relate to one or more of drug dosing, drug risks, and contraindications.

In some embodiments, the clinical activity described in the second set of clinical data can include one or more of medication prescribed, dosage of medication, patient compliance, and patient outcome after having taken the prescribed medication.

In some embodiments, the patient can be diagnosed with more than one psychiatric illness.

In some embodiments, the therapy engine can include a knowledge database, the knowledge database including data related to interactions between a specific drug or drugs and one or more nucleic acid sequences associated with drug metabolism, primary drug metabolic pathway data, a first cohort data set derived at time 1 from a cohort of psychiatric subjects, the first cohort data set including drug or drugs used in a treatment, diagnosis before the treatment, treatment outcome, and drug information data collected from one or more of the following sources: scientific publications, Food and Drug Administration (FDA), Clinical Pharmacogenomics Implementation Consortium (CPIC), Dutch Pharmacogenomics Working Group (DPWG), Pharmacogenomics Knowledge Base Review, and Psychoactive drug Screening Program Ki Database.

In some embodiments, the cohort data set may not be derived from clinical trial data. In some embodiments, at least a portion of the psychiatric subjects in the cohort can be diagnosed with more than one psychiatric illness.

In some embodiments, the knowledge database can further include a second cohort data set derived at a time 2, and the second cohort data set can include information from at least one of the first cohort subject. In some embodiments, the knowledge database can further include an Nth cohort data set derived at time N, the Nth cohort data set including information from at least one of previous cohort subject. In some embodiments, the method can further include providing an Nth set of clinical data associated with the patient, and the Nth set of clinical data can be obtained at a time after the (N−1)th clinical data set was obtained. In some embodiments, each of the clinical data sets can describe clinical activity of the patient subsequent to presentation of an immediately previous report. In some embodiments, the method can further include updating the therapy engine with at least a portion of the Nth clinical data set.

In some embodiments, the report can further provide supporting information for the classification. In some embodiments, the report can further provide a hyperlink to a source document or website having information about the drug classification.

In some embodiments, the report can further provide a listing of drugs associated with the patient diagnosis but which have no known nucleic acid associations.

In some embodiments, the clinical activity described in the any of the N clinical data sets can include one or more of medication prescribed, dosage of medication, patient compliance, and patient outcome after having taken the prescribed medication.

In some embodiments, the method can further include generating a second report based on input from the second clinical data set.

In some embodiments, the listing of prior medications can include at least one medication dosage.

In some embodiments, the listing of prior medications can include at least one patient response to a medication.

In some embodiments, the therapy engine can identify a likely side effect of the drug(s) listed and can provide that side effect information on the report.

In some embodiments, the therapy engine can identify a recommended dosage of each drug included in the listing of one or more drugs, and can provide that dosage information on the report.

In some embodiments, the therapy engine can identify a next potential drug recommendation by excluding from the report at least one medication included in the listing of prior medications.

In some embodiments, the therapy engine can include a classifier to identify a sub-type of depression and the psychiatric illness the patient is diagnosed with is depression, and the sub-type of depression can be listed on the report.

In some embodiments, the therapy engine can include a classifier to identify a drug resistance, and the drug resistance can be listed on the report.

In some embodiments, the listing of the one or more drugs can be determined based, at least in part, on at least one diagnosis.

In another aspect, the present disclosure provides a system for generating information about treatment for a patient diagnosed with a psychiatric illness. The system includes at least one memory, and at least one processor coupled to the at least one memory. The system is configured to cause the at least on processor to execute instruction stored in the at least one memory to obtain molecular data from a multi-gene panel sequencing reaction upon a sample from the patient, the molecular data including a plurality of nucleic acid sequences obtained from whole exome sequence data, mass array data, sequence data from one or more introns, the introns being associated with metabolic genes, and sequence data from one or more promoter regions, the promoter regions being associated with the metabolic genes, align the molecular data to a human reference sequence, provide a first set of clinical data associated with the patient, the first set of clinical data including a listing of prior medications and a listing of the one or more diagnoses, generate a first report from a therapy engine based on the molecular data and the first set of clinical data, the report providing, for each one of at least a portion of the plurality of nucleic acid sequences in the patent molecular data, a phenotype associated with the nucleic acid sequence, a listing of one or more drugs associated with the nucleic acid sequence, a classification for each drug in the listing, the listing of the one or more drugs being determined at least in part by the listing of prior medications, cause the report to be presented to a user, obtain a second set of clinical data associated with the patient, the second set of clinical data describing clinical activity of the patient subsequent to presentation of the report, and update the therapy engine with at least a portion of the second set of clinical data.

In some embodiments, the clinical activity described in the second set of clinical data can include one or more of medication prescribed, dosage of medication, patient compliance, and patient outcome after having taken the prescribed medication.

In some embodiments, the cohort data set may not be derived from clinical trial data.

In some embodiments, the subject may be diagnosed with more than one psychiatric illness.

In some embodiments, at least a portion of the psychiatric subjects in the cohort can be diagnosed with more than one psychiatric illness.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE DRAWINGS

FIG. 2 is an image of an example graphical user interface (GUI), according to aspects of the present disclosure;

FIG. 3D is another image of the example GUI of FIG. 2, according to aspects of the present disclosure;

FIG. 4C is another image of the example GUI of FIG. 2, according to aspects of the present disclosure;

FIG. 6E is another image of the example GUI of FIG. 2, according to aspects of the present disclosure;

FIGS. 9A through 9H illustrate an alternative embodiment of a patient report.

FIG. 10 is a portion of another alternative embodiment of a patient report.

FIG. 11 is another portion of the patient report in FIG. 10.

FIG. 12 is yet another portion of the patient report in FIG. 10.

FIG. 13 is an additional portion of the patient report in FIG. 10.

FIG. 14 is a further portion of the patient report in FIG. 10.

FIG. 15 is a still further portion of the patient report in FIG. 10.

FIG. 16 is another additional portion of the patient report in FIG. 10.

FIG. 17 is yet another additional portion of the patient report in FIG. 10.

FIG. 18 is still another additional portion of the patient report in FIG. 10.

Figure 1:
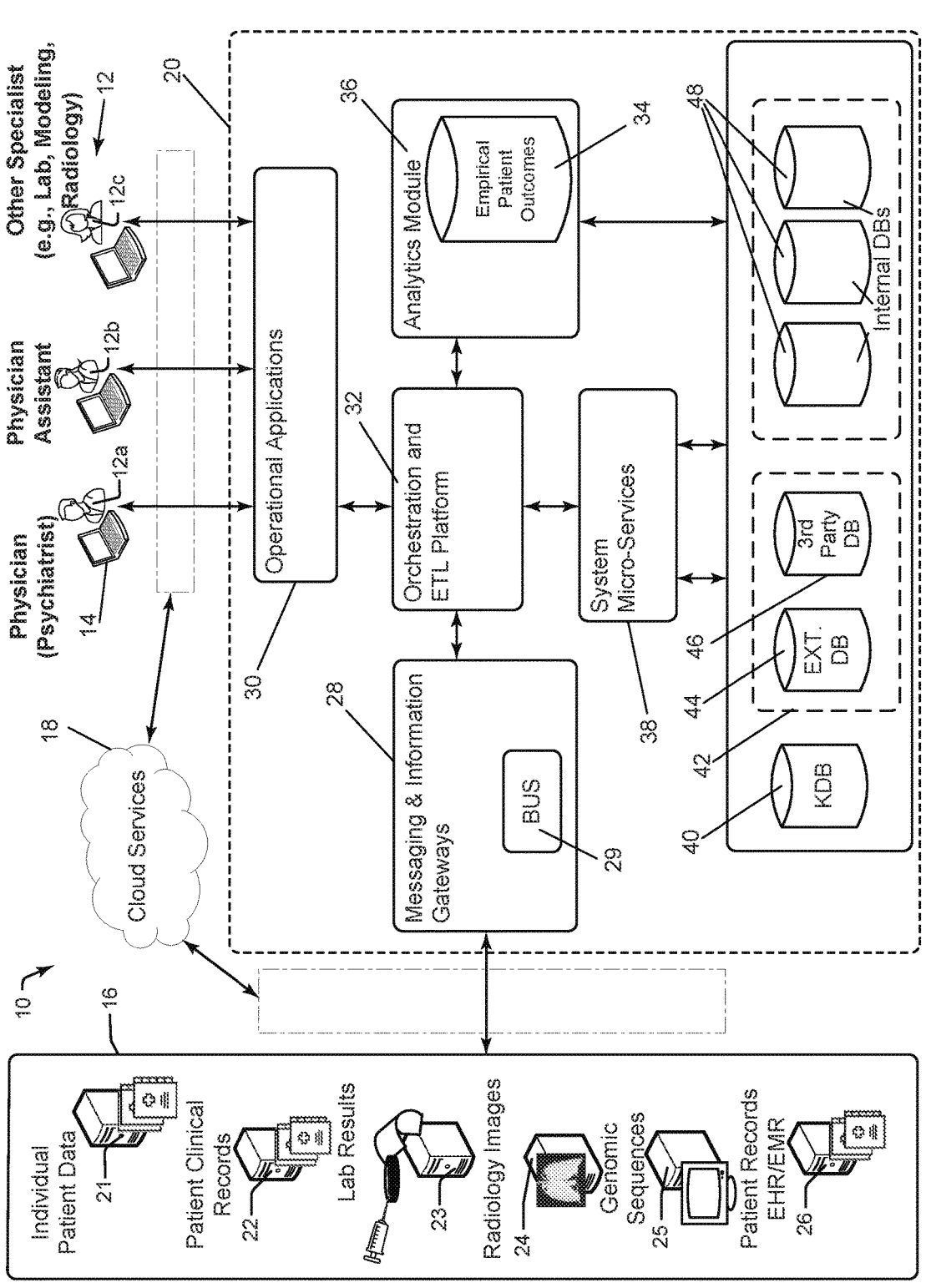
FIG. 1 is a block diagram of a data-based treatment system, according to aspects of the present disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE
DISCLOSURE

The various aspects of the subject invention are now described with reference to the annexed drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

The present disclosure is described in the context of a system related to psychiatric disorders (such as depression, bipolar disorder, obsessive compulsive disorder, borderline personality disorder, anxiety, etc.) research, diagnosis, treatment and results analysis. More specifically, an example embodiment related to depressive disorder ("depression") is described herein. Nevertheless, it should be appreciated that the present disclosure is intended to teach concepts, features and aspects that will be useful in many different health related contexts and therefore the specification should not be considered limited to depression-related systems unless specifically indicated for some system aspect. Furthermore, the present disclosure is described in the context of a system related to the research, diagnosis, treatment and analysis of results from next generation sequencing (NGS).

Hereafter, unless indicated otherwise, the following terms and phrases will be used in this disclosure as described. The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, data abstractors, neurologists, psychiatrists, data scientists, and many other persons with specialized skill sets.

The term "physician" will be used to refer generally to any health care provider including but not limited to a primary care physician, a medical specialist, a neurologist, a psychiatrist, a psychologist, a nurse, and a medical assistant, among others.

The term "researcher" will be used to refer generally to any person that performs research including but not limited to a radiologist, a neurologist, a data scientist, or some other health care provider. One person may be both a physician and a researcher while others may simply operate in one of those capacities.

The phrase "system specialist" will be used generally to refer to any provider employee that operates within the disclosed systems to collect, develop, analyze or otherwise process system data, tissue samples or other information types (such as medical images) to generate any intermediate system work product or final work product where intermediate work product includes any data set, conclusions, tissue or other samples, or other information for consumption by one or more other system specialists and where final work product includes data, conclusions or other information that is placed in a final or conclusory report for a system client or that operates within the system to perform research, to adapt the system to changing needs, data types or client requirements. For instance, the phrase "abstractor specialist" will be used to refer to a person that consumes data available in clinical records provided by a physician (such as primary care physician or psychiatrist) to generate normalized and structured data for use by other system specialists. The phrase "programming specialist" will be used to refer to a person that generates or modifies application program code to accommodate new data types and or clinical insights, etc.

The phrase "system user" will be used generally to refer to any person that uses the disclosed system to access or manipulate system data for any purpose, and therefore will generally include physicians and researchers that work for the provider or that partner with the provider to perform services for patients or for other partner research institutions as well as system specialists that work for the provider.

The phrase "depression state" will be used to refer to a depression patient's overall condition including diagnosed depression, mental and physical depression symptoms, other patient conditions (such as age, gender, weight, race, habits (such as smoking, drinking, diet)), other pertinent medical conditions (such as anxiety, high blood pressure, dry skin, other diseases, etc.), medications, allergies, other pertinent medical history, current side effects of any depression treatments and other medications, etc.

The term "consume" will be used to refer to any type of consideration, use, modification, or other activity related to any type of system data, saliva samples, etc., whether or not that consumption is exhaustive (such as used only once, as in the case of a saliva sample that cannot be reproduced) or inexhaustible so that the data, sample, etc., persists for consumption by multiple entities (such as used multiple times as in the case of a simple data value). The term "consumer" will be used to refer to any system entity that consumes any system data, samples, or other information in any way including each of specialists, physicians, researchers, clients that consume any system work product, and software application programs or operational code that automatically consume data, samples, information or other system work product independent of any initiating human activity.

The phrase "treatment planning process" will be used to refer to an overall process that includes one or more subprocesses that process clinical and other patient data and samples (such as saliva samples) to generate intermediate data deliverables and eventually final work product in the form of one or more final reports provided to system clients. These processes typically include varying levels of exploration of treatment options for a patient's specific depression state but are typically related to treatment of a specific patient as opposed to more general exploration for the purpose of more general research activities. Thus, treatment planning may include data generation and processes used to generate that data, consideration of different treatment options and effects of those options on patient condition, etc., resulting in ultimate prescriptive plans for addressing specific patient ailments.

Medical treatment prescriptions or plans are typically based on an understanding of how treatments affect illness (such as treatment results) including how well specific treatments eradicate illness, duration of specific treatments, duration of healing processes associated with specific treatments and typical treatment-specific side effects. Ideally, treatments result in complete elimination of an illness in a short period with minimal or no adverse side effects. In some cases, cost is also a consideration when selecting specific medical treatments for specific ailments.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer-readable media can include but are not limited to magnetic storage devices (such as hard disk, floppy disk, magnetic strips), optical disks (such as compact disk (CD), digital versatile disk (DVD)), smart cards, and flash memory devices (such as card, stick). Additionally it should be appreciated that a carrier wave can be employed to carry computer-readable electronic data such as those used in transmitting and receiving electronic mail or in accessing a network such as the Internet or a local area network (LAN). Transitory computer-readable media (carrier wave and signal based) should be considered separately from non-transitory computer-readable media such as those described above. Of course, those skilled in the art will recognize many modifications may be made to this configuration without departing from the scope or spirit of the claimed subject matter.

Unless indicated otherwise, while the disclosed system is used for many different purposes (such as data collection, data analysis, data display, treatment, research, etc.), in the interest of simplicity and consistency, the overall disclosed system will be referred to hereinafter as "the disclosed system".

As used herein, the term "clinical data" refers to information related to a patient or a cohort subject that is typically obtained by questioning the subject, observing the subject, or testing the subject. Exemplary clinical data include, but are not limited to physical characteristic (e.g., sex, height, weight, age, overall health, etc.), medical history, current and past diagnosis, current and past treatment regimens administered, patient compliance, treatment outcomes, imaging analysis such as x-rays, CT-scans, facial imaging, and body movement recordings, physician observations and notes regarding behavior, thought patterns, sleep cycles, physical conditions, changes, etc.

In one example, the invention disclosed here may be a system, other class of device, and/or method to help a medical provider make clinical decisions based on a combination of molecular and clinical data, which may include comparing the molecular and clinical data of a patient to an aggregated data set of molecular and/or clinical data from multiple patients (e.g., a cohort of subjects) and/or a knowledge database (KDB) of clinicogenomic data. Additionally, the invention disclosed here may be used to capture, ingest, cleanse, structure, and combine robust clinical data and detailed molecular data to determine the significance of correlations, patterns and trends to generate reports for physicians, analyze or confirm the accuracy of a diagnosis, predict the likelihood that a patient responds to a specific treatment, recommend or discourage specific treatments for a patient, support biomarker discovery, bolster clinical research efforts, monitor treatment and dosing decisions, expand indications of use for treatments currently in market and clinical trials, and expedite federal or regulatory body approval of treatment compounds. In one example, the invention disclosed here may help academic medical centers, pharmaceutical companies and community providers improve care options and treatment outcomes for patients, especially patients experiencing any psychiatric disorders or illnesses, including, but not limited to Treatment Resistant Depression, Major Depressive Disorder, Bipolar Disorder, Schizophrenia, etc. In one example, one implementation of this system may be a form of software.

As used herein, "drug metabolism" refers to the metabolic breakdown of drugs by living organism, usually through specialized enzyme systems. Genes encoding such enzymes, or genes encoding regulators of the enzyme-expressing genes are considered drug metabolic genes.

The terms "subject" and "patient" are used interchangeably herein. The subject is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Further, a "subject" can include a patient diagnosed with or suspected of having a condition or disease, such as a psychiatric illness.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness such as a psychiatric illness, e.g., the pattern of dosing or other treatments (e.g., counseling, group therapy, etc.), used during therapy.

As used herein, the terms "control," "control sample," "reference," "reference sample," "normal," and "normal sample" describe a sample from a non-diseased tissue. In some embodiments, such a sample is from a subject that does not have a particular condition (e.g., diagnosed psychiatric disorder). In other embodiments, such a sample is an internal control from a subject, e.g., who may or may not have the particular disease or disorder, and is from a pre-treatment sample from the subject. For example, where a blood or saliva sample is obtained from a subject diagnosed with one or more psychiatric disorders, an internal control sample may be obtained from the subject prior to any treatment. The pre-treatment sample may show, for example and elevated level of expression from one or more genes. After treatment, another sample may be analyzed, to determine whether the treatment alters expression levels. Accordingly, a reference sample can be obtained from the subject or from a database, e.g., from a second subject.

As used herein "molecular data" includes information such as the sequence and/or amount (e.g., expression level, or duplication/deletion information) of one or more proteins, DNA, or RNA samples of a subject, a control subject, or a cohort. By way of example but not by way of limitation, in some embodiments, molecular data includes DNA sequence information including but not limited to whole exome genetic data, single nucleotide variants (SNV), insertion/deletions (indels), copy number variation (CNV), fusion variants, RNA expression data (including miRNA expression), microbiome information, haplotypes or alleles information including star alleles, haplotype groups or diplotypes including star allele combinations, mass array data, microarray data. Whole exome genetic data pertaining to any of the exons in the human genome may further include intronic regions targeted, for example, by intron-specific probes spiked into a whole exome panel. Molecular data as used herein also includes targeted panels of DNA or RNA data (including sequence data and/or expression level data), and targeted panels of protein data. By way of example but not by way of limitation, a targeted panel includes an assay designed for evaluating or analyzing only specific genetic sequences such as specific genes, parts of genes, or specific non-coding sequences (e.g., introns or promoter regions), or specific proteins, as opposed to whole genome RNA analysis for example. Molecular data may be obtained by methods well known in the art; such methods are not intended to be limiting. By way of example, in some embodiments, molecular data is derived from a multi-gene panel sequencing reaction, and comprises a plurality of nucleic sequences obtained from one or more of whole exome sequence data, mass array data, sequenced data from one or more introns, and sequence data from one or more gene regulatory regions.

For example, the methods and systems described herein may be used on information generated from next generation sequencing (NGS) techniques. The field of NGS for genomics is new and faces significant challenges in managing relations between sequencing, bioinformatics, variant calling, analysis, and reporting data. NGS involves using specialized equipment such as a next generation gene sequencer, which is an automated instrument that determines the order of nucleotides in DNA and RNA. The instrument reports the sequences as a string of letters, called a read, which the analyst may compare to one or more reference genomes of the same genes. A reference genome may be compared to a library of normal and variant gene sequences associated with certain conditions. With no settled NGS standards, different NGS data providers and laboratories have different approaches for sequencing patient genomes; and, based on their sequencing approaches, generate different types and quantities of genomics data to share with physicians, researchers, and patients. Different genomic datasets exacerbate the task of discerning, and in some cases render it impossible to discern, meaningful genetics-treatment efficacy insights, as required data is not in a normalized form, was never captured, or simply was never generated. The systems and methods disclosed herein address this deficiency.

In one exemplary embodiment, extracted DNA from blood, saliva, biopsy, or other biological patient samples are single- or paired-end sequenced using an NGS platform, such as a platform offered by Illumina. The patient from whom the sample was collected may have been diagnosed with a psychiatric illness. The results of sequencing (herein, the "raw sequencing data") may be passed through a bioinformatics pipeline where the raw sequencing data is analyzed. The raw sequencing data may pertain to a combination of every exon and selected introns in the human genome. After sequencing information is run through the bioinformatics pipeline, it may be evaluated for quality control, such as through an automated quality control system. If the sample does not pass an initial quality control step, it may be manually reviewed. If the sample passes an automated quality control system or is manually passed, an alert may be published to a message bus that is configured to listen for messages from quality control systems. This message may contain sample identifiers, as well as the location of BAM files. A BAM file (.bam) is the binary version of a SAM file. A SAM file (.sam) is a tab-delimited text file that contains sequence alignment data (such as the raw sequencing data). When a message is received, a service may be triggered to evaluate the sequencing data for pharmacogenomics factors.

As used herein, the term "BAM File" or "Binary file containing Alignment Maps" refers to a file storing sequencing data aligned to a reference sequence (e.g., a reference genome or exome). In some embodiments, a BAM file is a compressed binary version of a SAM (Sequence Alignment Map) file that includes, for each of a plurality of unique sequence reads, an identifier for the sequence read, information about the nucleotide sequence, information about the alignment of the sequence to a reference sequence, and optionally metrics relating to the quality of the sequence read and/or the quality of the sequence alignment. While BAM files generally relate to files having a particular format, for simplicity they are used herein to simply refer to a file, of any format, containing information about a sequence alignment, unless specifically stated otherwise.

BAM files can be generated by aligning raw molecular data to a reference genome. For example, raw molecular data can be stored in BCL, FASTA, and/or FASTQ file formats. A suitable process can align the raw molecular data to a human reference sequence and generate aligned sequence reads. The aligned sequence reads can be stored in SAM and/or BAM file formats.

The bioinformatics pipeline may receive the raw sequencing results and process them to identify genetic variants that are expressed in the patient's DNA or RNA and may store this information in a variant call format file (.vcf). An identified variant may be referred to as a variant call. Once a variant has a sufficient number of reads from the raw sequencing results to qualify as a variant call, a variant characterization may be performed on that variant call. In one example, variant characterization is the process of determining whether the variant is benign, linked to increased risk of a certain disease, and/or likely to cause an interaction with a prescribed drug. Variant characterization may include searching published variant datasets identifying variants of pharmacogenomic importance, searching FDA publications on therapies and their targeted variants, or comparing the variant calls to an internally curated list of variants having pharmacogenomic importance. Any variant calls with pharmacogenomic importance may be flagged for inclusion in a report, such as the reports described in more detail below.

As used herein, the term "sequencing probe" refers to a molecule that binds to a nucleic acid with affinity that is based on the expected nucleotide sequence of the RNA or DNA present at that locus.

As used herein, the term "targeted panel" or "targeted gene panel" refers to a combination of probes for sequencing (e.g., by next-generation sequencing) nucleic acids present in a biological sample from a subject (e.g., a saliva or a blood sample), selected to map to one or more loci of interest on one or more chromosomes. In some embodiments, loci are informative for psychological disorder diagnosis and/or drug metabolism information.

As used herein, the term, "reference exome" refers to any sequenced or otherwise characterized exome, whether partial or complete, of any tissue from any organism or pathogen that may be used to reference identified sequences from a subject. Typically, a reference exome will be derived from a subject of the same species as the subject whose sequences are being evaluated. Example reference exomes used for human subjects as well as many other organisms are provided in the on-line genome browser hosted by the National Center for Biotechnology Information ("NCBI"). An "exome" refers to the complete transcriptional profile of an organism or pathogen, expressed in nucleic acid sequences. As used herein, a reference sequence or reference exome often is an assembled or partially assembled exomic sequence from an individual or multiple individuals. In some embodiments, a reference exome is an assembled or partially assembled exomic sequence from one or more human individuals. The reference exome can be viewed as a representative example of a species' set of expressed genes. In some embodiments, a reference exome comprises sequences assigned to chromosomes.

As used herein, the term "reference genome" refers to any sequenced or otherwise characterized genome, whether partial or complete, of any organism or pathogen that may be used to reference identified sequences from a subject. Typically, a reference genome will be derived from a subject of the same species as the subject whose sequences are being evaluated. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38). For a haploid genome, there can be only one nucleotide at each locus. For a diploid genome, heterozygous loci can be identified; each heterozygous locus can have two alleles, where either allele can allow a match for alignment to the locus.

As used herein, the terms "genomic alteration," "mutation," and "variant" refer to a detectable change in the genetic material of one or more cells. A genomic alteration, mutation, or variant can refer to various type of changes in the genetic material of a cell, including changes in the primary genome sequence at single or multiple nucleotide positions, e.g., a single nucleotide variant (SNV), a multi-nucleotide variant (MNV), an indel (e.g., an insertion or deletion of nucleotides), a DNA rearrangement (e.g., an inversion or translocation of a portion of a chromosome or chromosomes), a variation in the copy number of a locus (e.g., an exon, gene, or a large span of a chromosome) (CNV), a partial or complete change in the ploidy of the cell, as well as in changes in the epigenetic information of a genome, such as altered DNA methylation patterns. In some embodiments, a mutation is a change in the genetic information of the cell relative to a particular reference genome, or one or more 'normal' alleles found in the population of the species of the subject. Many loci of a reference genome of a species are associated with several variant alleles that are significantly represented in the population of the subject and are not associated with a diseased state, e.g., such that they would not be considered mutations.

As used herein, the term "pharmacodynamics" refers to the interaction between a genetic polymorphism (or downstream elements such as proteins) and the absorption, distribution, metabolism, and/or excretion properties of a drug or other therapy. A gene associated with metabolization of a particular therapy is referred to as a "metabolic gene". A gene associated with absorption of a particular therapy is referred to as an "absorption gene". A gene associated with distribution of a particular therapy is referred to as a "distribution gene". A gene associated with excretion of a particular therapy is referred to as an "excretion gene."

As used herein, the term "pharmacokinetics" refers to the interaction between a genetic polymorphism (or downstream elements such as proteins) and the receptors, ion channels, enzymes, and immune system associated with a drug or other therapy. A gene associated with immunogenicity is referred to as an "immunogenic gene".

In some embodiments, molecular data comprising sequence data, sometimes termed "sequence reads" may be aligned with or compared to a reference sequence. As used herein, the term "sequence reads" or "reads" refers to nucleotide sequences produced by any nucleic acid sequencing process described herein or known in the art. The sequence reads may be aligned, e.g., using an alignment algorithm, to a reference sequence, e.g., a reference genome, reference exome, or other reference construct prepared for a particular targeted-panel sequencing reaction. For example, in some embodiments, individual sequence reads in electronic form (e.g., in FASTQ files), are aligned against a reference sequence construct for the species of the subject (e.g., a reference human genome) by identifying a sequence in a region of the reference sequence construct that best matches the sequence of nucleotides in the sequence read. In some embodiments, the sequence reads are aligned to a reference exome or reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene. Any of a variety of alignment tools well known in the art can be used for this task. In various embodiments, the alignment or comparison may identify genetic variants and other genetic features, including single nucleotide variants (SNVs), copy number variants (CNVs), gene rearrangements, etc. Methods and algorithms to identify such variants and features are commercially available and are well known in the art.

A knowledge database 40 may be generated for accumulating a cohort of patient molecular data, such as NGS results, and clinical information. The accumulated patient information may be analyzed to identify insights from the information such as potential biomarkers or trends in pharmacogenomics. The knowledge database 40 (KDB) may include treatment implications, diagnostic implications, and prognostic implications. The KDB 40 may include structured data regarding drug-gene interactions, including pharmacogenetic interactions, and precision medicine findings reported in the psychiatric and basic science literature. The KDB 40 may include clinically annotated pharmacogenomic classifications for key pharmacodynamic and pharmacokinetic results related to the treatment of depression and other psychiatric diseases. The KDB 40 of therapeutic and prognostic evidence, which includes therapeutic response and resistance information, may include information from a combination of external sources, which may include sources such as CPIC guidelines, FDA labeling, PharmGKB, Dutch Pharmacogenetics Working Group (DPWG), and/or other proprietary databases or information sources that are either public or available by subscription or upon request, as well as literature sources or novel findings from analyzing a repository of clinical and genetic, genomic, or other-omic information. The KDB 40 may be maintained over time by individuals with experience, education, and training in the relevant field. In some embodiments, clinical actionability entries in the KDB 40 are structured by both (1) the disease and/or the drug-gene interaction to which the evidence applies and (2) the level or strength of evidence.

Therapeutic actionability entries may be binned into tiers of evidence strength by patient disease and/or drug-gene interaction matches as may be established by the professional society guidelines. Evidence-based therapy recommendations may be grouped by their level of evidence strength into tiers, for example, tiers IA, IB, IIC, and IID. Briefly, tier IA evidence may be biomarkers that follow consensus guidelines and match disease type. Tier D3 evidence may be biomarkers that follow clinical research and match disease indication. Tier IIC evidence biomarkers may follow the off-indication use of consensus guidelines or clinical research, or either on- or off-indication patient case studies. Tier HD evidence biomarkers may follow preclinical evidence regardless of disease indication matching. Patients may be matched to actionability entries by gene, specific variant, diagnosis, and level of evidence. Therapeutic options matched to patients may represent recommended therapies and do not reflect whether the patient was prescribed a specific recommendation by their treating physician.

The KDB 40 may contain a data dictionary including clinical data elements, imaging information, molecular data such as but not limited to DNA sequence information, single nucleotide variants (SNV), insertion/deletions (indels), copy number variation (CNV), fusion variants, RNA expression (including miRNA expression), microbiome information, haplotypes or alleles including star alleles, haplotype groups or diplotypes including star allele combinations, phenotype of each haplotype or haplotype group, associated medication, associated risk, associated prognosis, associated diagnostic feature, therapy classification (including standard administration, dose adjustment, contraindication, etc.), incidental germline findings including variants associated with additional health implications, epigenetic values, proteomic values, analyses thereof (such as features extracted from images), and/or combinations of one or more of the data elements or data types included in the KDB 40 (for example, a CYP2D6 gene variant combined with a CYP2C19 gene variant and an associated phenotype, or clinical data matched with molecular and/or image data, aggregated from multiple patient records and analyzed to determine associations among the data types). The KDB 40 may also include behavioral indicators including patient activities or movement patterns and related scores or indicators derived from an image of a patient's face.

The knowledge database 40 may also include other formats of information, such as imaging information. For example, the database may store an image of the patient's face. A module may be used to analyze the image and produce a set of information, also stored in the database, relating to the image. Other images include images developed from MM or CT scans.

The analytic power of NGS stands out above conventional methods of processing genetic variants or alleles which have pharmacogenetic importance. Because the entirety of the normal human genome may be referenced for each of the targeted genes (described in more detail below), NGS may identify previously unobserved variant calls even if the variant was not targeted by the NGS panel. For example, if the normal genome is ATTACCA for a given region of the chromosome, but an untargeted and/or previously undocumented variant exists such that a variant sequence is identified as ATTATCA in that same region, an allele mismatch indicating detection of a new allele spanning that region may be detected merely from the absence of an expected variant call. For example, alleles may be identified from a sequence of nucleotides that match the normal sequence, a sequence of nucleotides that match the sequence of any known allele variation from normal, or by identifying a new sequence which is not a match to any of the known alleles.

Furthermore, because NGS probe reads include the sequence of the DNA molecule that extended from each probe and not just the probe, probe reads from upstream in a DNA molecule which also encompass an untargeted downstream variant may be reported by the NGS sequencer. Confirmed detection of an untargeted variant may be made after analysis in the bioinformatics pipeline, based upon new research or published data. Additionally, sequence coverage over the whole genome allows for research to be performed across aggregated sequencing results and enables the identification of new biomarkers which were previously unknown. An exemplary system that provides a foundation to capture the above benefits, and more, is described below.

System Overview

In one example of the system, which may be used to help a medical provider make clinical decisions based on a combination of molecular and clinical data, the present architecture is designed such that system processes may be compartmentalized into loosely coupled and distinct micro-services for defined subsets of system data, may generate new data products for consumption by other micro-services, including other system resources, and enables maximum system adaptability so that new data types as well as treatment and research insights can be rapidly accommodated. Accordingly, because micro-services operate independently of other system resources to perform defined processes where development constraints relate to system data consumed and data products generated, small autonomous teams of scientists and software engineers can develop new micro-services with minimal system constraints that promote expedited service development.

This system enables rapid changes to existing micro-services as well as development of new micro-services to meet any data handling and analytical needs. For instance, in a case where a new record type is to be ingested into an existing system, a new record ingestion micro-service can be rapidly developed resulting in that addition of a new record in a raw data form to a system database as well as a system alert notifying other system resources that the new record is available for consumption. Here, the intra-micro-service process is independent of all other system processes and therefore can be developed as efficiently and rapidly as possible to achieve the service specific goal. As an alternative, an existing record ingestion micro-service may be modified independent of other system processes to accommodate some aspect of the new record type. The micro-service architecture enables many service development teams to work independently to simultaneously develop many different micro-services so that many aspects of the overall system can be rapidly adapted and improved at the same time.

A messaging gateway may receive data files and messages from micro-services, glean metadata from those files and messages and route those files and messages on to other system components including databases, other micro-services, and various system applications. This enables the micro-services to poll their own messages as well as incoming transmissions (point-to-point) or bus transmissions (broadcast to all listeners on the bus) to identify messages that will start or stop the micro-services.

Referring now to the figures that accompany this written description and more specifically referring to FIG. 1, the present disclosure will be described in the context of an exemplary disclosed system 10 where data is received at a server 20 from many different data sources (such as database 32, clinical record 24, and micro-services (not shown)). In some aspects, the server 20 can store relevant data, such as at database 34, which is shown to include empirical patient outcomes. The server 20 can manipulate and analyze available data in many different ways via an analytics module 36. Further, the analytics module 36 can condition or "shape" the data to generate new interim data or to structure data in different structured formats for consumption by user application programs and to then drive the user application programs to provide user interfaces via any of several different types of user interface devices. While a single server 20 and a single internal database 34 are shown in FIG. 1 in the interest of simplifying this explanation, it should be appreciated that in most cases, the system 10 will include a plurality of distributed servers and databases that are linked via local and/or wide area networks and/or the Internet or some other type of communication infrastructure. An exemplary simplified communication network is labeled 18 in FIG. 1. Network connections can be any type, including hard wired, wireless, etc., and may operate pursuant to any suitable communication protocols. Furthermore, the network connections may include the communication/messaging gateway/bus that enables micro-services file and message transfer according to the above system.

The disclosed system 10 enables many different system clients to securely link to server 20 using various types of computing devices to access system application program interfaces optimized to facilitate specific activities performed by those clients. For instance, in FIG. 1 a provider 12 (such as a physician, researcher, lab technician, etc.) is shown using a display device 16 (such as a laptop computer, a tablet, a smart phone, etc.) to link to server 20. In some aspects, the display device 16 can include other types of personal computing devices, such as, virtual reality headsets, projectors, wearable devices (such as a smart watch, etc.).

In at least some embodiments when a physician, psychiatrist, psychologist, or other mental health professional or provider uses system 10, a physician's user interface (such as on display device 16) is optimally designed to support typical physician activities that the system supports including activities geared toward patient treatment planning. Similarly, when a researcher (such as a radiologist) uses system 10, user interfaces optimally designed to support activities performed by those system clients are provided. In other embodiments, the physician's user interface, software, and one or more servers are implemented within one or more microservices. Additionally, each of the discussed systems and subsystems for implementing the embodiments described below may additionally be prescribed to one or more micro-systems.

System specialists (such as employees that control/maintain overall system 10) also use interface computing devices to link to server 20 to perform various processes and functions. For example, system specialists can include a data abstractor, a data sales specialist, and/or a "general" specialist (such as a "lab, modeling, radiology" specialist). Different specialists will use system 10 to perform many different functions, where each specialist requires specific skill sets needed to perform those functions. For instance, data abstractor specialists are trained to ingest clinical records from various sources (such as clinical record 24) and convert that data to normalized and system optimized structured data sets. A lab specialist is trained to acquire and process patient and/or tissue samples to generate genomic data, grow tissue, treat tissue and generate results. Other specialists are trained to assess treatment efficacy, perform data research to identify new insights of various types and/or to modify the existing system to adapt to new insights, new data types, etc. The system interfaces and tool sets available to provider specialists are optimized for specific needs and tasks performed by those specialists.

Referring again to FIG. 1, server 20 is shown to receive data from several sources. According to some aspects, clinical trial data can be provided to server 20 from database 32. In some embodiments, additionally or alternatively, data can be provided to the server that is not obtained from a clinical trial (e.g., a cohort of subjects). Further, patient data can be provided to server 20. As shown, patient 14 has corresponding data from multiple sources (such as lab results 26 will be furnished from a laboratory or technician, imaging data 28 will be furnished from a radiologist, etc.). For simplicity, this is representatively shown in FIG. 1 as individual patient data 22. In some aspects, individual patient data 22 includes clinical record(s) 24, lab results 26, and/or imaging data 28. In some aspects, clinical record(s) 24 can include therapy notes (for example, notes written by a psychologist, psychiatrist, social worker, counselor, primary care physician/PCP, and/or nurse practitioner). Further, in some aspects, clinical record(s) 24 can include applicable screening results, such as a patient's BDI-II score, PHQ-9 score, customized questionnaires for specific patients, and the like. For instance, the clinical record(s) 24 may include reported scores on the patient's interest or pleasure in doing things; feeling down, depressed, or hopeless; trouble with falling or staying asleep, or sleeping too much; feeling tired or having little energy; poor appetite or overeating; feeling bad about yourself or that you are a failure or have let yourself or your family down; trouble concentrating on things, such as reading the newspaper or watching television; moving or speaking so slowly that other people could have noticed or moving or speaking so quickly that the patient seems fidgety or restless; thoughts that the patient would be better off dead, or of the patient hurting him or herself. These reported scores may be outcomes, symptoms, or observations reported by the clinician, patient, and/or third party including a patient's family members. The clinical record(s) may include longitudinal data, which is data collected at multiple time points during the course of the patient's treatment.

The individual patient data 22 can be provided to server 20 by, for example, a data abstractor specialist (as described above). Alternatively, electronic records can be automatically transferred to server 20 from various facilities, practitioners, or third party applications, where appropriate. As shown in FIG. 1, patient data communicated to server 20 can include, but is not limited to, treatment data (such as current treatment information and resulting data), genetic data (such as RNA, DNA data), brain scans (such as PET scans, CT, Mill, etc.), and/or clinical records (such as biographical information, patient history, patient demographics, family history, comorbidity conditions, therapy notes, etc.).

Still referring to FIG. 1, server 20 is shown to include analytics module 36, which can analyze data from database 34 (empirical patient outcomes), and individual patient data 22. Database 34 can store empirical patient outcomes for a large number of patients suffering from the same or similar mental disorder (such as depression) as patient 14. For example, "individual patient data" for numerous patients can be associated with each respective treatment and treatment outcomes, and subsequently stored in database 34. As new patient data and/or treatment data becomes available, database 34 can be updated. As one example, provider 12 may suggest a specific treatment for patient 14, and individual patient data 22 may then be included in database 34. Clinical and/or molecular data associated with patient 14 and generated after analytics module 36 is used to analyze database 34 and individual patient data 22 may be collected and stored in database 34. For example, provider 12 may suggest a specific treatment for patient 14 and patient 14's response to that specific treatment may be added to database 34, with or without individual patient data 22, (for example, to collect longitudinal patient information in database 34). As shown, the server 20 can include the knowledge database 40, a number of other databases 42 such as an external database 44 and/or a third party database 46, and/or a number of internal databases 48.

Analytics module 36 can, in general, use available data to indicate a diagnosis, predict progression, predict treatment outcomes, and/or suggest or select an optimized treatment plan (such as a medication type, an available clinical trial) based on the specific depression state, clinical data, behavioral data, and/or molecular data of each patient. For example, an indicated diagnosis may suggest that the patient does not have depression. For example, the patient may be more likely to have another diagnosis with similar symptoms, including a bipolar diagnosis or situational depression, or an entirely different health condition, including a thyroid condition that has depressive-like symptoms. In one example, antidepressants may not alleviate depressive-like symptoms caused by a thyroid condition and an indication that a patient may have a thyroid condition may guide a provider to prescribe thyroid treatments to a patient instead of antidepressants.

A diagnosis indication may be based on any portion of individual patient data 22 or aggregated data from multiple patients, including clinical data, behavioral data, and molecular data. In one example, individual patient data 22 is normalized, de-identified, and stored collectively in database 34 to facilitate easy query access to the dataset in aggregate to enable a medical provider to use system 10 to compare patients' data, stratify patients, predict therapeutic outcomes, and generate new hypotheses. For example, system 10 may be used to stratify patients, discover biomarkers of various responses to therapy, and/or find cohorts and subcohorts of patients predicted to respond to a particular therapy in a particular manner. Clinical data may include physician notes, imaging data, and behavioral data and may be generated from clinical records, hospital EMR systems, researchers, patients, and community physician practices. To generate standardized data to support internal precision medicine initiatives, clinical data, including free form text and/or handwritten notes, may be processed and structured into phenotypic, therapeutic, and outcomes or patient response data by methods including open character recognition, natural language processing, and manual curation methods that may check for completeness of data, interpolate missing information, use manual and/or automated quality assurance protocols, and store data in FHIR compliant data structures using industry standard vocabularies for medical providers to access through the system 10. Behavioral data may include patient reported outcomes, wearable fitness tracker data, geographical location data showing trends in patient movement, etc. Molecular data may include variants or other genetic alterations, DNA sequences, RNA sequences and expression levels, miRNA sequences, epigenetic data, protein levels, metabolite levels, etc.

In one example, datasets can be filtered by very specific criteria and may include population filtering, mirroring those of inclusion and exclusion criteria in study designs and clinical trials. These custom subsets can be saved and fed through the analytic modules to generate predictive analytics. These quantitative predictive analytics, including diagnostic and prognostic results from analysis of combined molecular, clinical and imaging data, can be used to stratify patients into more granular and indicative disease subtypes. Understanding how patients relate on a molecular, metabolic and phenotypic level may facilitate discovering new, targetable biomarkers for drug development and expanding indications of use for already approved drugs.

In one example, the system may include visualization and analysis tools that generate clinical and research insights on phenotypic, therapeutic, and outcomes data. These tools allow a medical provider to quickly investigate and visualize clinical and molecular trends in a given patient population. A medical provider may use these tools to analyze the data in semi-supervised and unsupervised manners to define clusters, separations or stratifications among patients based on clinical, molecular, and treatment patterns through a series of interactive learning from the data in aggregate. New insights related to outcomes, subtyping, and prognostic implications are generated by analyzing the molecular and clinical attributes observed in the broader patient population.

In some embodiments, cohorts can be generated using gene weighting and other methods as described in U.S. patent application Ser. No. 16/671,165, filed Oct. 31, 2019, and titled "User Interface, System, and Method For Cohort Analysis, which is fully incorporated herein by reference. The system 10 can process an actionable gene database to explicitly generate an importance for each gene from the evidence for, and the impact of, a mutation, allele, haplotype, diplotype, or predicted phenotype for helping a clinician make a drug choice. Genes not in the actionable gene database have a weight of 0. Conversely, a gene of weight 1 has a highest confidence that it affects the action of an FDA-approved drug for the cancer type in question for that variant. Other factors for adjusting a gene weighting may include evidence of being a driver gene or having an associated drug interaction in the metric and an assessment of DNA variation at the variant level, rather than just at the gene level.

In some embodiments, gene weights may be determined based on evidence that a gene is useful in comparing patients in a cohort. For example, the presence of an approved treatment or recommended treatment adjustment for a specific gene mutation may be used to modify a weighting. In particular, the existence of an FDA-approved drug or a known associated drug interaction for a mutation in a specific gene for a specific drug or psychological disorder may result in the weighting for that gene being increased and/or set to "1." (Such weighting may be both gene specific and psychological disorder—specific, as the same drug may not be approved for a mutation in the same gene for a different psychological disorder, which may result in no change to that gene's weighting in that circumstance.)

In some embodiments, importance scores may be calculated by following a rule set. For example, in one rule set, a base weight of 0 is assigned to all genes. If a gene is not included in a genetic base panel, then the weight remains 0 and the next gene's weight is calculated. If a gene is included in a genetic panel, information is extracted from the panel by starting with an initial gene base weight of 0. Such information may include whether there is an FDA approved therapy targeting the genetic mutation or whether there is a known drug-interaction associated with the genetic mutation. If such a therapy exists, the gene weight may be increased using metric $c_1$. If no such therapy exists, then there may be a determination as to whether the gene allele or allele combination has an evidence for the drug or psychological disorder being queried. As before, if such evidence exists, the gene weight may be increased using metric $c_2$, discussed below. The gene weights then may be increased based on the total level of evidence using a third metric $c_3$. Finally, the gene weight may be re-scaled using a maximum weight of one, e.g., after this procedure has been undertaken for each gene under consideration.

As discussed above, weights may be increased using a metric $c_1$. This metric relies on a level of evidence for the particular gene/therapy combination to increase the weight, where the gene residing low on a spectrum results in a low increase to the weight and residing high on the spectrum results in a high increase to the weight. In particular, there may exist levels of evidence for a therapy adjustment recommendation for a particular gene, e.g, 1 to 7, where 1 is the best and 7 is the least informative. Such levels may be determined based on one or more factors including, e.g., a number of patients that have undertaken the therapy with favorable results, a percentage of patients experiencing milder symptoms after 1 year, 2 years, 5 years, etc., a percentage reflecting an existence or lack of adverse side effects, etc. In another embodiment, the existence of evidence that a gene allele or allele combination has an associated drug interaction increases the gene's weight and a gene allele or allele combination which has no associated drug interactions does not increase the gene's weight.

Similarly, weights may be increased using a metric $c_2$. Like $c_1$, this metric may rely on a level of evidence for the particular gene/drug interaction to increase the weight, where the gene residing low on a spectrum results in a low increase to the weight and residing high on the spectrum results in a high increase to the weight. As with $c_1$, there may exist different levels of evidence for the particular cancer type, where stronger correlations may be reflected in larger values of $c_2$. In another embodiment, the existence of evidence that the gene allele or combination of alleles is correlated with a drug interaction, increases the gene's weight based on the level of correlation and a gene allele or combination of alleles which has no correlation to a drug interaction does not increase the gene's weight.

Other evidence may be weighed. Such evidence may include gene alleles or combinations of alleles which do not have known, established correlations to certain drug interactions but where certain variants of the gene may hold a slight correlation. A varying level of $c_3$ may be applied based on the strength of the correlation of each variant present.

Once the weights $c_1$, $c_2$, and $c_3$ are determined, it is possible that the sum of the weights $c_1+c_2+c_3$ for a gene may be greater than one. Thus, the gene weights can be normalized by dividing each specific c1+c2+c3 gene weight by the sum of the maximum values for each metric, i.e., c1 max+c2 max+c3 max.

In addition to analyzing patients for similarities or commonalities of at least one somatic mutation in common, the DNA metric also may account for when a pair of patients has no mutations in common in order to separate out patients that could nearly be close (if they had had a few key mutations) from patients that are definitely very different.

If two patients have no mutations in common, the metric for that pair may be 0. Conversely, in the event that a pair of patients has at least one mutation in common, the metric may be a sum of the gene importance scores across the mutated genes that they have in common, taking into account the gene weighting discussed above. The use of gene importance scores may lead to a focal point on the very important genes so that the genes that are of background importance are not that influential.

The sum of gene importance scores may be rescaled by the geometric mean of similarity of the pair of patients to themselves. This means that the mutated genes that are not in common are taken into account. For example, a patient that shares one mutation with a reference patient could be deemed to be closer than a second patient with two shared mutations if the second patient has vastly more mutations that the reference patient does not have. In the event that a pair of patients has no mutations in common, the metric may be generated from the sum of the scores of the mutations in the first patient but not the second and the sum of the scores of the mutations in the second patient but not the first. Then, using the determined scores, patients can be grouped into cohorts based on the similarities of the scores for one or more genes.

In some embodiments, cohorts such as smart cohorts can be generated using as described in Ser. No. 16/732,138, filed Dec. 31, 2019, and titled "Method and Process for Predicting and Analyzing Patient Cohort Response, Progression, and Survival," which is fully incorporated herein by reference.

In some embodiments, a prediction model may be developed which facilitates identification of one or more smart cohorts of patients whose disease progression and/or likelihood of survival is substantially different from expectation, for example significantly longer or shorter than would be expected. Information from these cohorts may then be examined to identify one or more primary factors that could potentially contribute to the survival profile of the cohorts. Identification of smart cohorts may be used to provide precision medicine results for a particular patient, aid in the identification of potential areas of interest to target medication research, and/or identification of unexpected potential to expand medication patient targeting.

Cohorts can be generated by molecular type, by therapy type, medication, medication dosage, prior medications, prior therapy outcomes, clinical information, and/or other suitable information.

Exemplary analytics using one or more analytics modules 36 may include one or more therapy engines that can generate reports listing predicted drugs that may be used to effectively treat a patient, predicted effective dosage amounts for one or more drugs, potential drug side effects, and/or other treatment predictions based on patient genetic data and real-world clinical data. The therapy engine can include the knowledge database 40. The knowledge database can include real-world clinical data including a number of gene-drug interaction studies, cohort studies, Food and Drug Administration (FDA) label recommendations, in-vitro studies about gene-drug interactions, information about primary metabolic enzyme, PD, and/or immune-related genes affecting selected neuropsychiatric medications in the context of genes included on a panel, and/or other suitable information about drug-gene interactions. In some embodiments, the report may be divided into two distinct portions: a laboratory results portion, which may include a phenotype associated with a nucleic acid sequence, and a supplemental section, which may include other information for the clinician's review. The supplemental section may, for instance, include a listing of one or more drugs associated with the nucleic acid sequence; a classification for each drug in the listing; a view of clinical characteristics of patients similar to those of the patient for whom the report is generated, such as clinical, phenotypic, genotypic, and/or morphological characteristics, such as those relating to medications prescribed or administered, patient outcomes, and so forth. When delivered in a paper or PDF format, the laboratory results portion may be separated from the supplemental section by being displayed on different pages. When delivered through a portal, the user may have to select a first hyperlink to view the laboratory results and a second hyperlink to view the supplemental information. In other embodiments, the supplemental section may be displayed to the user on the same page or through the same hyperlink, but distinguished through the use of titles, colors, font size, or other image or stylistic features.

The KBD 40 can include information about a number of drugs and the interaction of the drugs with genes. In some embodiments, for a drug to be included in the knowledge database, the drug may be required to include at least one of an indication of use for a psychiatric condition or a black box PGx warning on the drug label. In some embodiments, the knowledge database can include drugs used to treat conditions that the drug is not marked to treat (i.e., off label usage). For off label drug usage, a medical practitioner may need to verify that the drug is suitable for off label usage before including the drug in the knowledge database.

For drugs included in the knowledge database 40, a number of resources about drug effectiveness, drug-gene interactions, and other suitable literature can be curated by a user such as the knowledge database specialist. In some embodiments, the resources can be curated from Clinical Pharmacogenomics Implementation Consortium (CPIC), Dutch Pharmacogenomics Working Group (DPWG), DailyMed Label resources (i.e. FDA), Pharmacogenomics Knowledge Base (PharmGKB), primary literature sources such as PubMed, and/or ancillary resources such as Psychoactive Drug Screening Program (PDSP Ki) Database.

The knowledge database specialist can then generate clinical actionability entries based on the curated resources (e.g., using the system 10 and/or display device 16 in FIG. 1). As described above, clinical actionability entries can be structured by both (1) the disease and/or the drug-gene interaction to which the evidence applies and (2) the level or strength of evidence. In some embodiments, a clinical actionability entry can include a disease, a metabolic gene, a phenotype, one or more alleles, a drug, a drug dosage amount, patient demographic information (e.g., gender, ethnicity, etc.), level of evidence, and/or other suitable clinically actionable parameters. The clinical actionability entries can aid a doctor in treating a patient. For example, the therapy engine can receive patient information including molecular information, a disease diagnosis, and/or patient demographic information, and identify one or more suitable clinical actionability entries based on the patient information.

As described above, the clinical actionability entries may be binned into tiers of evidence strength by patient disease and/or drug-gene interaction matches as may be established by the professional society guidelines. The knowledge database specialist can sort the clinical actionability entries into tiers using the system 10.

The knowledge database specialist can determine what evidence level should be assigned to a given clinical actionability entry based on a list of criteria. In some embodiments, the criteria can include the presence of sufficient evidence to determine that a given enzyme is the primary metabolizing enzyme for a given drug, presence of sufficient evidence to determine the effect of pharmacogenomic variation in the gene on pharmacokinetic parameters of the drug, presence of sufficient evidence to determine the effect of pharmacogenomic variation in the gene on PD parameters of the drug, presence of sufficient evidence to determine the clinical implications of pharmacogenomic variation on the drug (e.g. dosing, efficacy, tolerability, adverse drug events), presence of evidence for the involvement of multiple genes in the metabolism of the drug, whether or not a multi-gene algorithm is likely needed to best approximate the disposition and clinical outcomes of the medication.

The therapy engines may also comprise one or more machine learning algorithms or neural networks. A machine learning algorithm (MLA) or a neural network (NN) may be trained from a training data set. For a depression disease state, an exemplary training data set may include the clinical and molecular details of a patient such as those curated from the Electronic Health Record or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where certain features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, long short term memory networks, or other neural models where the training data set includes a plurality of samples and RNA expression data for each sample. While MLA and neural networks identify distinct approaches to machine learning, the terms may be used interchangeably herein. Thus, a mention of MLA may include a corresponding NN or a mention of NN may include a corresponding MLA.

Training may include identifying common clinical traits or genetic traits that patients of the overall cohort or patient database may exhibit, labeling these traits as they occur in patient records, and training the MLA to identify patterns in the outcomes of patients based on their treatments as well as their clinical and genetic information. Outputs from one or more analytics module 36 can be provided to display device 16 via communication network 18. Further, provider 12 can input additional data via display device 16 (such as a prescribed treatment), and the data can be transmitted to server 20.

Display device 16 can provide a graphical user interface (GUI) for provider 12. The GUI can, in some aspects, be interactive and provide both comprehensive and concise data to provider 12. In some embodiments, provider 12 can include a physician 12a (e.g., a psychiatrist), a physician assistant, and/or another specialist 12c. In some embodiments, the provider 12 can be a knowledge database specialist, as will be described below. As one example, a GUI can include intuitive menu options, selectable features, color and/or highlighting to indicate relative importance of data, and sliding-scale timelines for the viewing of disorder progression. The GUI can be tailored to the type of provider, or even customized for each individual user. For example, a physician can change a default GUI layout based on individual preferences. Additionally, the GUI may be adjusted based on patient information. For example, the order of the display components and/or the components and the information contained in the components may be changed based on the patient's diagnosis.

Further aspects of the disclosed system are described in detail with respect to FIGS. 2-7D. In particular, an interactive GUI that can be displayed on display device 16, is shown and described.

Graphical User Interface

In some aspects, a graphical user interface (GUI) can be included in system 10. A GUI can aid a provider in the prevention, diagnosis, treatment, and planning for patients having a psychiatric disorder and/or illness. Advantageously, the GUI provides a single source of information for providers, while still encompassing all necessary and relevant data. This can ensure efficient and individualized treatment for patients, including those suffering from depression. An exemplary GUI is shown and described with respect to FIGS. 2-7D.

FIG. 2 is a graphical user interface (GUI) 50 that can be implemented in system 10 to provide patient information for depression (or psychiatric disorders or illnesses, including mood disorders, bipolar disorder, schizophrenia, personality disorders, etc.). As shown, a provider can login to the provided platform (such as account name 54). Here, a physician can view a patient summary table 52 that includes a list view of each of his patients. In some aspects, patient summary table 52 includes patient names, attending physician, report type, report date, and status of a test, order, and/or patient. Various report types can be generated for patients. For example, a risk assessment report may include an analysis of patient risk factors (such as family history, genetics, etc.). Alternatively, a diagnostic report may include test results post-treatment, predictions of disorder progression, further subtyping of the patient's disease, identification of a possible misdiagnosis of the patient, prognostic implications, etc. Reports may be based on single data types (for example, DNA reports) or combinations of multiple data types (for example, clinical and molecular data). Patient summary table 52 can include additional data not represented in FIG. 2. As shown, a provider can select an individual patient to view additional information. The corresponding table row can indicate selection via highlighting or other means.

The GUI 50 can provide a secure, centralized, and user-friendly way to receive test status updates and results for your patients. In some embodiments, the GUI 50 can provide services and/or other features including online ordering (e.g., placing a test order electronically and quickly through a HIPAA compliant form), search (e.g., fuzzy search and/or filtering to efficiently find relevant patients and/or groups of patients), order status monitoring (e.g., viewing information about an order including when an order is placed, a when sample is submitted, when processing has begun on the sample, when the testing results are expected to be delivered, and/or when an order is complete), and/or data insights (e.g., supplemental information in addition to molecular information about a patient, the such as patient-reported outcomes (PROs) data to allow a clinician to have a more holistic view of their patients that allows the clinician to make data-driven decisions about their patient's care and treatment.) In some embodiments, the GUI 50 can provide option for physicians to choose the cadence in which they want to collect outcomes from their patients and which assessments to assign to each patient.

The GUI 50 may be presented through a portal, such as a secure and centralized that permits clinicians to receive status updates and results for their patients. The portal may permit a clinician to place a test order electronically, use fuzzy search and/or filtering to look for information on a patient or a group of patients; see when an order is placed, when a sample has been submitted, when processing has begun on the sample, when the clinician can expect testing results, and when an order is complete. Alongside molecular information about a patient, the GUI and/or report may provide patient-reported outcomes (PROs) data to allow a clinician to have a more holistic view of their patients that allows them to make data-driven decisions about their patient's care and treatment. In various embodiments, the physicians may choose the cadence in which they want to collect outcomes from their patients and which assessments to assign to each patient. FIGS. 3A-3D show further aspects of GUI 50. In particular, GUI 50 is shown to display a patient identifier 56 (such as patient name), menu 58, summary portion 60, diagnosis tile 62, and diagnosis timeline 64.

In some aspects, menu 58 can include several selectable options, which are grouped by topic. As shown, "summary" 60 can include diagnosis tile 62, therapies tile 68, molecular overview tile 76, and imaging overview tile 78. Summary portion 60 may further include biographical information, patient history, patient demographics, family history, comorbidity conditions, therapy notes, etc. The "summary" menu option is shown as selected, as indicated by the darkened area within menu 58. As shown by menu 58, "reports" may include molecular and imaging information. Additionally, "interventions" may include therapies and clinical trial information. Further, menu 58 may include an analytics portion. In some aspects, menu 58 can have more (or less) selectable options, and the titles of menu options may differ from the examples shown here.

Diagnosis tile 62 can display a patient's diagnosis (including Major Depressive Disorder or another psychiatric disorder), as well as related information. As shown, for example, diagnosis tile 62 can include the age at diagnosis (such as 22 years). In some aspects, diagnosis tile 62 can include a PHQ-9 score at diagnosis (such as 22: severe), or other diagnostic scoring results, such as a BDI-II score or the Diagnostic and Statistical Manual of Mental Disorders, 5th Edition (DSM-5) diagnostic criteria. Diagnosis tile 62 may further include the date on which the diagnosis was determined, the methods used to generate the diagnosis, and clinical evaluations. As shown, diagnosis tile 62 can include a diagnosis timeline 64. Diagnosis timeline 64 can provide a visual depiction of a patient's progress over time. As shown, for example, diagnosis timeline 64 can be stratified or otherwise broken up to indicate depression severity levels, a change in diagnosis, or disease progression. In some aspects, the PHQ-9 score (or other severity metric) can provide the severity ranges. For example, the patient was initially diagnosed in June of 2018 as having moderate depressive disorder. As time progresses, the depression severity can change. As shown, the patient was diagnosed in a follow-up assessment in September of 2018 as having major depressive disorder. In some aspects, diagnosis timeline 64 can include summarized treatment information. As an example, the patient started taking Bupropion (Wellbutrin®) shortly after his initial diagnosis. In addition, the patient regularly attended cognitive behavioral therapy (CBT) sessions, as an additional form of treatment. Diagnosis timeline 64 may further include any treatment or intervention, start and/or end dates associated with each treatment or intervention, dosages and dosage changes associated with each treatment, patient response to each treatment or intervention, updated diagnostic or laboratory testing results/description of method/dates, dates of evaluations, adverse events and associated details, dates of follow-up appointments, disease states observed at follow-up appointments, and other observational notes that may be gathered from therapy sessions and recorded with the date of the session.

Diagnosis timeline 64 can assist a provider with quantitatively assessing not only a patient's disorder progression, but can demonstrate the effects of various treatments over time. As shown, the patient's depression state worsened after using this specific medication. Accordingly, the provider safely discontinued the medication treatment and followed up with genetic sequencing to determine if the patient may be predisposed for risk or trouble metabolizing certain medications (or medication types).

Figure 3A:
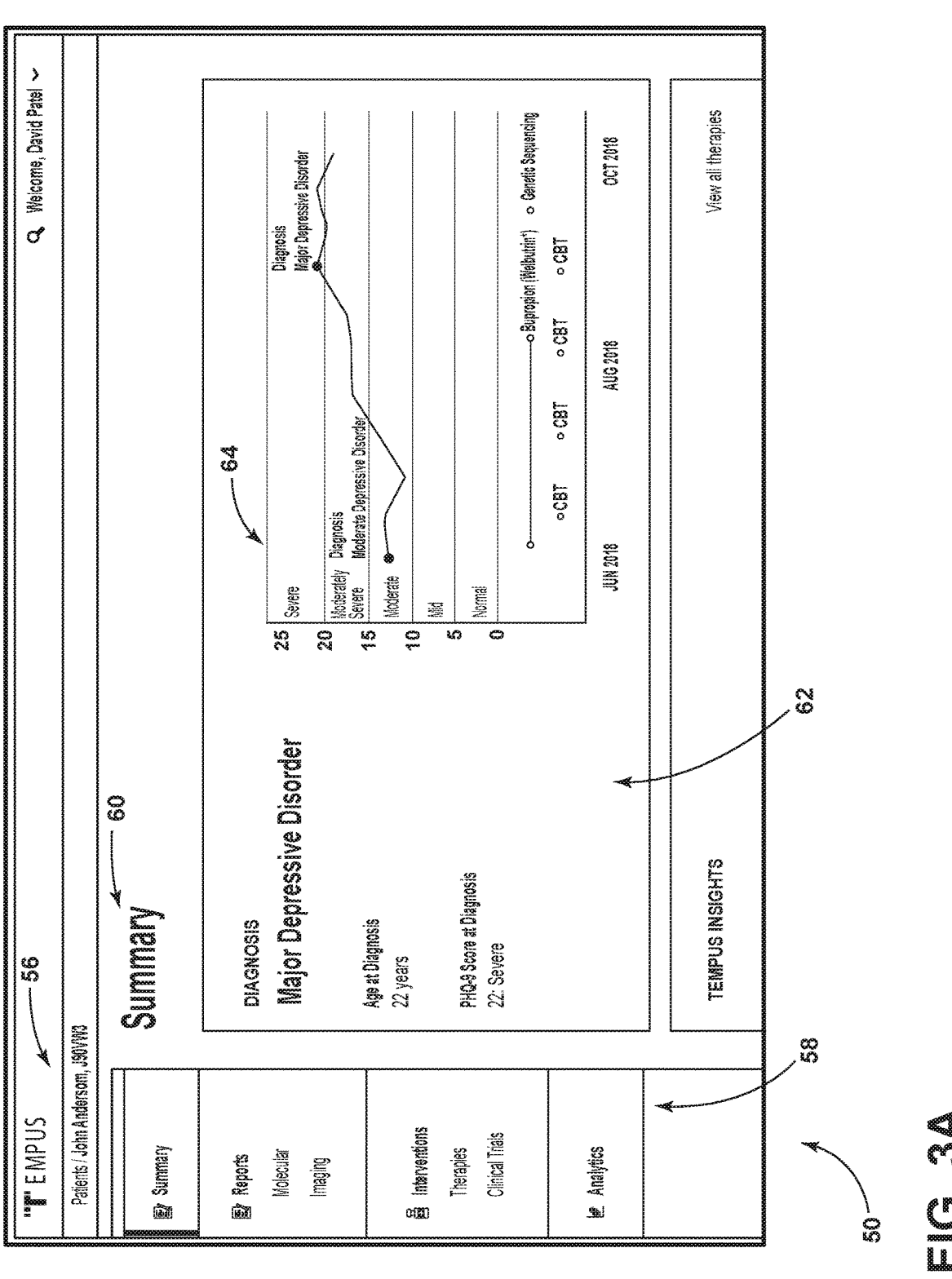
FIG. 3A is another image of the example GUI of FIG. 2, according to aspects of the present disclosure.
Figure 3B:
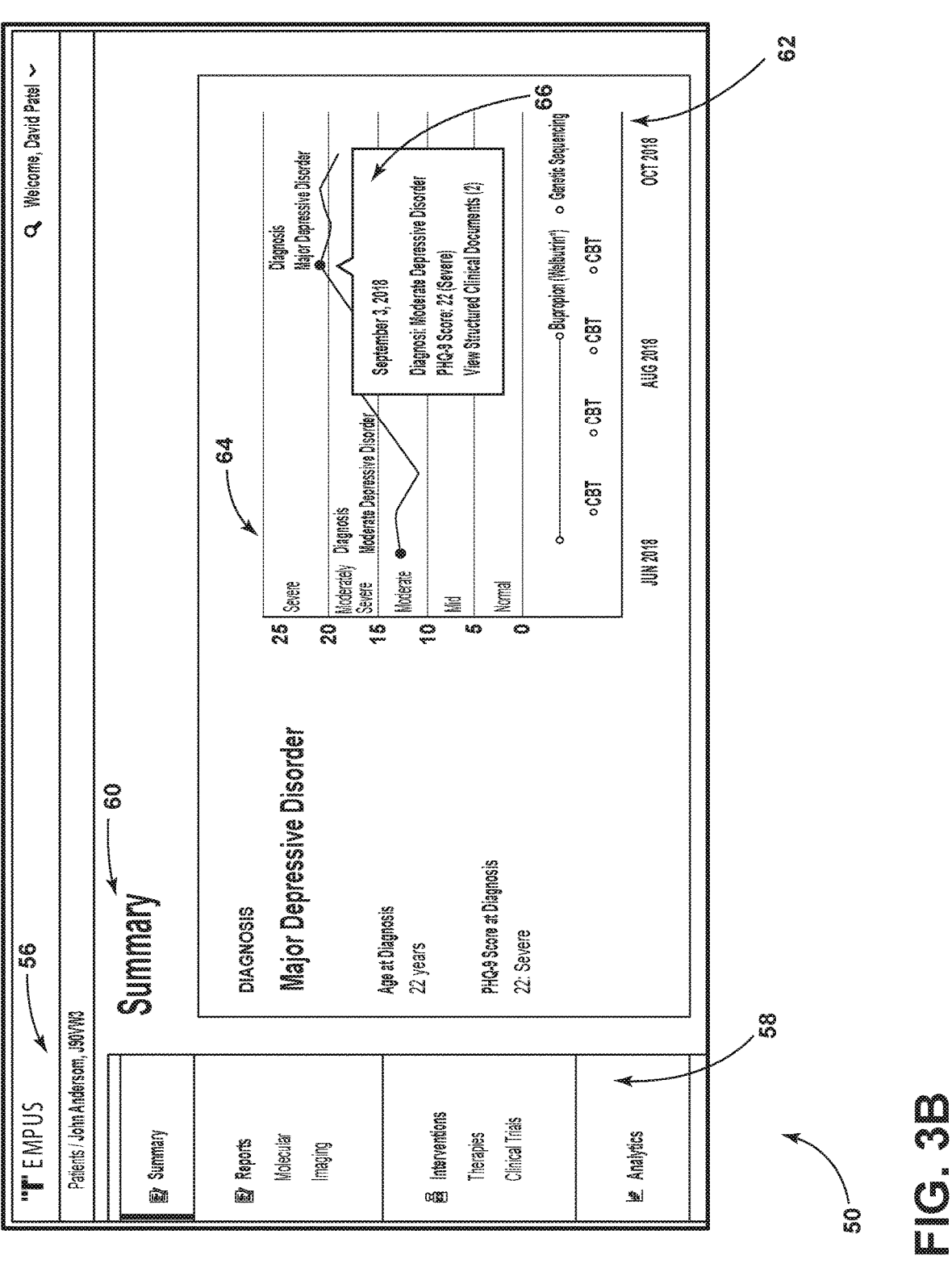
FIG. 3B is another image of the example GUI of FIG. 2, according to aspects of the present disclosure.

As shown by FIG. 3B, a provider may hover over (or select) diagnosis points within diagnosis timeline 64. An information box can subsequently appear, which can include summary information for the diagnosis point. As shown, on Sep. 3, 2018, the patient was diagnosed with major depressive disorder, with a PHQ-9 score of 22 (severe), and two structured clinical documents are available for viewing. In some aspects, the provider can select "view structured clinical documents," and GUI 50 can display the clinical documents pertaining to the diagnosis point.

Figure 3C:
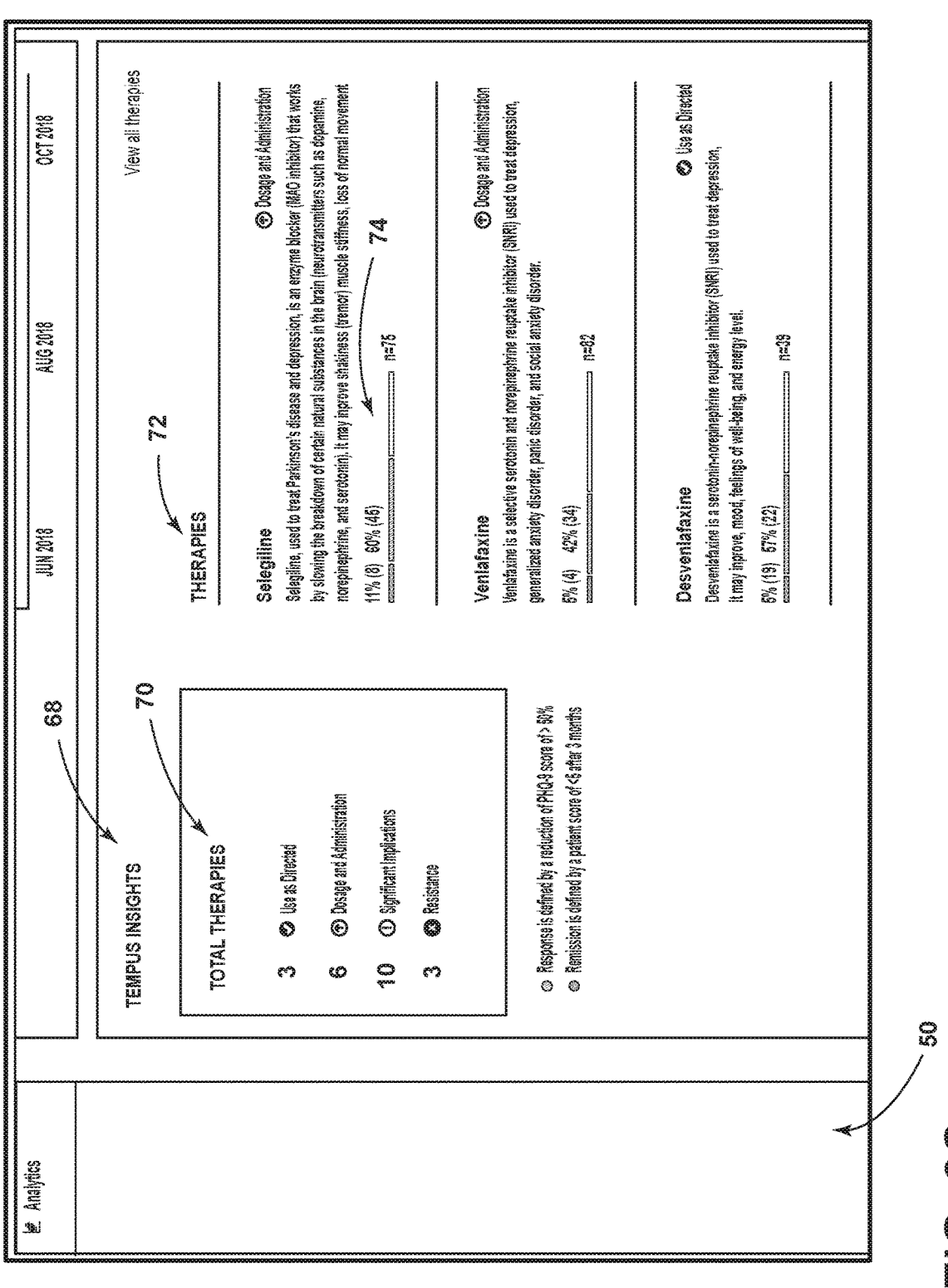
FIG. 3C is another image of the example GUI of FIG. 2, according to aspects of the present disclosure.

Referring to FIG. 3C, summary portion 60 is shown to include therapies tile 68 ("Tempus Insights"). Therapies tile 68 can include a summarized "total therapies" portion 70. In some aspects, total therapies portion 70 can include a summary of how the individual patient may respond to available therapies. As shown, three therapies are classified as "use as directed," six therapies are classified as "dosage and administration," ten therapies are classified as "significant implications," and three therapies are classified under "resistance." In another example, "use as directed" may be classified as "standard administration," and the categories covering "significant implications," "resistance," or other drugs with predicted adverse effects may be titled "contraindication."

According to the reported drug classifications, a provider may consider first treating the patient with one or more of the three therapies classified as "use as directed." Additionally, a provider may review therapies for "dosage and administration" as well as "significant implications" to learn more about the dosages of the drugs typically offered as well as the administration methods, periods, frequencies, and combinations of drugs that may be offered as along with the implications that may be considered for each of the therapies. For example, a subset of patients may respond well to therapies of a drug under a certain dosage threshold and respond negatively to dosaged that exceed a certain dosage threshold. A significant implication may be inferred from the drug therapy as a warning from FDA guidelines or reports or a clinical trial review. Conversely, a provider may consider monitoring the patient closely when treating the patient with the three therapies classified as "resistance," or avoiding treating the patient with these therapies. In some aspects, recommended therapies (such as "use as directed") can be identified with a unique marker and/or color (as shown, a check mark with a green background). Similarly, therapies that are not recommended (such as "resistance") can be identified with a unique marker and/or color (as shown, an "X" with a red background). In this way, a provider may efficiently identify which treatments to try, and which treatments to avoid.

Therapies tile 68 can further include a therapies list 72. Therapies list 72 can provide detailed descriptions for each therapy (such as primary use, side effects, etc.). Each of the therapies can be associated to a corresponding classification, enabling the provider to quickly find recommended treatments. In some aspects, each therapy can include a predicted response portion 74. As shown, predicted response portion 74 can be displayed on GUI 50 as a segmented line, with each segment and/or color corresponding to a different response. For example, one colored segment can represent a patient response defined by a reduction of the PHQ-9 score of greater than 50%. Additionally, another colored segment can represent a patient response defined by remission (a PHQ-9 score of less than 5, after 3 months of treatment). In some aspects, a provider can select "view full results," and GUI 50 can subsequently display detailed therapy information. Near each predicted response portion 74, a "n" value may be additionally displayed. In some embodiments, the "n" value may indicate the total number of patients for whom response information is available. In other embodiments, the "n" value may indicate the total number of patients in the cohort associated with the patient who received the treatment identified in the list and for whom response information is available.

Referring now to FIG. 3D, summary portion 60 is shown to include molecular overview tile 76 and imaging overview tile 78. In some aspects, molecular overview tile 76 can include various genes and enzymes, as well as the patient's corresponding test results. For example, the genetic sequence of the CYP2D6 gene for this particular patient is shown to make the patient a poor metabolizer, and the genetic sequence of the HTR2A gene is shown to result in normal activity. The molecular overview tile 76 can provide high level information to a provider for use in determining a medication type and/or dosage for a patient. In some aspects, a provider can select "view full results," and GUI 50 can subsequently display detailed molecular information. In some embodiments, molecular overview tile 76 includes genetic data, detected star alleles, and/or predicted phenotype for the patient, and a supplementary data section (for example, detailed information 96) includes drug-gene interactions.

Predicted phenotype may be influenced by the variants, alleles, and/or combinations of alleles detected in the patient for a particular gene, and/or combinations of these data for all genes.

Still referring to FIG. 3D, imaging overview tile 78 can include imaging results that correspond to the patient. As shown, imaging overview tile 78 can include several viewing options (such as view menu 82), imaging results 80, as well as relevant imaging data. Here, for example, the patient is positive for white matter hyperintensity, which indicates that the patient may be resistant to Escitalopram, Sertraline, and/or Nortriptyline. The conclusion that the patient may be resistant may be based on a proprietary database of aggregated patient information and custom curation of published scientific research and additional primary literature. Other relevant imaging data can be displayed within imaging overview tile 78, based on the results for each individual patient. Results are not limited to white matter hyperintensity and may include MRI, fMRI, CT scan, PET scan, or any other patient imaging technology. In some aspects, a provider can select "view full results," and GUI 50 can subsequently display detailed molecular information.

Referring now to FIGS. 4A-4E, GUI 50 can display a patient's detailed molecular data. Menu 58 can again provide an indication of where the provider is within the platform. Molecular report 90 can include the testing date (such as Aug. 15, 2018), as well as an alterations list 92, additional variants of interest 98, human leukocyte antigen (HLA) typing 100, therapeutic implications 102, and/or diagnostic implications 104.

Figure 4A:
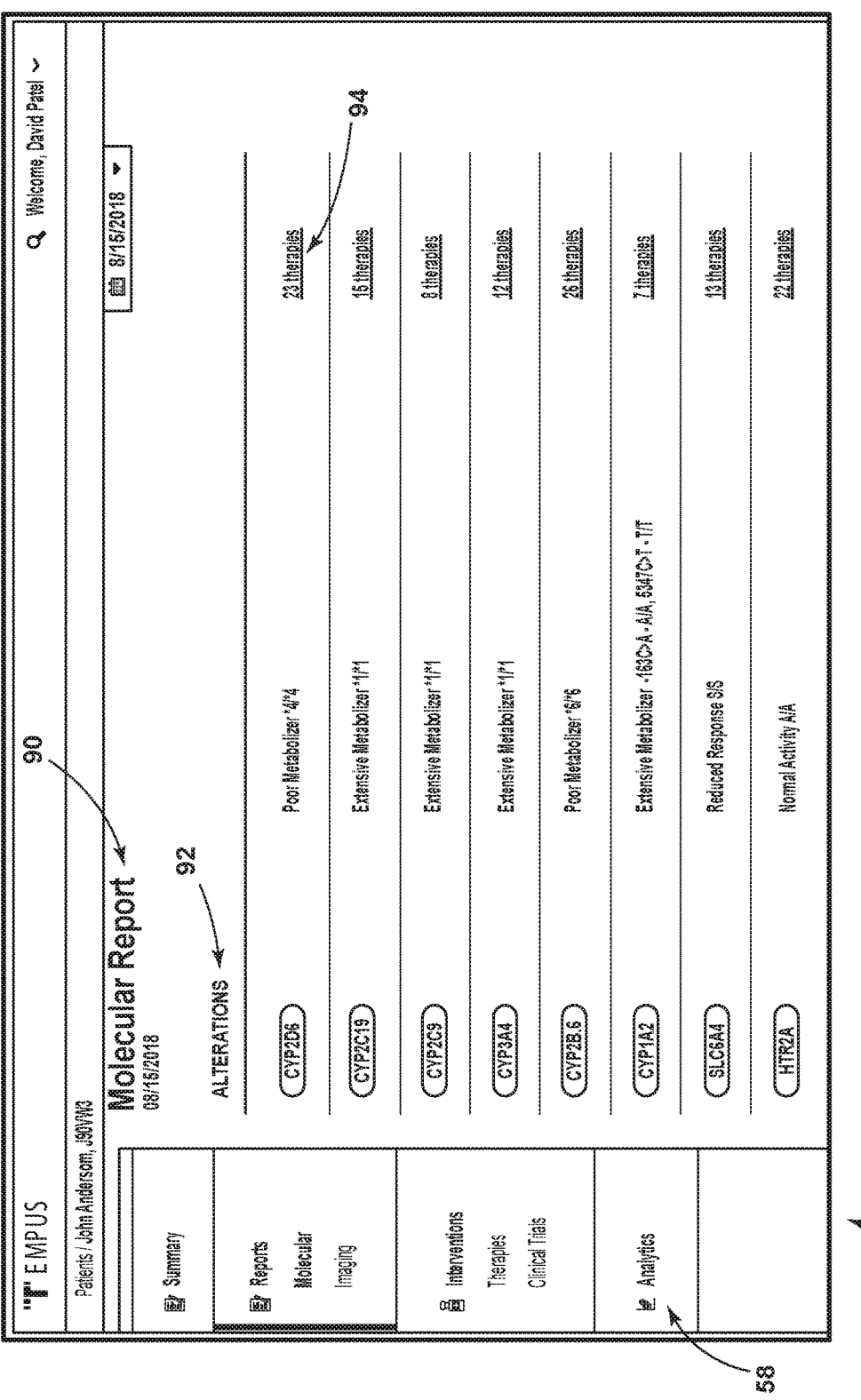
FIG. 4A is another image of the example GUI of FIG. 2, according to aspects of the present disclosure.
Figure 4B:
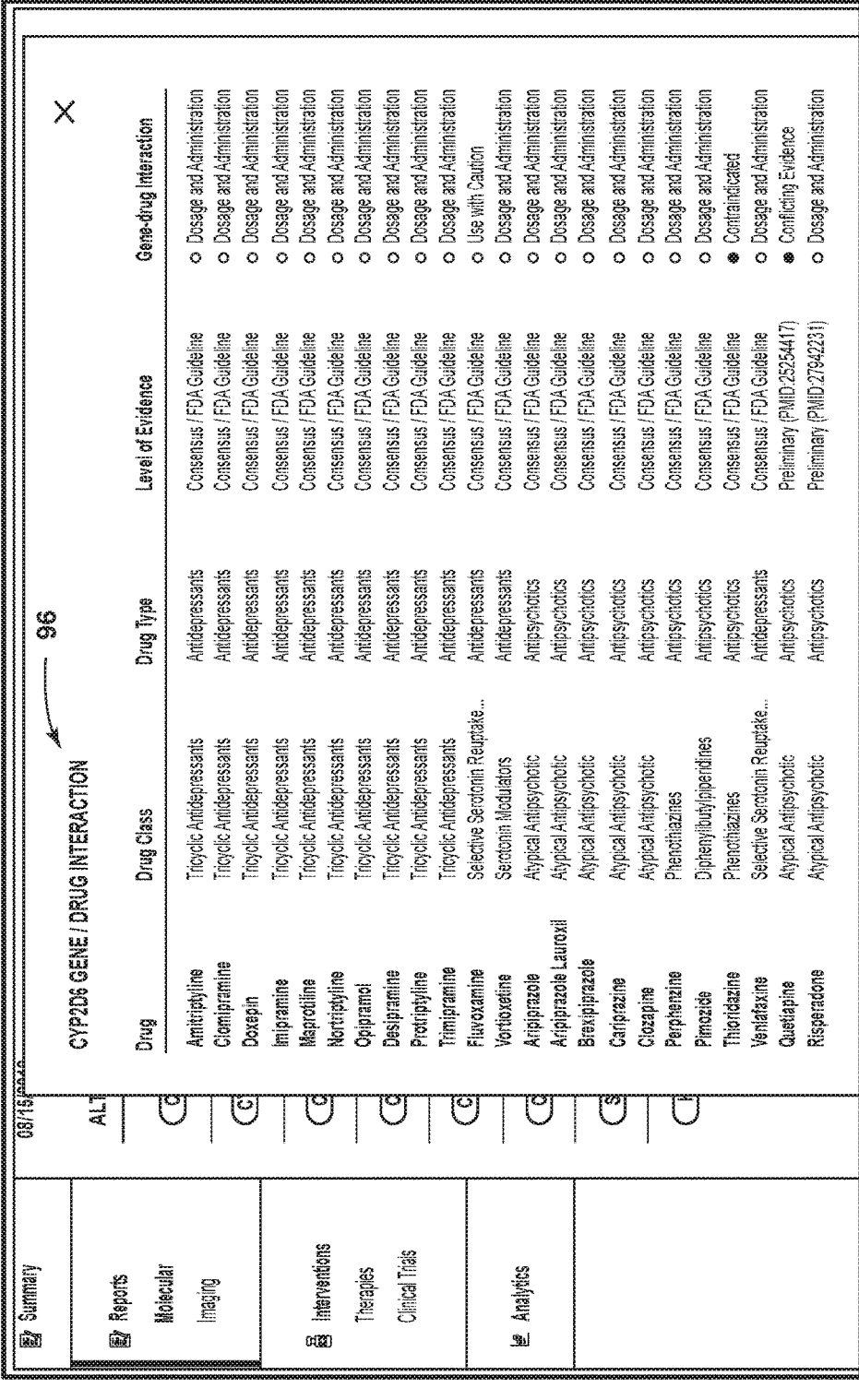
FIG. 4B is another image of the example GUI of FIG. 2, according to aspects of the present disclosure.

As shown in FIG. 4A, alterations list 92 can include detailed information for the patient's various genes and/or enzymes. In some aspects, each listed alteration can have a selectable therapies icon 94. A provider can select therapies icon 94, and GUI 50 can subsequently display detailed information 96 for the corresponding alteration. In some aspects, an information window may appear, overlaid on the molecular report 90. As shown, detailed information 96 can include a list of known drug interactions corresponding to the alteration. Detailed information 96 can include drug names, drug classes, drug types, level of evidence, and/or gene-drug interaction. The gene-drug interaction column can classify the type of interaction (such as "use with caution," "contraindicated," etc.). In some aspects, severity of interaction can be identified via color indicators (such as yellow indicates moderate, red indicates severe).

As shown in FIG. 4C, molecular report 90 can include additional variants of interest 98. A list can display a patient's genetic variants that are generally expressed in patients with a specific diagnosis. As one example, the patient has a variant corresponding to the ANK3 gene. The ANK3 rs10994415 C variant can increase the risk for schizophrenia by affecting ANK3 expression levels. Further, ANK3 is thought to be a susceptibility gene specific to bipolar disorder. Accordingly, additional variants of interest 98 can provide information to a provider, which can directly impact a patient's diagnosis and/or treatment.

In some aspects, a selectable reference icon can be provided, and GUI 50 can display detailed information upon selection. Molecular report 90 can further include HLA typing 100. HLA genotypes are determined using RNA or DNA sequencing data, and can be displayed via GUI 50. HLA typing 100 can be valuable for researchers or clinicians and for predicting pharmacogenetic effects. In one example of a drug-gene interaction or pharmacogenetic effect, specific HLA haplotypes may be associated with the development of Steven-Johnson syndrome and toxic epidermal necrolysis in some patients who take drugs such as Carbamazepine. Molecular report 90 may also be based on custom curation and data management of published scientific research and additional primary literature, for example in a KDB 40, as well as the interpretation of these data selected for display in the molecular report 90. In some examples, a notice may be included with the HLA typing 100 that the information should only be used for research and validated with histology or other clinical pathology tests before use in clinical decision making. In other examples, such as where the HLA typing 100 may be used in clinical decision making without being validated with histology or other clinical pathology tests, the notice may be omitted.

Figure 4D:
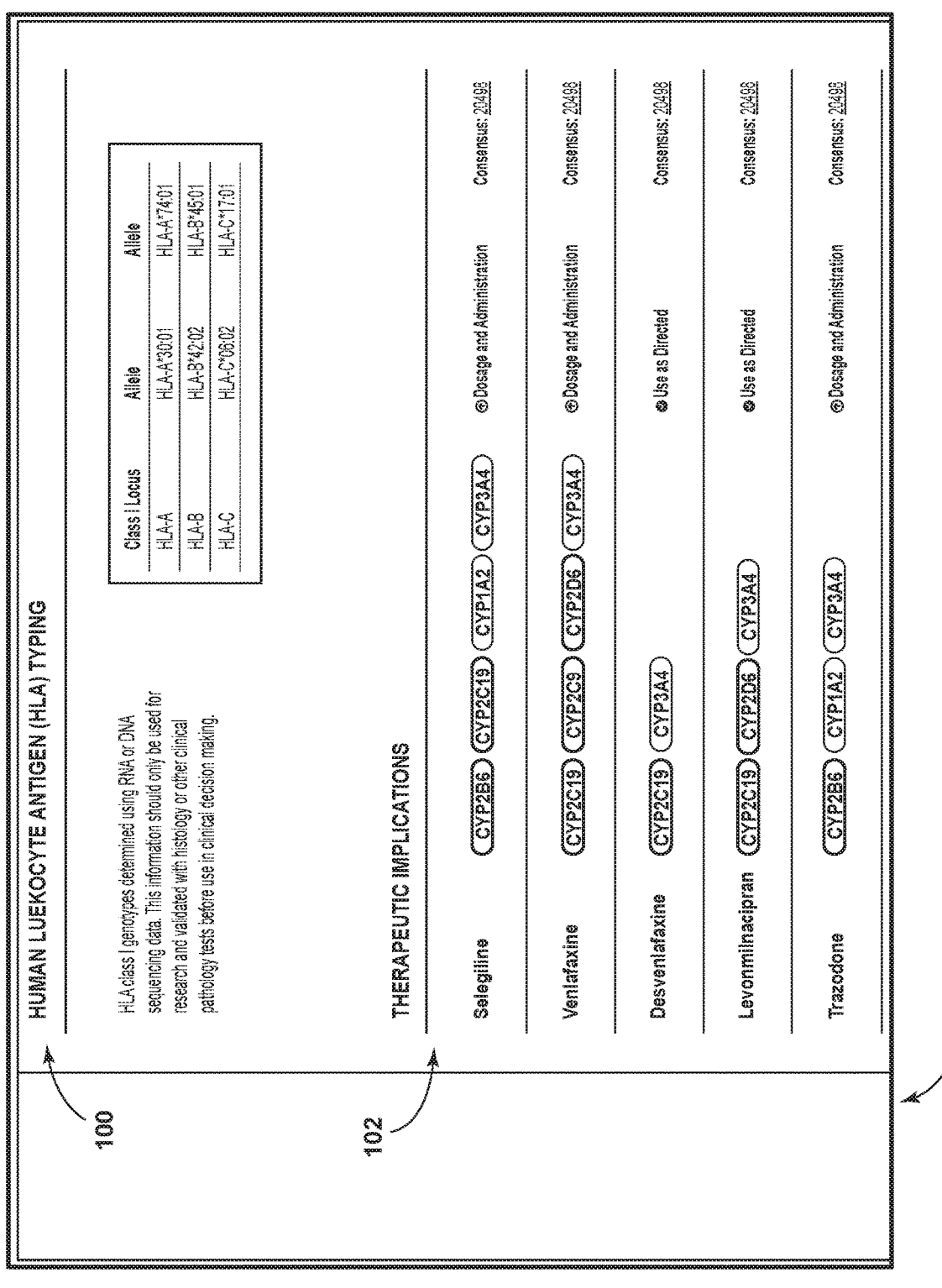
FIG. 4D is another image of the example GUI of FIG. 2, according to aspects of the present disclosure.
Figure 4E:
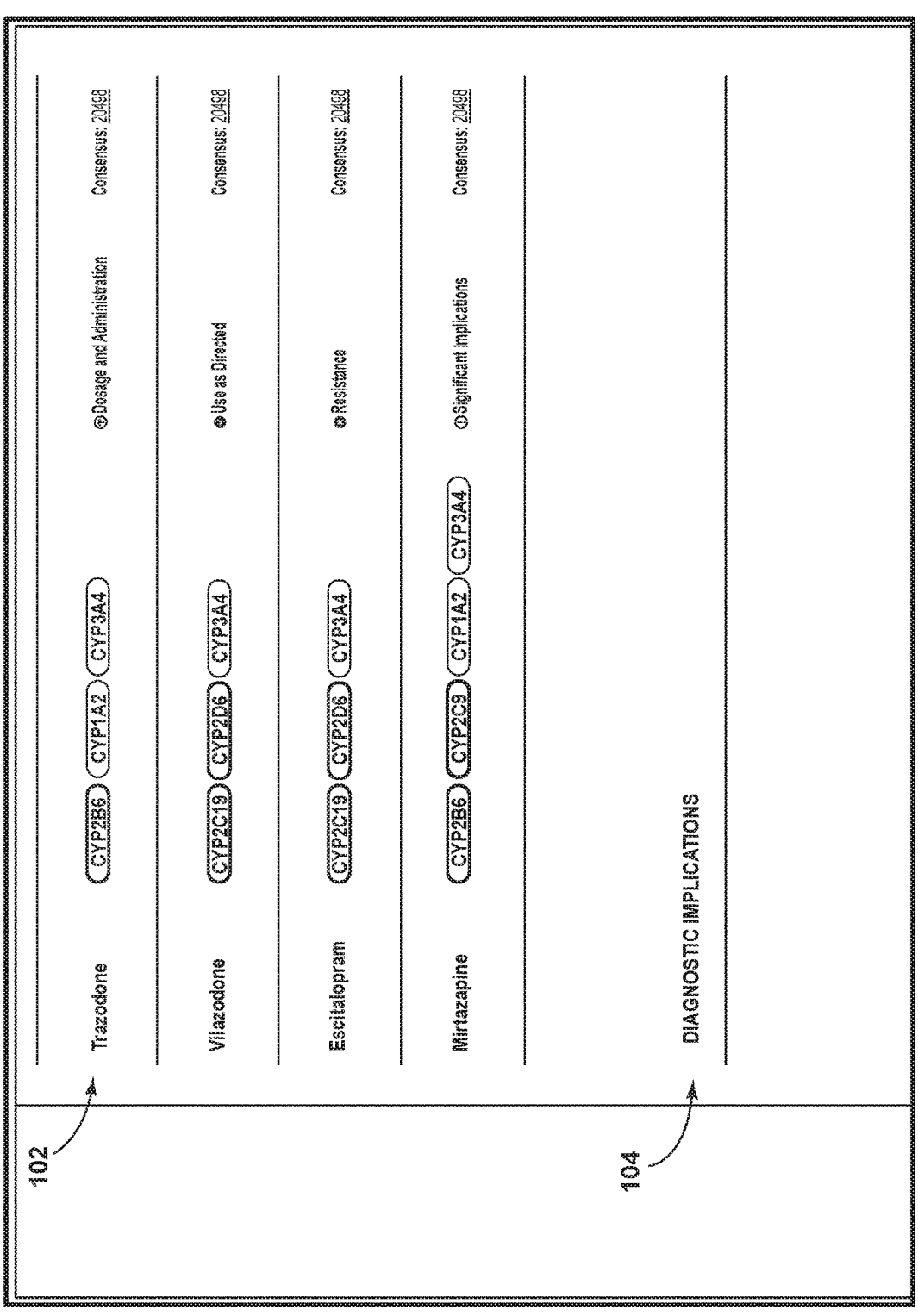
FIG. 4E is another image of the example GUI of FIG. 2, according to aspects of the present disclosure.

As shown in FIG. 4D, molecular report 90 can include therapeutic implications 102. In some aspects, therapeutic implications 102 can include a list of therapies, as well as corresponding genetic variant data. For example, Desvenlafaxine lists two applicable genetic variants, CYP2C19, and CYP3A4. Based on the patient's gene alterations, CYP2C19 is highlighted. Further, Desvenlafaxine is identified as a potential treatment for the patient (such as "use as directed"). Molecular report 90 can further include diagnostic implications 104, where applicable. In some aspects, a patient's molecular data can provide diagnostic insights, which can be identified and described within diagnostic implications 104. Additional diagnostic insights may be gained from FDA reports or guidelines, clinical trial reviews, or drug studies. In one example, diagnostic insights or diagnostic implications may be based on additional variants of interest contained in molecular report 90.

Figure 5A:
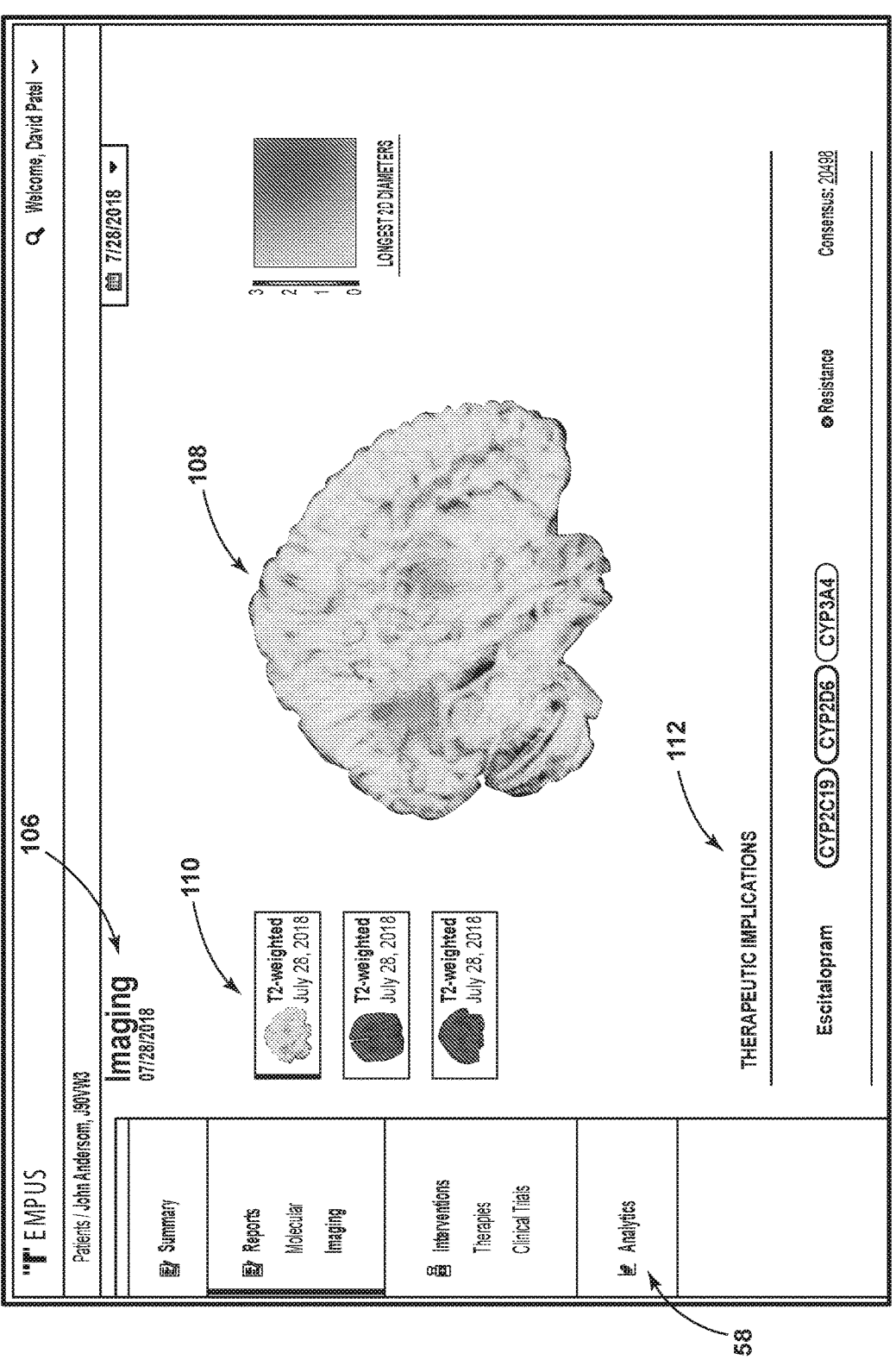
FIG. 5A is another image of the example GUI of FIG. 2, according to aspects of the present disclosure.
Figure 5B:
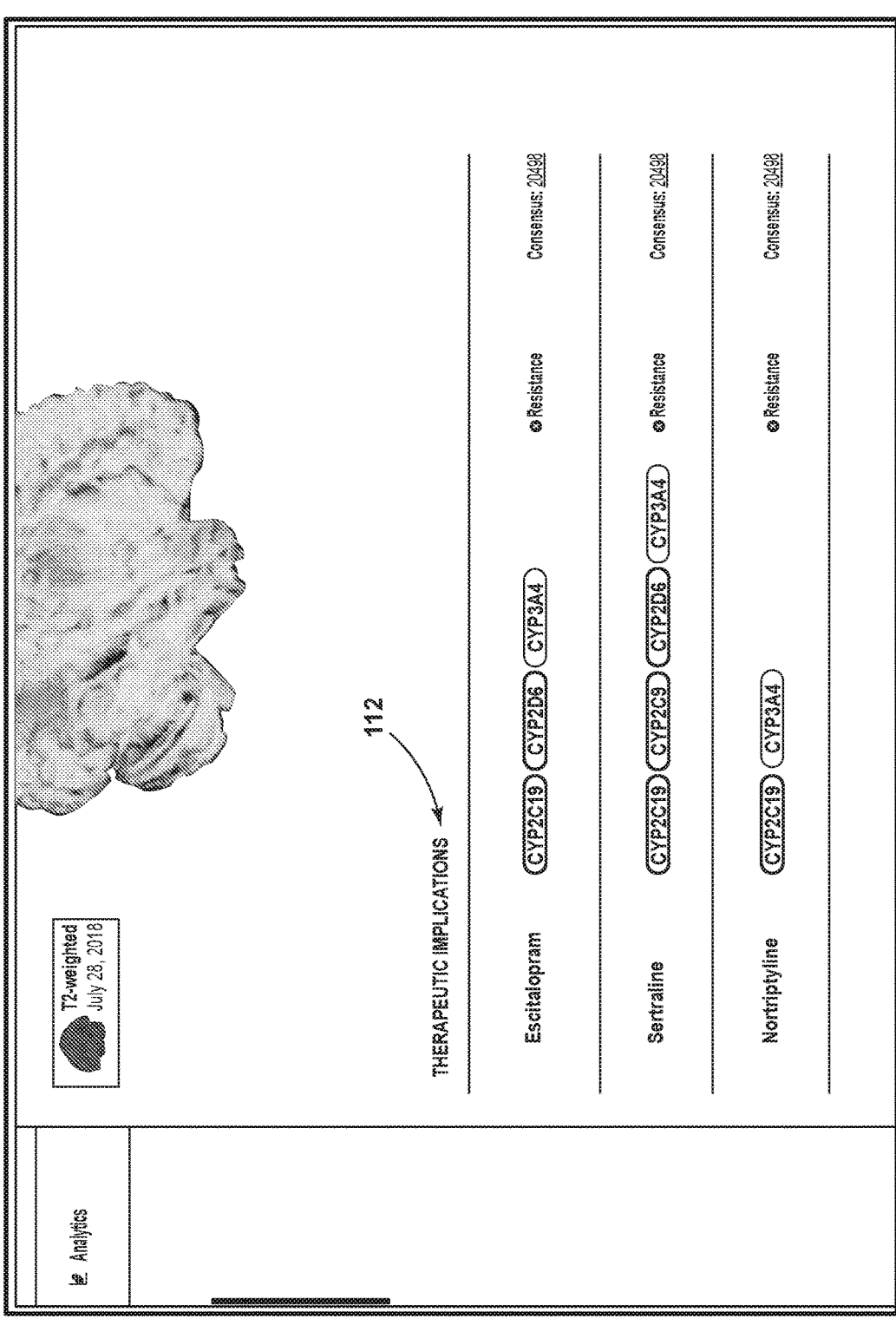
FIG. 5B is another image of the example GUI of FIG. 2, according to aspects of the present disclosure.

Referring now to FIGS. 5A-5B, imaging data 106 is shown. Menu 58 can again provide an indication of where the provider is within the platform. In some aspects, GUI 50 can display a graphical representation of imaging data (such as image 108). In one example, GUI 50 and the graphical representation of imaging data may be adjusted or customized based on the type of imaging 108 that the patient received. Types of images 108 may include a representation or image of the patient's face, MRI, CT scans, PET scan, etc. Further, coloring of image 108 can identify clinically significant features of the patient's brain. A view menu 110 can be provided, enabling the provider to select different view angles corresponding to the imaging data.

Imaging data 106 can include therapeutic implications 112. As shown, the system used the imaging data 106 to determine treatments to which the patient may be resistant. For example, Nortriptyline lists two applicable genes containing variants, CYP2C19, and CYP3A4. Based on the patient's gene alterations, CYP2C19 is highlighted. Further, Nortriptyline is identified as a potential resistant treatment for the patient (such as "resistance"). Such imaging data may include MRI or CT scans of the brain, which may allow additional insights to be observed, analyzed, and reported to the physician based upon clinical information associated with patients over the course of treatment. Additionally, an organoid laboratory may grow neurospheres or other organoids having a genetic variant, allele of interest, or another phenotypic trait for imaging and testing to determine effects on a drug and/or disease onset and progression that may be caused by the particular genetic variant, allele of interest, phenotypic trait or other conditions in the patient detectable by analyzing molecular and/or omics data. In one example, types of molecular and/or omics data include genomic, proteomic, metabolomic or other data collected by studying the molecules or cellular activity occurring in a patient. The testing and imaging of the brain may be combined to supplement the insights that may be included in the report.

Figure 6A:
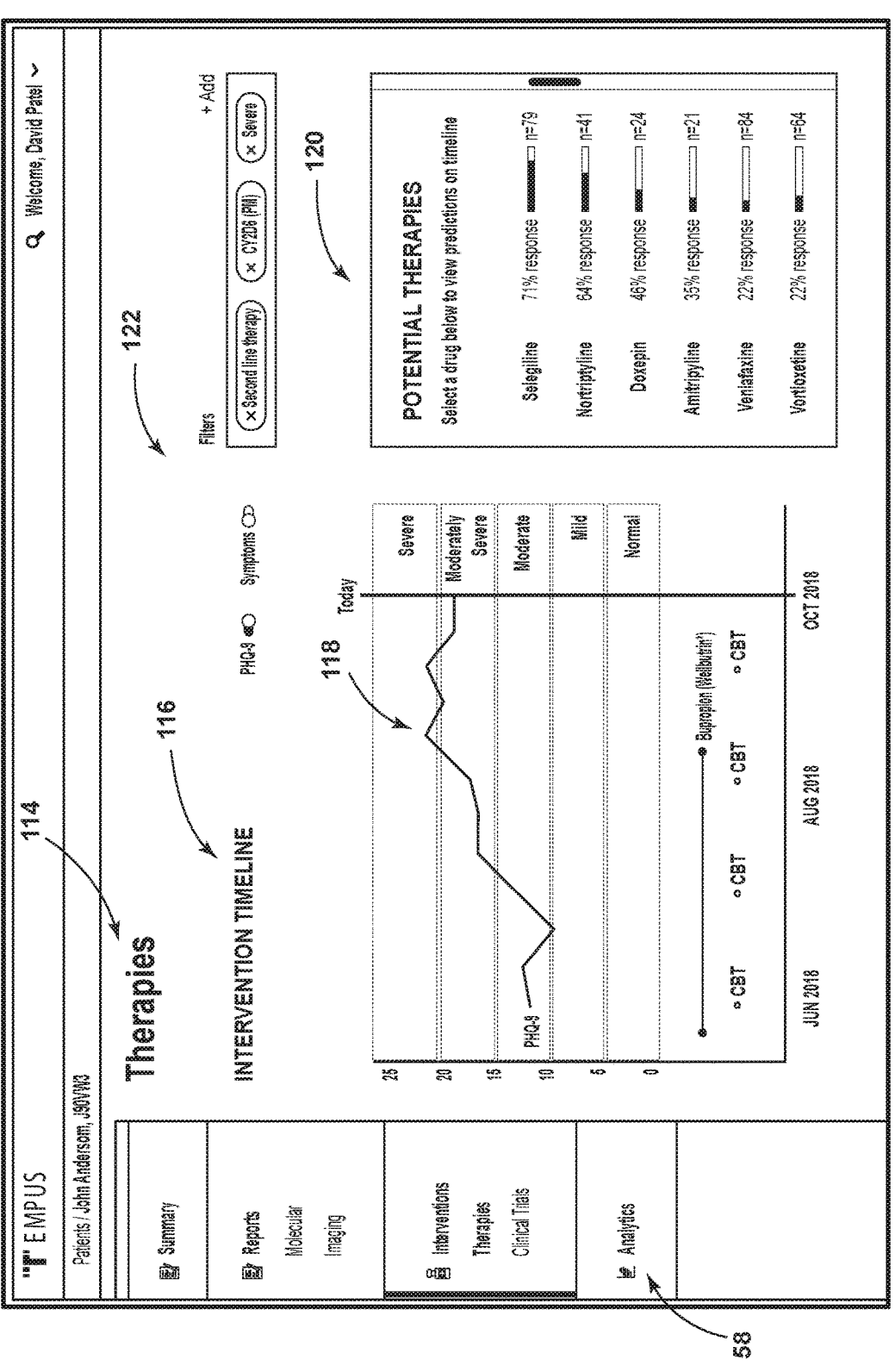
FIG. 6A is another image of the example GUI of FIG. 2, according to aspects of the present disclosure.
Figure 6B:
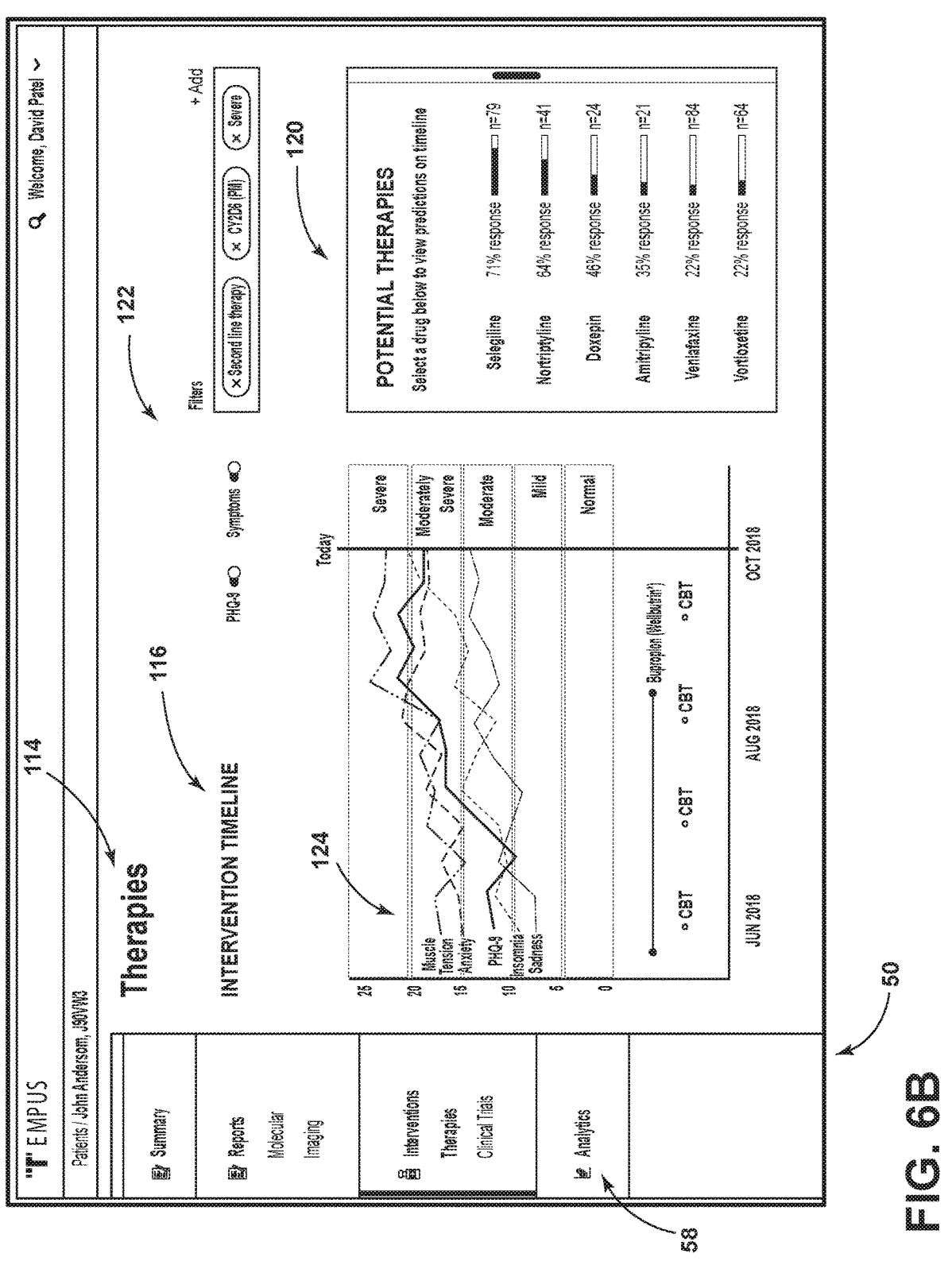
FIG. 6B is another image of the example GUI of FIG. 2, according to aspects of the present disclosure.

Referring now to FIGS. 6A-6E, GUI 50 can display therapies portion 114. Menu 58 can again provide an indication of where the provider is within the platform. In some aspects, therapies portion 114 can include an intervention timeline 116 with data 118. Further, therapies portion 114 can include viewing options 122 and potential therapies tile 120. In some aspects, viewing options 122 can include options to view PHQ-9 data, symptoms, and/or other qualitative and quantitative measurements of disease onset and progression on intervention timeline 116. Additionally, various filters can be selected, based on what treatment types are desired by the provider. As shown by FIG. 6B, when "symptoms" is selected within viewing options 122, intervention timeline 116 can be updated to display symptom data 124. In some aspects, intervention timeline 116 can display symptom data over time. In one example, symptoms may be reported by a clinician, patient, and/or third party including a patient's family members and symptom data may be obtained through curation of physician notes, direct electronic medical record (EMR) integrations, and/or integration with patient, family, or clinician facing applications.

Figure 6C:
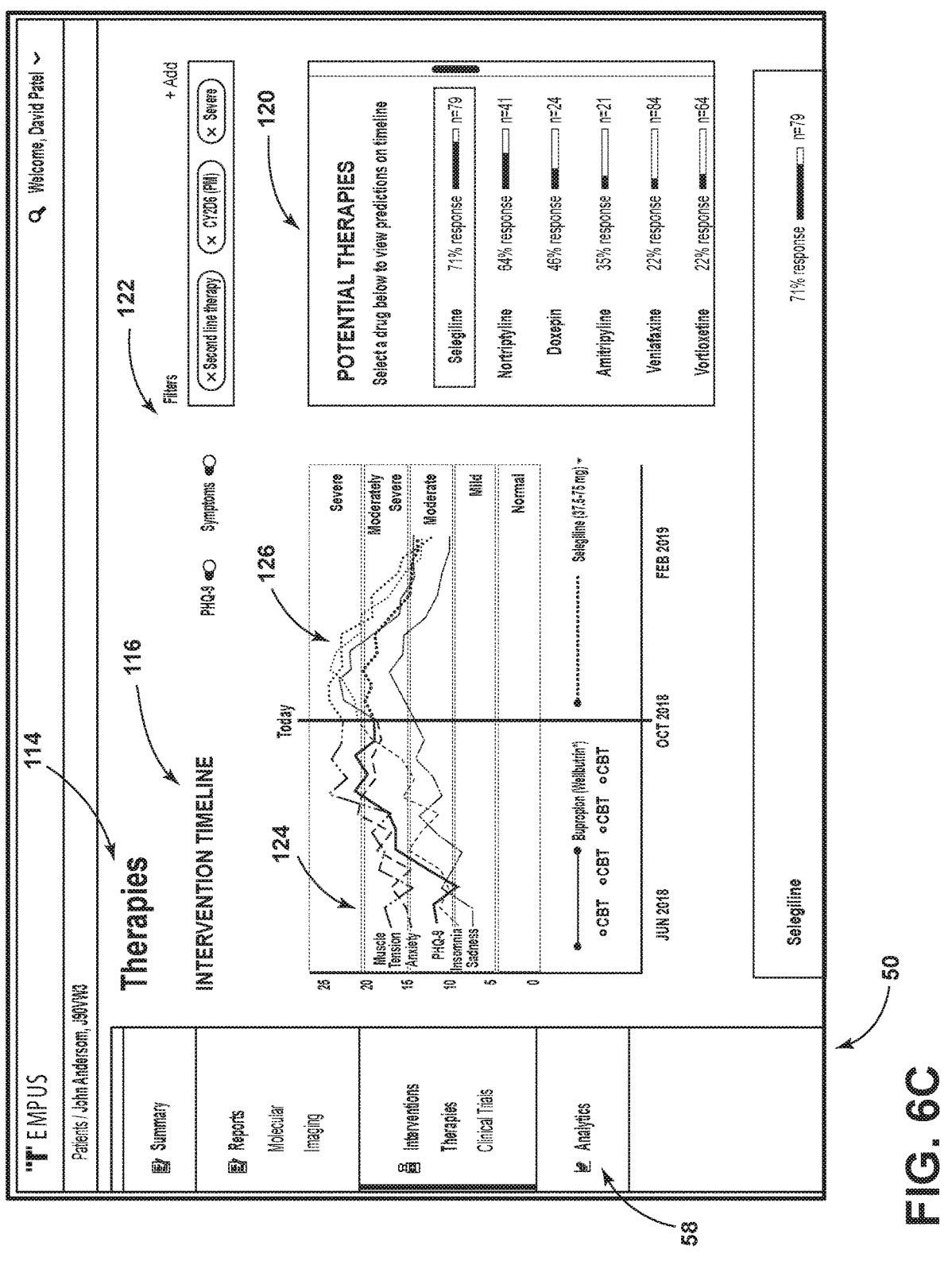
FIG. 6C is another image of the example GUI of FIG. 2, according to aspects of the present disclosure.
Figure 6D:
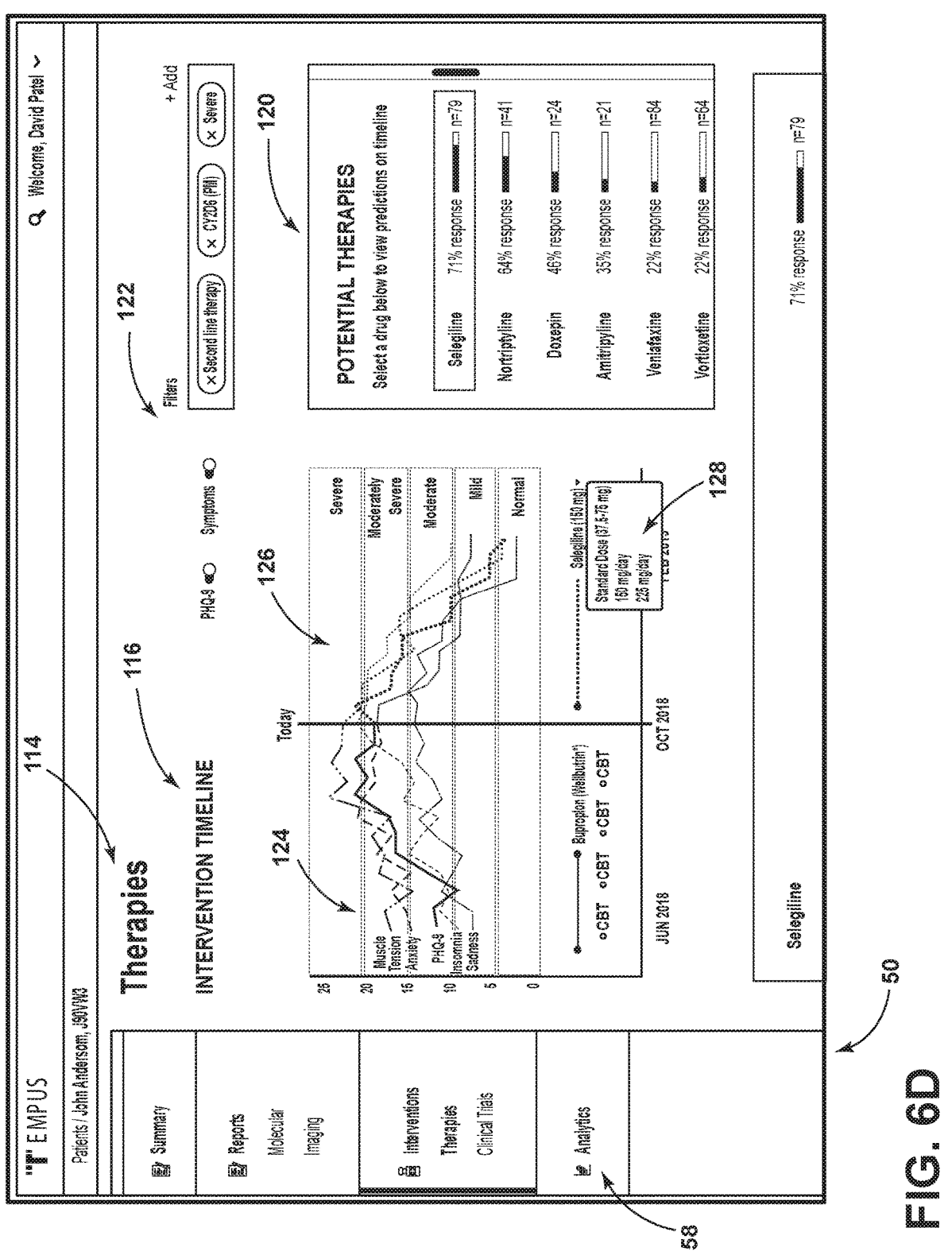
FIG. 6D is another image of the example GUI of FIG. 2, according to aspects of the present disclosure.

As shown by FIGS. 6C-6D, intervention timeline 116 can display predicted symptom, PHQ-9, and/or other measurement data 126, based on a selected therapy. For example, the provider selected Selegiline from potential therapies 120, and intervention timeline 116 can subsequently display predicted changes if the medication is prescribed. In one example, each symptom may respond differently to a range of therapeutic options. Understanding which treatments are most likely to provide a desired result may help a medical provider make decisions pertaining to personalized medicine in psychiatric disorders. Predicted changes may be used by the system 10 to calculate a predicted range of patient adherence to medication, which may be displayed in therapies portion 114. Patient adherence to medication may be quantified, for example, as a percentage of a prescription that is taken, as a measurable quantity of the drug or drug metabolite to be detected in the patient's bloodstream, as a value on a scale based on the frequency of prescription refills required by the patient and/or the degree of accuracy with which the patient follows a treatment regimen, or another indicator of adherence. In some aspects, GUI 50 can display dosage information 128. As shown, a provider can select different dosages of Selegiline using a dropdown menu on intervention timeline 116. FIG. 6D includes predicted symptom and PHQ-9 data 126 based on a 225 mg/day dose of Selegiline, whereas FIG. 6C includes predicted symptom and PHQ-9 data 126 based on a 37.5-75 mg/day dose of Selegiline. Accordingly, a provider can interact with GUI 50 to determine a recommended treatment, as well as a recommended dose for an individual patient.

Referring to FIG. 6E, therapy details 130 can be displayed via GUI 50, based on which therapy is selected from potential therapies tile 120. In some aspects, therapy details 130 can include dosing information, brand names, drug type, drug description, FDA evidence, Clinical Pharmacogenetics Implementation Consortium (CPIC) guidelines, and/or preliminary evidence based on patient data. In one example, therapy details 130 are searchable and can allow physicians to easily select a drug to specifically address symptoms associated with that drug.

Figure 7A:
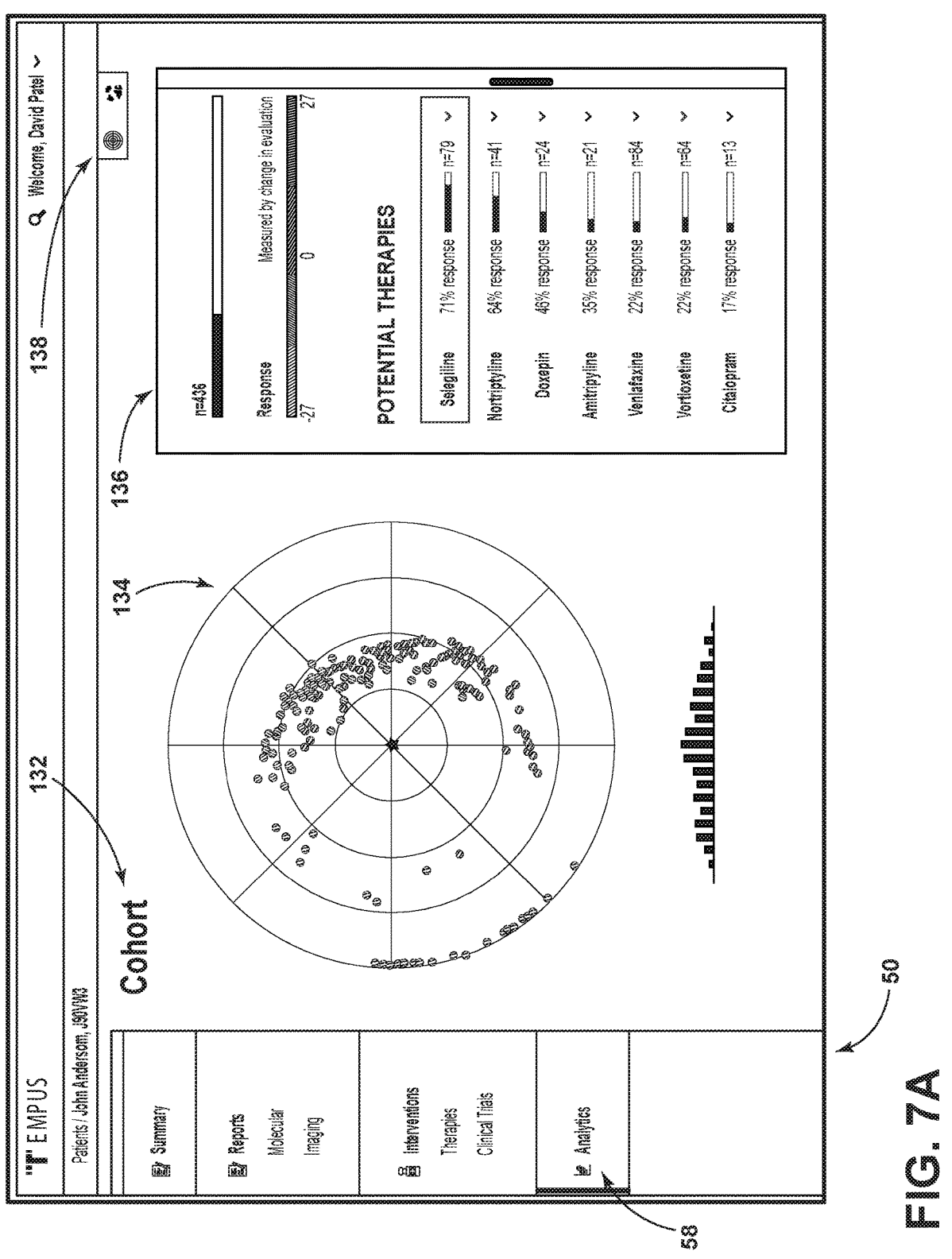
FIG. 7A is another image of the example GUI of FIG. 2, according to aspects of the present disclosure.

Referring now to FIGS. 7A-7D, cohort details 132 can be displayed via GUI 50. As shown, cohort details 132 can be displayed when the analytics portion of menu 58 is selected. Therapy data 136 can be included within cohort details 132. Radar plot 134 can compare an individual patient with other patients who share similarities. As shown, the individual patient can be represented at the center of radar plot 134, and patients with similar or distinct indicators can be represented by additional dots around the center indicator. Radar plot 134 can provide two measurements for which to draw similarities: a radial distance for similarities between the center point and each plotted point, and an angular distance for similarities between each plotted point. Similarities can include, but are not limited to, depression state, demographics, physical traits, genetic data, imaging data, and therapy history. FIG. 7A includes radar plot 134 that utilizes a set of patient data corresponding to the selected therapy Selegiline. Conversely, FIG. 7B includes radar plot 140 that utilizes a set of patient data corresponding to the selected therapy Nortriptyline. In one example, symbols representing patients are color-coded according to the patient's response to therapy. Response to therapy can be measured by multiple methods. In the example, the A (difference) between PHQ-9 scores at the start versus the end of therapy is shown. The variety of response measurements may be normalized to show many response measurements as a singular end point, for example, by integrating multiple response measurements into a single score value. The metadata for each drug (which may include, but is not limited to, dose, diagnosis at the time of prescription, likelihood or distribution of adherence, adverse events, etc.) may also be correlated to response.

Figure 7B:
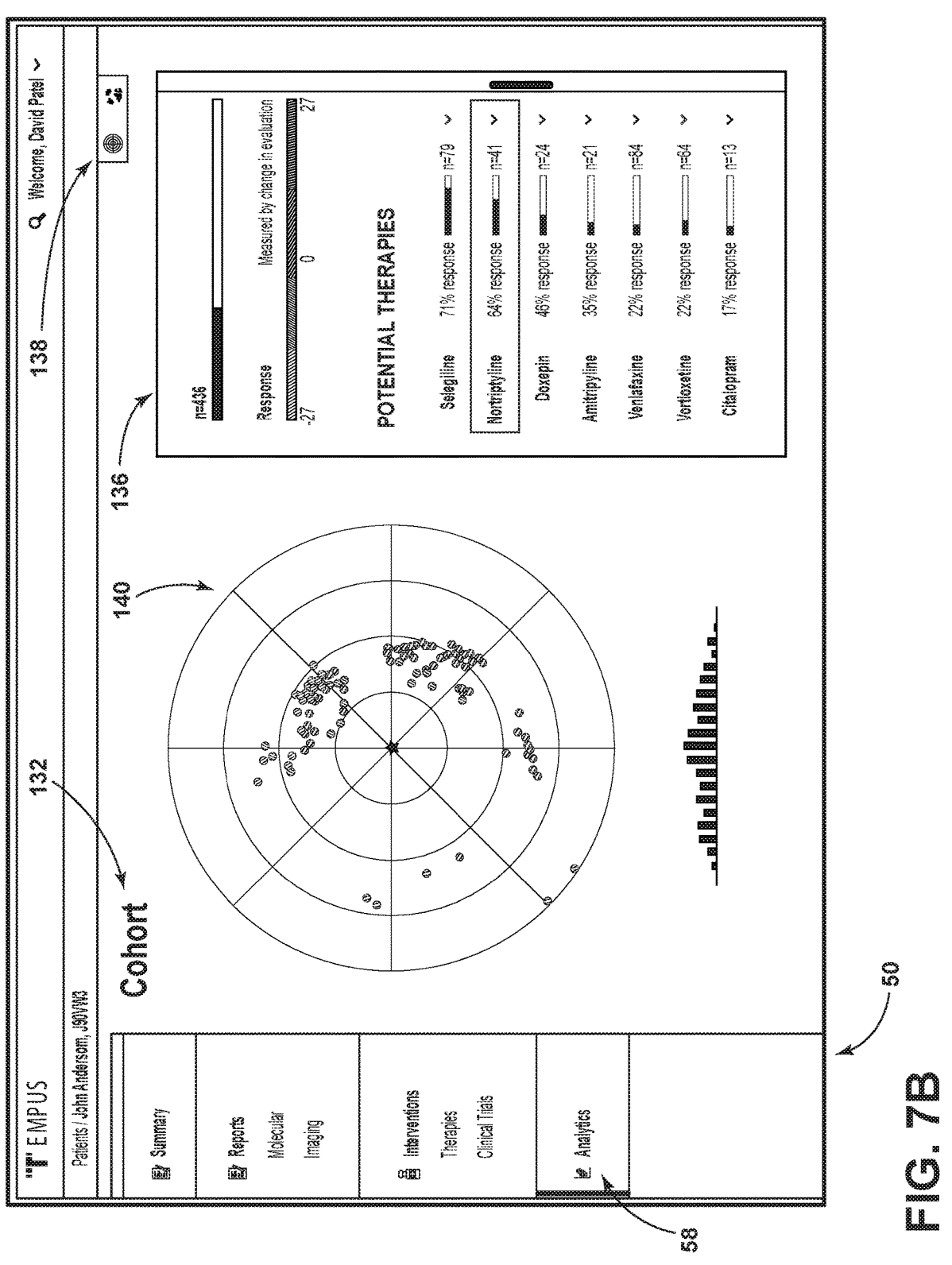
FIG. 7B is another image of the example GUI of FIG. 2, according to aspects of the present disclosure.
Figure 7C:
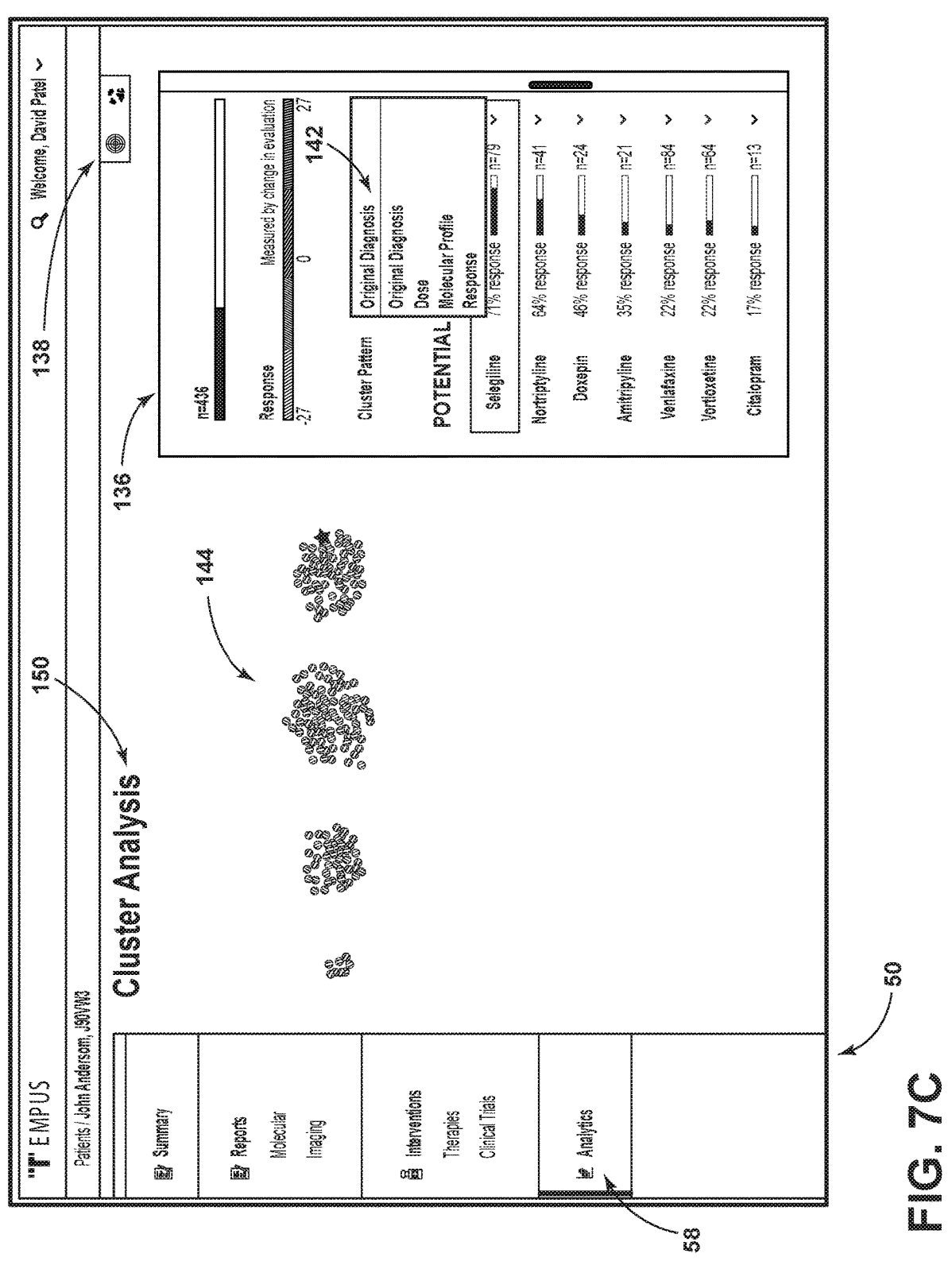
FIG. 7C is another image of the example GUI of FIG. 2, according to aspects of the present disclosure.
Figure 7D:
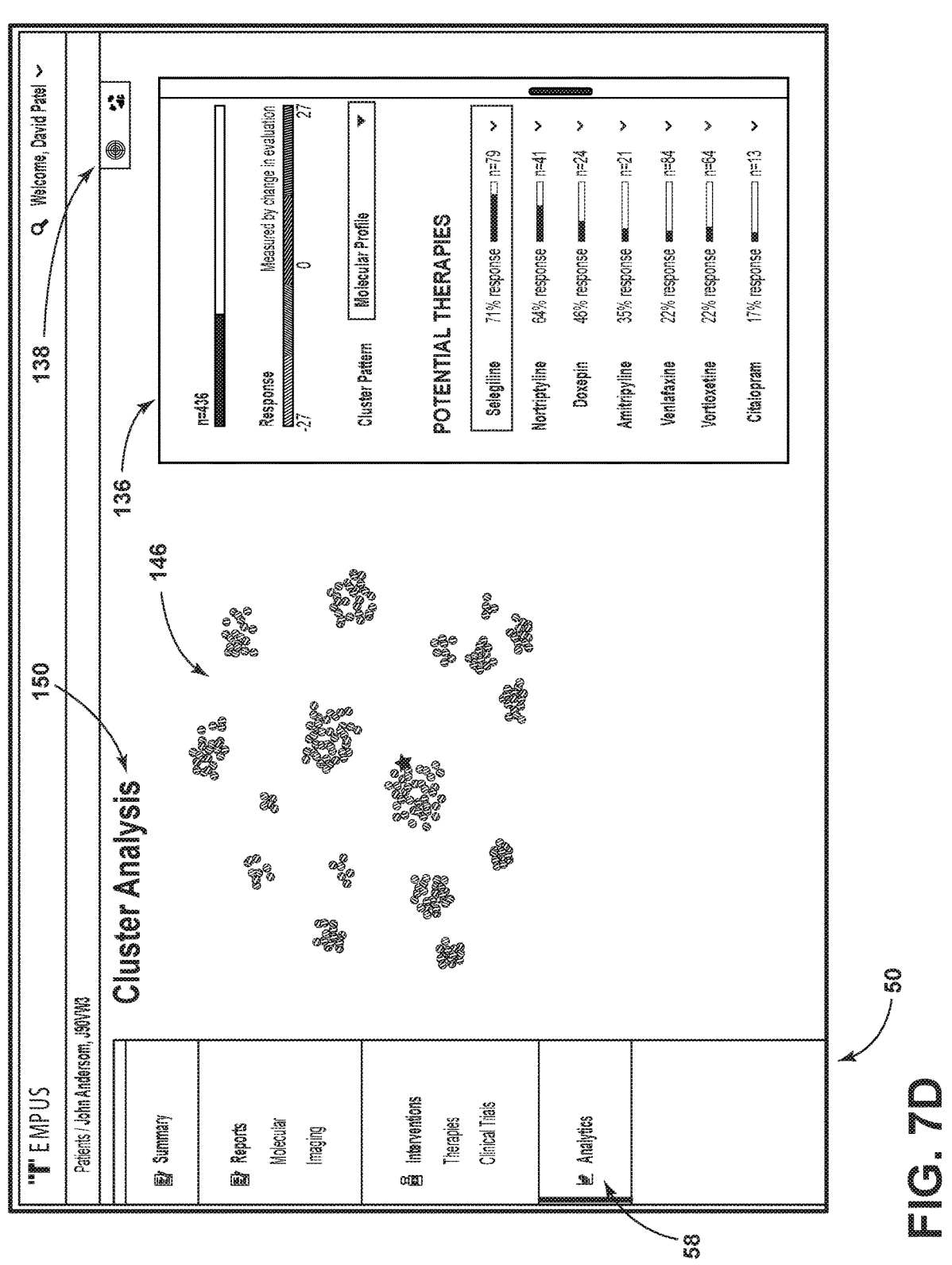
FIG. 7D is another image of the example GUI of FIG. 2, according to aspects of the present disclosure.

In some aspects, cohort details 132 can include menu 138. A provider can make viewing selections via menu 138. FIGS. 7A-7B include cohort details 132, whereas FIGS. 7C-7D include cluster analysis 150. As shown by FIG. 7C, a provider can select from a list 142 of cluster patterns (including, but not limited to, original diagnosis, dose, molecular profile, response). Displayed clusters 144 can compare an individual patient to other patients. As shown, the individual patient is represented by the "star" indicator, and the other patients are represented by dots. Again, dot distribution can be indicative of similarities. As shown, FIG. 7C includes displayed clusters 144 based on original diagnosis. Conversely, FIG. 7D includes displayed clusters 146 based on molecular profile. These clusters may be used to determine diagnosis, prognosis, therapy implications and research into diagnosis, subtyping diagnosis, therapies, prognosis, etc.

Figure 8A:
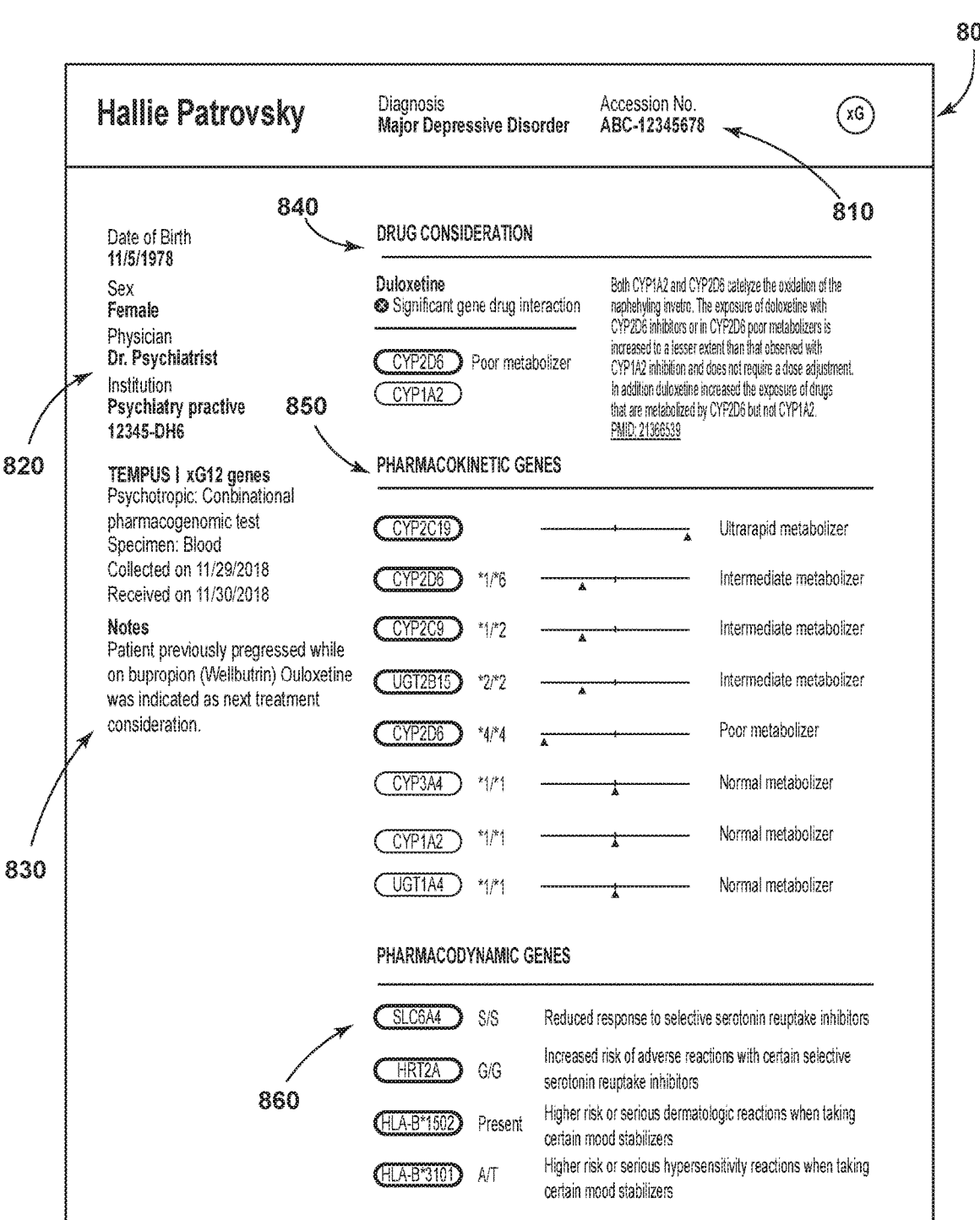
FIG. 8A is another image of the example GUI of FIG. 2, according to aspects of the present disclosure.
Figure 8B:
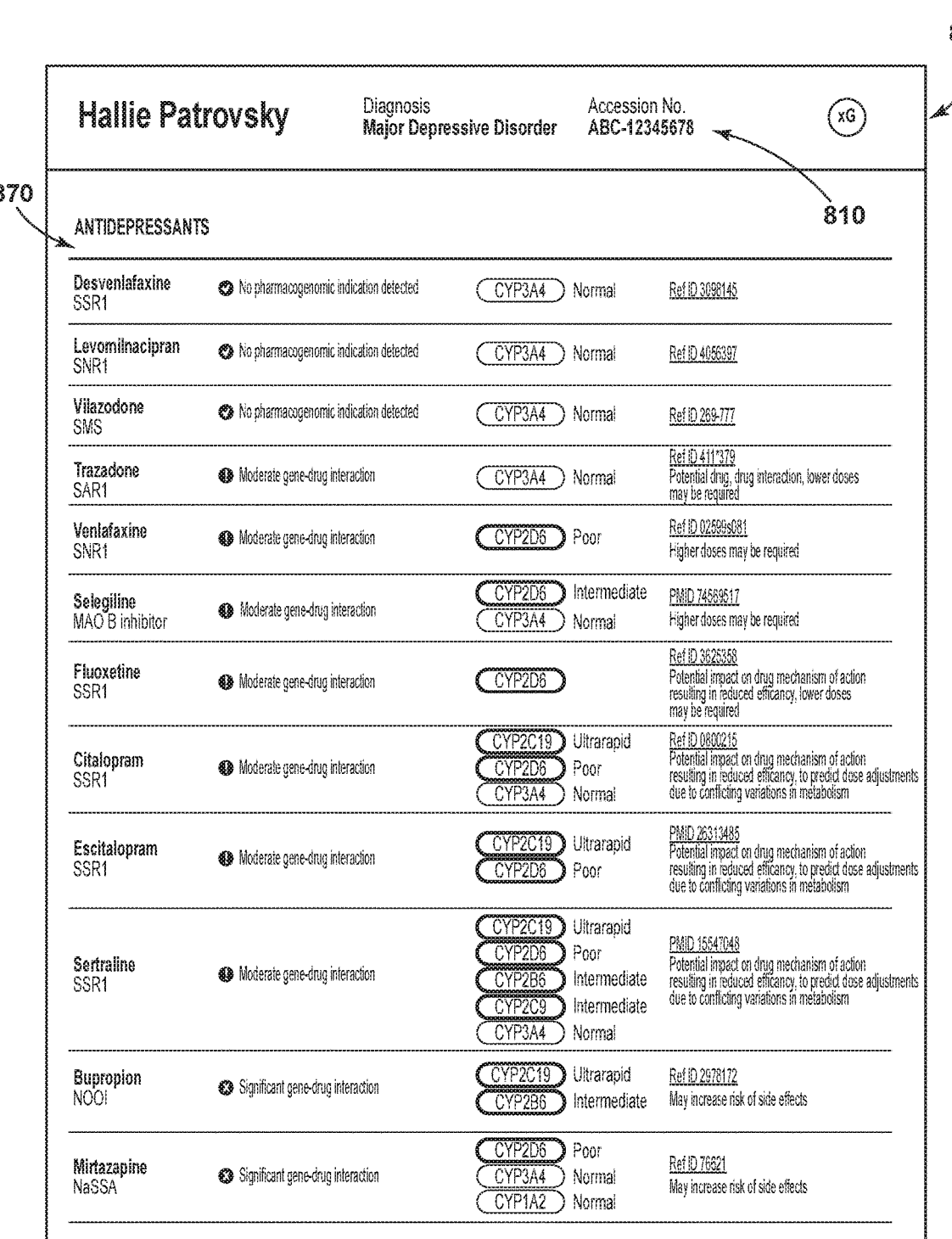
FIG. 8B is another image of the example GUI of FIG. 2, according to aspects of the present disclosure.

FIGS. 8A-B show further aspects of GUI 50, including a Patient Report 800 that may be generated for display via GUI 50 as a Report similar to Molecular 90 and Imaging 106 or exported as a PDF document for printing. In particular, GUI 50 is shown to display a patient identifier such as previously shown 56 (such as patient name), diagnosis tile such as previously shown 62, and other document identifiers such as an "Accession No." and/or an identifier for a type of NGS Panel, "xG", in a first portion 810. Further patient information such as Date of Birth, Sex or Gender, Name of Primary Physician, and/or Name of Institution and Institution Identification Codes may be presented in a second portion 820. Second portion 820 may further include information identifying the Laboratory which generated the panel results and report, "Tempus", the panel identifier and number of genes associated with sequences that are reported for the patient, "xG 12 genes", the nature of the report, "Psychotropic: Combinatorial pharmacogenetic test", the type of specimen collected for the genetic test panel, "Blood", as well as dates for collection by the ordering institution and receipt by the laboratory. In one example, the "xG 12 genes" panel is a whole exome panel with spike-in probes added such that the panel targets and analyzes the genetic sequences of certain intronic regions of the human genome, in addition to all known exon regions, which includes approximately 20,000 genes. In one example, the report may not display information for all of the genes that are analyzed by the genetic panel.

A third portion 830 may include notes regarding pertinent clinical information, for example, prior medications prescribed and/or taken by the patient which resulted in disease progression. A fourth portion 840 may include a summary with the most therapy-driven results from the previous reports included. For example, the fourth portion may combine Alterations 92 from the Molecular Report 90 with Therapies 94 having Drug information 130 that are most likely to result in favorable outcomes for the patient according the Analytics Module 36. Drug considerations may identify which therapies are pertinent to which genes and associated genetic sequences detected in the patient, as well as provide a short summary on the interactions of the therapies with each identified gene or genetic sequence.

A fifth portion 850 may identify pharmacokinetic genes which are known (FDA approved, published and peer reviewed, or identified by Analytics Module 36) to have an effect on drug absorption as well as their expected metabolic absorptions. Pharmacokinetics is the study of how a drug is affected by the body, which includes a drug's absorption, distribution, metabolism and excretion. Differences in drug effects among patients may be influenced by genetic differences in patients' ability to respond to a drug. There have been numerous enzymes identified as important to drug metabolism. Differing phenotypes have been associated with deficient, reduced, normal, or increased activity in these enzymes leading to variable drug responses. Furthermore, a linear graph may be presented to visually identify the metabolic absorption expected based upon the gene identified along with an absorption rating such as ultra-rapid, intermediate, normal, or poor metabolization.

A sixth portion 860 may identify pharmacodynamic genes which are known to have an effect on how a drug may affect the patient as well as the expected effect the gene may cause a particular drug or therapy to have. The effects can include those manifested within a patient. The genes may be listed alongside the drug actions which may be expected such as stimulation, depression, blocking/antagonizing, stabilizing, exchanging/replacing, direct beneficial or harmful chemical reactions (summarized as S/S, G/G, Present, A/T, etc). In alternate embodiments, alternative sections may be displayed such as "Current Drugs" that may list drugs that a patient is currently taking for at-a-glance comparison with any considered drugs, "Genomic Results" encapsulating the pharmacokinetic and pharmacodynamic genes discussed above with "Metabolism Results" and "Adverse Events" field for describing the pharmacogenomic implications of the genetic variant. In another example, alternative or additional field names may be used to group or describe these pharmacogenomic implications.

FIG. 8B shows a seventh portion 870 which may identify treatments including antidepressants such as Desvenlafaxine, Levomilnacipran, etc. with a short summary including the classes of antidepressant, such as, Selective serotonin reuptake inhibitors (SSRIs), Serotonin and norepinephrine reuptake inhibitors (SNRIs), Tricyclic antidepressants (TCAs), Monoamine Oxidase Inhibitors (MAOIs), dopamine reuptake inhibitor, noradrenergic antagonist, serotonin antagonist and reuptake inhibitors (SARIs), etc. Antidepressants may be sorted according to their expected pharmacogenomic or pharmacodynamic responses and the genes which contribute to the respective response. Furthermore, Reference IDs and PubMed IDs (PMID) may be linked to each antidepressant alongside notes on what the potential pharmacogenomic implications may require, such as increasing or decreasing prescription frequency or dosage strength, side effects, or other outcomes. Reference IDs may be linked to internally curated drug databases, FDA released reports, CPIC guidelines, clinical trial reports, or reports from insurance companies or pharmacological companies. PMIDs may link to a PubMed publication relating to the identified drug and/or gene supporting the relationship between the gene and therapy. Each treatment identified may also be accompanied by a field identifying dosage guidelines or possible dosage adjustments based upon detected genetic sequence(s) of a gene or genes alone or in combination with phenotypic data or imaging data. For example, if a detected genetic sequence of a gene encoding a specific enzyme indicates a patient is a normal metabolizer, a standard administration classification may be indicated for that treatment, which may not need adjustment or for a poor metabolizer, a dose adjustment may be indicated. If two genetic sequences are detected with adverse effects on metabolism, for example, if one detected sequence of a gene indicates the patient is a poor metabolizer and the other detected sequence of the gene indicates the patient is a normal metabolizer, a contraindication may be identified to alert to physician to a potential adverse effect or harm that may recommend a dosage adjustment if applicable.

In another embodiment, Patient Report 800 may be a printed report or electronic form report such as a word document, PDF, or similar format. The report may be printed, e-mailed, delivered to a fax machine, downloaded, or saved from the GUI 50 and may further contain any data displayed in GUI 50.

Patient reports may be associated with a patient and may include a comparison of the patient's genetic sequencing information and/or other types of profiles, including molecular profiles, especially as they relate to clinical features in the patient's medical records and therapy notes, to many sets of genetic sequencing information and/or other types of profiles each associated with another patient, especially as each set relates to clinical features in that other patient's medical records and therapy notes. Patient reports may display depictions or plots showing the relationship among multiple patients, and any similarities among the patients based on genetic sequencing information and/or other types of profiles. These comparisons allow the patient report to provide clinical decision-support for depression patients and their medical providers in the context of other patient data. These comparisons may be direct, for example, comparison of one patient's clinical features to another patient's and/or multiple patients' features, or indirect, including comparisons leveraged to predict a patient's response to therapy based on aggregated data associated with multiple patients.

Patient reports may list drugs that are contraindicated for the patient, drugs and doses of each drug or other therapies that could be appropriate for therapeutic use for the patient, and warnings or information about potential drug-drug interactions. The drugs, doses, and other therapies selected for listing in the patient report may be based on data associated with the patient, including the patient's genetic sequencing results, a molecular profile including RNA or protein expression levels, the patient's medical records, therapy notes, patient-reported outcomes (PROs), similarities to other patients' sequencing information or other molecular profiles and/or reported successful treatment regimens of molecularly similar patients, evaluation results based on the Patient Health Questionnaire (PHQ-9), General Anxiety Disorder (GAD) scale, Hamilton Depression (HAM-D) Rating Scale, Clinical Global Impression (CGI) scores, Diagnostic and Statistical Manual of Mental Disorders, 5th Edition (DSM-5), etc.

System 10 may interface with mobile applications that patients use to record patient-reported outcomes (PRO's) in order to transmit information between system 10 and the mobile application. System 10 may generate or receive geographic location tracking information from a patient and may calculate location metrics including amount of time spent outside of the home and other metrics that may be correlated with severity of depression. Patient reports may include calculated location metrics and suggestions for the patient based on these metrics and/or PROs.

In some embodiments, a PRO can be any report of the status of a patient's health condition that comes directly from the patient, without interpretation of the patient's response by a clinician and/or any other person. This data may be used to measure risks/benefits of treatments, inform and guide patient-centered care and clinical decision-making. A mobile application that records PROs may provide data (e.g., patient data that can allow a clinician to automatically track patient progress and make measurement-informed decisions). In some embodiments, the mobile application can provide improved efficiency (e.g., the PRO can provide personalized evidence-based assessments to patients, including scales such as PHQ-9 with proprietary daily check-in measures, without disrupting a clinician's workflow). In some embodiments, the mobile application may automatically deliver, score, and chart the results for assessments so a clinician can spend less time filling out paperwork to track their patient's progress and outcomes. In some embodiments, the mobile application can provide insights about a patient such as tracking patient progress and translating findings into personalized treatment decisions. In some embodiments, the mobile application can generate reports embedded with patient-specific insights derived from real-world evidence to provide a clinician with data to improve patient care. In some embodiments, the mobile application can provide reimbursement information. For example, each time a patient completes an assessment through a PRO app, a clinician may be eligible to collect reimbursement from insurance without having to spend any extra time submitting claims.

In some embodiments, the mobile application can provide data for a patient. In some embodiments, the mobile application can information for patients to monitor their mental health. In some embodiments, the mobile application can provide complete, quick daily check-ins to keep track of positivity, energy, and symptoms. In some embodiments, the mobile application can provide insights into how patterns in sleep, exercise, and movement can affect how the patient feels over time. In some embodiments, the mobile application can provide a way for the patient to share symptoms and progress with a clinician to create a more personalized care experience.

In one example, a PRO GUI may report the status of a patient's health condition that comes directly from the patient. This data may be used to measure risks/benefits of treatments, inform and guide patient-centered care and clinical decision-making. A mobile application used by a patient to record PROs may permit a clinician to automatically track patient progress and make measurement-informed decisions; administer personalized evidence-based assessments to patients without disrupting a clinician's workflow; and combine scales like the PHQ-9 with periodic check-in measures. The PRO GUI may automatically deliver, score, and chart the results for these assessments. The app may facilitate tracking patient progress and translate findings into personalized treatment decisions. The report may be embedded with patient-specific insights derived from real-world evidence to empower clinicians with data to improve patient care. For a patient, the app may provide a way for patients to monitor their mental health, permit quick daily check-ins to keep track of positivity, energy, and symptoms, understand how patterns in sleep, exercise, and movement can affect how a patient feels over time, and/or share symptoms and progress with a clinician to create a more personalized care experience. Patient reports may list clinical trials for which the patient matches clinical trial inclusion criteria, and/or which are located in geographic proximity to the patient or do not require long distances of travel or relocation.

Specific examples of drugs that may be included in a patient report 800 for any reason may include, but are not limited to, the following: Abacavir, Allopurinol, Alprazolam, Amitriptyline, Amoxapine, Aripiprazole, Armodafinil, Asenapine, Atomoxetine, Brexpiprazole, Bupropion, Bupropion hydrobromide, Buspirone, Carbamazepine, Cariprazine, Chlordiazepoxide, Chlorpromazine, Citalopram, Clomipramine, Clonazepam, Clopidogrel, Clorazepate, Clozapine, Codeine, Desipramine, Desvenlafaxine, Deutetrabenazine, Dextromethorphan/quinidine, Diazepam, Doxepin, Duloxetine, Escitalopram, Esketamine, Eszopiclone, Fluoxetine, Fluoxetine, Fluphenazine, Fluvoxamine, Fluvoxamine, Gabapentin, Haloperidol, Iloperidone, Imipramine, Isocarboxazid, Lamotrigine, Levomilnacipran, Levothyroxine (may include thyroxine and/or T4), Lithium, Lorazepam, Loxapine, Lurasidone, Maprotiline, Milnacipran, Mirtazapine, Moclobemide, Modafinil, Nefazodone, Nortriptyline, Olanzapine, Ondansetron, Oxazepam, Oxcarbazepine, Oxcarbazepine, Paliperidone, Paroxetine, Paroxetine, Paroxetine, Perphenazine, Phenelzine, Phenytoin, Pimavanserin, Pimozide, Pregabalin, Propranolol, Protriptyline, Quetiapine, Ramelteon, Risperidone, Selegiline (may be transdermal), Sertraline, Sertraline, Tamoxifen, Temazepam, Tetrabenazine, Thioridazine, Thiothixene (tiotixene), Topiramate, Tranylcypromine, Trazodone, Triazolam, Trifluoperazine, Trifluoperazinea, Trimipramine, Tropisetron, Valbenazine, Valproate, Venlafaxine, Vilazodone, Voriconazole, Vortioxetine, Warfarin, Ziprasidone, Zolpidem, and Zonisamide.

FIGS. 9A-9H illustrate an alternative embodiment of Patient Report 800. In addition to sections mentioned in FIGS. 8A and 8B, Patient Report 800 may further include Summary 910, Legend 920, Pharmacogenomic Result Details 930, and Secondary Findings Details 940. Patient Report 800 may further include other notes or indications (not shown).

Summary 910 may show drugs that are most likely to be successful in ameliorating the patient's depressive or psychiatric symptoms, based on individual and/or aggregated patient data including clinical data, imaging data, behavioral data, molecular data, pharmacogenetic data, and other genetic sequences detected in the patient. Notes in a third portion 830 may include geneticist notes or notes about an incidental germline finding. The legend 920 may include the classifications used in seventh portion 870 and a brief description of each classification that guides a medical provider in interpreting the classification.

In the example shown, a seventh portion 870 may be organized by treatment type, including "antidepressants" "antipsychotics," "anticonvulsants," "anxiolytics," and "other drugs". Additional treatment types may be added to the report to identify other methods of treatment and their respective pharmacogenomic implications. Additional treatment types may include therapies such as hypnotics, or even untraditional therapies such as ayahuasca. Each treatment type may be organized by drug classes including "SSRI" "SNRI" "tetracyclic", etc. and each class may be organized into treatment classifications including "standard administration" "dose adjustment—increase" "dose adjustment—decrease" "contraindication" "alternative therapy preferred—adverse effects", etc. and individual treatments may be listed under a classification with the rationale for assigning that classification to that treatment.

The classification rationale may include a pharmacogenetic result from sequencing the patient's genome. The pharmacogenetic result may include a gene name and a phenotype indicated by genetic sequences associated with that gene detected in the patient or an allele name and the positive or negative result of detecting that allele in the patient. The pharmacogenetic result may further include an information source or reference that provides evidence supporting the relationship between the pharmacogenetic result and its effect on a treatment, including a published scientific research article, a database, published guidelines including Clinical Pharmacogenetics Implementation Consortium (CPIC) guidelines, DPWG, a government organization including the U.S. Food and Drug Administration (FDA), etc. In some aspects, therapies that may be more effective for the patient with a non-standard dose may be labeled as "dose adjustment—increase or decrease" and/or a unique marker and/or color (as shown, arrowheads pointing up and down with a blue background) for efficient identification by a medical provider. Similarly, other markers and/or colors may be used to label therapies under other classifications.

Similar to fifth and sixth portions 850 and 860, pharmacogenomic result details 930 may include one or more gene names, identifiers of the alleles associated with that gene that were detected in the patient, or a gene allele identifier (in this example, HLA-A*13:01 or HLA-B*15:02) and a presence or absence status to indicate whether that allele was detected in the patient, as well as a phenotype associated with each detected allele or the combination of detected alleles for that gene. Examples of phenotypes include poor metabolizer, intermediate metabolizer, normal metabolizer, extensive metabolizer, ultrarapid metabolizer, increased sensitivity, and increased risk. Pharmacogenomic result details 930 may also include accession numbers that identify the location of the gene according to a specific reference sequence build of the human genome, including hg19 (in this example, accession numbers are formatted as "NM . . . ").

Secondary findings details 940 may describe germline variants detected in the patient that may indicate risk for another disease or be associated with another disease. This section may include one or more gene names and may further include descriptions of the variant (c.4965C?G, p.Tyr1655*, stop gain), and accession number, and a genomic location (Chr13:32913457) associated with each listed gene or variant. This section may further include a recommendation that the patient receive genetic counseling.

In view of the above, system 10 can be used, not only to improve treatment and care for an individual patient with depression, but by combining the main pillars of healthcare data, catalyzed research can help patients yet to come.

In a first embodiment, genetic testing panels (targeted panels) may be used to analyze patient samples for the presence of certain genetic sequences or genetic variants and the results may be presented to a physician, medical professional, or other individual via the system 10, for example, in the molecular report 90. A knowledge database 40 may be provided to system 10 such that a desired gene, genetic variant, or variation may be linked to one or more pharmacogenomic interactions. The system may then compare the listing of genes, variants, alleles, or genetic variants from the sequencing report to the knowledge database 40 to generate the above reports. Furthermore, the knowledge database 40 may comprise information on any of the following panels. One or more panels may detect genetic variants in one or more genes responsible for metabolism, pharmacodynamics, and/or immunogenicity of one or more medications.

One type of panel, such as a panel directed to detecting information relevant to pharmacogenomics across many fields of medicine, may detect genetic variants in a patient sample in one or more of the following genes: CYP2C19 (NM_000769.4), CYP2D6 (NM_000106.6), CYP1A2 (NM_000761.5), CYP2B6 (NM_000767.4), CYP2C9 (NM_000771.4), CYP3A4 (NM_017460.5), HLA-A (NM_002116.8), HLA-B (NM_005514.8), HTR2A (NM_000621.4), SLC6A4 (NM_001045.5), UGT1A4 (NM_007120.2), and UGT2B15 (NM_001076.3). The locations of the exons and/or introns associated with a gene may be defined according to published database entries. A database entry may be identified by an accession number, examples of which are listed in parentheses after the name of each gene in this disclosure. In this example, the locations listed in the entries associated with these accession numbers are in accordance with human reference genome hg19.

In another example, genetic testing panels may be used to target genes of suspected interest relevant to a specific field of medicine or a specific disease state (such as depression). These panels may include an additional one or more of the following genes, in addition to genes already listed: 5HT2C (NM_000868.3), ABCB1 (MDR1) (NM_000927.4), ABCG2 (NM_004827.2), ACE (NM_000789.3), ADRA2A (NM_001076.3), ADRB1 (NM_000684.2), ADRB2 (NM_000024.5), AGT (NM_000029.4), ANK3 (NM_020987.5), ANKK1 (NM_178510.1), APOE (NM_001302688.1), BDNF (NM_001709.4), CACNA1C (NM_199460.3), CES1 (NM_001266.4), COMT (NM_000754.3), CYP1A2 (NM_000761.5), CYP2B6 (NM_000767.4), CYP2C19 (NM_000769.4), CYP2C9 (NM_000771.4), CYP2D6 (NM_000106.6), CYP3A4 (NM_017460.5), CYP3A5 (NM_000777.5), CYP4F2 (NM_001082.4), DPYD (NM_000110.3), DRD1 (NM_000794.4), DRD2 (NM_000795.3), DRD3 (NM_000796.5), EDN1 (NM_001955.4), ERCC1 (NM_202001.2), F2 (NM_000506.4), F5 (NM_000130.4), FCGR2A (NM_021642.3), FCGR3A (NM_000569.7), G6PD (NM_000402.4), GNB3 (NM_002075.3), GRIK1 (NM_000830.4), GRIK4 (NM_014619.4), GSTP1 (NM_000852.3), HLA-A (NM_002116.8), HLA-B (NM_005514.8), HNF4A (NM_178849.2), HSD3B1 (NM_000862.2), HTR1A (NM_000524.3), HTR2A (NM_000621.4), HTR2C (NM_000868.3), IFNL3 (IL28B) (NM_001346937), IFNL3 (NM_001346937.1), KCNIP1 (NM_001034837.2), KCNJ11 (NM_000525.3), KCNQ1 (NM_000218.2), LDLR (NM_000527.4), LIPC (NM_000236.2), MC4R (NM_005912.2), MTHFR (NM_005957.4), MTRR (NM_002454.2), NEUROD1 (BETA2) (NM_002500.4), NQO1 (NM_000903.3), NR1H3 (NM_00569.3), NUDT15 (NM_018283.3), OPRM1 (NM_000914.4), PAX4 (NM_006193.2), POLG (NM_002693.2), PPARA (NM_002693.2), PPARG (NM_015869.4), PPARGC1A (NM_007215.3), PRKAA1 (NM_006251.5), PRKAB2 (NM_005399.4), PTPRD (NM_005399.4), RBP4 (NM_006744.3), RYR1 (NM_000540.2), SLC22A1 (OCT1) (NM_003057.2), SLC22A2 (OCT2) (NM_003058.3), SLC30A8 (NM_173851.2), SLC47A1 (MATE1) (NM_018242.2), SLC47A2 (MATE2-K) (NM_152908.3), SLC49A4 (PMAT) (NM_032839.2), SLC6A2 (NM_001043.3), SLC6A4 (NM_001045.5), SLCO1B1 (NM_006446.4), SOD2 (NM_000636.3), STK11 (NM_000455.4), TCF7L2 (NM_030756.4), TPMT (NM_000367.4), TYMS (NM_000367.4), UCP2 (NM_003355.2), UGT1A1 (NM_000463.2), UGT1A4 (NM_007120.2), UGT1A9 (NM_021027.3), UGT2B15 (NM_001076.3), UMPS (NM_000373.3), and VKORC1 (NM_000373.3).

Still other genetic testing panels may be utilized for the purposes of developing large datasets of genetic information for research purposes such as identifying unknown biomarkers that identify pharmacogenetic responses of a patient, or biomarkers for susceptibility to a disease state such as depression. Such a panel would include one or more of the genes of Table 1, in addition to genes already listed, and may generate whole exome sequencing data that includes the genetic sequences of all exon regions in the human genome, in addition to selected intronic regions. The genetic variants detected in the patient may be matched to entries in the KDB 40 to predict the patient's response to various therapies, which may be displayed in the patient report 800 and/or GUI 50, as described above.

Specific genetic variants at a certain genomic location associated with a gene (such as SNPs at an identified locus) that are detected by these genetic testing panels, sequence analysis, microarray, or another method may be identified according to reference SNP cluster (rs) ID and/or genomic position of the genetic variant. In this example, genomic positions are based on human genome build GRCh37/hg19. In addition to the coding exons that may be analyzed by exome sequencing or another genetic sequence analysis method, specific intronic regions associated with a gene that are analyzed by these genetic testing panels, sequence analysis, or another method may be identified according to their nucleotide positions on a given chromosome.

Some genes, including CYP2C19, CYP2D6, CYP1A2, CYP2B6, CYP2C9, CYP3A4, HLA-A, HLA-B, UGT1A4, and UGT2B15 use specialized nomenclature, known as star alleles, to define their genetic variants. A star allele is a group of variants that define the allele and predict the functional outcome of the allele. In one example, *1 refers to star allele 1, which may be the normal reference allele, and *1×N refers to a gain of N copies of allele 1 compared to a normal reference genome. Any star allele copy number gain may be denoted as * #×N where #is the star allele number and N is the number of copies gained. In another example, specific alleles of a certain gene, combinations of two alleles of a certain gene (for example, which may determine or affect the patient's phenotype), and copy number changes (gains or losses) of those alleles that are detected by these genetic testing panels, sequence analysis, or another method may be defined and/or referred to by standardized identifiers, including but not limited to star allele nomenclature.

For example, specific genetic variants associated with the CYP2C19 gene may include variants that are located in the exons of the gene as well as variants identified by the following rs IDs located in the introns: rs2860840, rs1326830, rs11188072, rs11316681, rs111490789, rs17878739, rs7902257, rs11568732, rs12248560, rs4986894, rs367543001, rs17885098, rs12768009, rs17884832, rs7916649, rs17878649, rs12769205, rs17879992, rs7088784, rs72558186, rs12571421, rs12767583, rs4494250, rs4417205, rs7915414, rs28399513, rs3758581, rs4917623, and rs55640102. Specific CYP2C19 alleles may include the following CYP2C19 star alleles: *1, *1A, *1B, *1C, *2, *2A, *2B, *2C, *2D, *2E, *2F, *2G, *2H, *2J, *3, *3A, *3B, *3C, *4A, *4B, *5, *6, *7, *8, *9, *10, *12, *17, *27, *28, *34, and *35.

Specific intronic regions associated with the CYP2C19 gene may include the following nucleotide positions on chromosome 10: positions 96495132 through 96612771, and more specifically the following positions on chromosome 10: 96495132 through 96495332, 96495693 through 96495893, 96518961 through 96519161, 96520333 through 96520533, 96520343 through 96520543, 96520924 through 96521124, 96521322 through 96521522, 96521474 through 96521674, 96521557 through 96521757, 96522265 through 96522465, 96522350 through 96522550, 96522461 through 96522661, 96525765 through 96525965, 96534375 through 96534575, 96534484 through 96534684, 96534668 through 96534868, 96535024 through 96535224, 96535528 through 96535728, 96541273 through 96541473, 96541656 through 96541856, 96541882 through 96542082, 96547363 through 96547563, 96563657 through 96563857, 96580102 through 96580302, 96599410 through 96599610, 96602298 through 96602498, 96602523 through 96602723, 96609468 through 96609668, and 96612571 through 96612771.

For example, specific genetic variants associated with the CYP2D6 gene may include variants that are located in the exons of the gene as well as variants identified by the following rs IDs: rs12169962, rs28371738, rs267608322, rs28371729, rs4987144, rs267608322, rs28371730, rs2004511, rs267608292, rs28371729, rs1985842, rs267608291, rs28371725, rs28371721, rs188062577, rs79738337, rs267608300, rs267608290, rs2267447, rs3892097, rs267608305, rs67497403, rs267608306, rs267608289, rs201377835, rs28371702, rs28371701, rs575159870, rs28371699, rs267608273, rs1081000, rs28695233, rs29001518, rs1080998, rs1080997, rs1080996, rs1080995, rs75085559, rs267608272, rs1080993, rs35481113, rs35023634, rs34894147, rs35046171, rs34898711, rs35534760, rs34167214, rs530422334, rs566383351, rs28633410, rs534009571, rs28624811, rs536645539, rs1080990, rs1080989, rs59360719, rs544534350, rs375413467, rs267608271, rs28735595, rs59099247, rs28588594, rs76210340, rs1080985, rs576829306, rs545591749, rs58188898, and rs1080983. Additional specific genetic variants associated with the CYP2D6 gene may include genetic variants at the following genomic positions: Chr22:42525917, Chr22:42525946, Chr22:42527060, Chr22:42527068, Chr22:42527114, Chr22:42527115, Chr22:42527122, Chr22:42527127, and Chr22:42527422.

Specific CYP2D6 alleles may include the following CYP2D6 star alleles: *1, *1A, *1B, *1C, *1D, *1E, *1×N, *2, *2A, *2B, *2C, *2D, *2E, *2F, *2G, *2H, *2K, *2L, *2M, *2×N, *3, *3A, *3B, *3×N, *4, *4A, *4B, *4C, *4D, *4E, *4F, *4G, *4H, *4J, *4K, *4L, *4M, *4N, *4P, *4×N, *5, *6, *6A, *6B, *6C, *6D, *6×N, *7, *8, *9, *9×N, *10, *10A, *10B, *10D, *10×N, *11, *11A, *11B, *12, *13, *14A, *14B, *15, *17, *17×N, *21A, *21B, *31, *35A, *35B, *36, *36×N, *41, *41×N, *45B, *45A, *46A, *46B, *47, *49, *51, *52, *53, *56A, *56B, *58, *59, *60, *64, *68, *69, *70, *71, *72, *73, *74, *84, *85, *91, *99, *100, *101, *109, and the specific combination of *36 with *10.

Specific intronic regions associated with the CYP2D6 gene may include the following nucleotide positions on chromosome 22: positions 42522212 through 42528668, and more specifically the following positions on chromosome 22: 42522212 through 42522412, 42522292 through 42522492, 42523084 through 42523284, 42523258 through 42523458, 42522903 through 42523103, 42523084 through 42523284, 42523109 through 42523309, 42523111 through 42523311, 42523202 through 42523402, 42523258 through 42523458, 42523309 through 42523509, 42523663 through 42523863, 42523705 through 42523905, 42524032 through 42524232, 42524385 through 42524585, 42524390 through 42524590, 42524402 through 42524602, 42524564 through 42524764, 42524596 through 42524796, 42524847 through 42525047, 42525095 through 42525295, 42525180 through 42525380, 42525199 through 42525399, 42525633 through 42525833, 42525812 through 42526012, 42525817 through 42526017, 42525846 through 42526046, 42525852 through 42526052, 42525949 through 42526149, 42526088 through 42526288, 42526384 through 42526584, 42526414 through 42526614, 42526449 through 42526649, 42526461 through 42526661, 42526462 through 42526662, 42526467 through 42526667, 42526471 through 42526671, 42526473 through 42526673, 42526480 through 42526680, 42526736 through 42526936, 42526831 through 42527031, 42526869 through 42527069, 42526918 through 42527118, 42526925 through 42527125, 42526960 through 42527160, 42526964 through 42527164, 42526968 through 42527168, 42526968 through 42527168, 42527014 through 42527214, 42527015 through 42527215, 42527020 through 42527220, 42527022 through 42527222, 42527024 through 42527224, 42527027 through 42527227, 42527047 through 42527247, 42527124 through 42527324, 42527322 through 42527522, 42527371 through 42527571, 42527385 through 42527585, 42527433 through 42527633, 42527442 through 42527642, 42527653 through 42527853, 42527693 through 42527893, 42527704 through 42527904, 42527686 through 42527986, 42527802 through 42528002, 42527928 through 42528128, 42527996 through 42528196, 42528124 through 42528324, 42528241 through 42528441, 42528282 through 42528482, 42528298 through 42528498, 42528299 through 42528499, 42528438 through 42528638, and 42528468 through 42528668.

For example, specific genetic variants associated with the CYP1A2 gene may include variants that are located in the exons of the gene as well as variants identified by the following rs IDs: rs2472299, rs2069514, rs35694136, rs2069526, rs12720461, rs762551, rs2069526, rs28399417, rs12720461, rs183165301, rs762551, rs4646425, rs2472304, rs3743484, rs56107638, and rs4646427. Additional specific genetic variants associated with the CYP1A2 gene may include genetic variants at the following genomic positions: Chr15:75038486, Chr15:75038967, Chr15:75039027, Chr15:75039272, Chr15:75039413, Chr15:75041341, Chr15:75041713, Chr15:75042757, Chr15:75044104, and Chr15:75047284. Specific CYP1A2 alleles may include the following CYP1A2 star alleles: *1, *1E, *1F, *1G, *1J, *1K, *1L, *1M, *1N, *1P, *1Q, *1R, *1V, *1W, *3, *4, *6, *7, *8, *11, *15, *16, *17, and *21.

Specific intronic regions associated with the CYP1A2 gene may include the following nucleotide positions on chromosome 15: 75033300 through 75047384, and more specifically the following positions on chromosome 15: 75033300 through 75033500, 75038120 through 75038320, 75038386 through 75038586, 75038867 through 75039067, 75038927 through 75039127, 75039172 through 75039372, 75039313 through 75039513, 75039513 through 75039713, 75041241 through 75041441, 75041241 through 75041441, 75041251 through 75041451, 75041613 through 75041813, 75041817 through 75042017, 75041241 through 75041441, 75041247 through 75041447, 75041251 through 75041451, 75041613 through 75041813, 75041817 through 75042017, 75042657 through 75042857, 75043181 through 75043381, 75044004 through 75044204, 75044138 through 75044338, 75044300 through 75044500, 75045512 through 75045712, 75045592 through 75045792, 75047184 through 75047384.

For example, specific genetic variants associated with the CYP2B6 gene may include variants that are located in the exons of the gene as well as variants identified by the following rs IDs: rs1962261, rs2054675, rs4802101, rs34223104, rs28399484, rs3786547, rs2279342, rs28969408, rs4803418, rs28399487, rs28399488, rs28399490, rs4803419, rs28399491, rs35266616, rs28399492, rs202050252, rs34155858, rs2279344, rs2279345, rs8192718, rs12721649, rs28399498, rs35622401, rs8192719, rs7260329, rs8109848, rs28399502, rs28969419, rs28969420, and rs12979898.

Additional specific genetic variants associated with the CYP2B6 gene may include genetic variants at the following genomic positions: Chr19:41494891, Chr19:41495363, Chr19:41495433, Chr19:41495633, Chr19:41495987, Chr19:41496025, Chr19:41496410, Chr19:41496454, and Chr19:41496620.

Specific CYP2B6 alleles may include the following CYP2B6 star alleles: *1, *1A, *1B, *1C, *1D, *1E, *1F, *1G, *1H, *1J, *1K, *1L, *1M, *1N, *4, *4A, *4B, *4C, *4D, *5B, *6, *6A, *6B, *6C, *7B, *9, *11B, *12, *13A, *13B, *14, *15A, *15B, *17A, *17B, *18, *19, *20, *21, *22, *27, *28, *34, *35, *36, *38.

Specific intronic regions associated with the CYP2B6 gene may include the following nucleotide positions on chromosome 19: 41494791 through 41524232, and more specifically the following positions on chromosome 19: 41494791 through 41494991, 41495139 through 41495339, 41495263 through 41495463, 41495333 through 41495533, 41495533 through 41495733, 41495655 through 41495855, 41495887 through 41496087, 41495925 through 41496125, 41496310 through 41496510, 41496354 through 41496554, 41496361 through 41496561, 41496520 through 41496720, 41497029 through 41497229, 41497407 through 41497607, 41506091 through 41506291, 41510027 through 41510227, 41510308 through 41510508, 41511703 through 41511903, 41512524 through 41512724, 41512525 through 41512725, 41512687 through 41512887, 41512692 through 41512892, 41512904 through 41513104, 41512947 through 41513147, 41514632 through 41514832, 41514918 through 41515118, 41515276 through 41515476, 41515383 through 41515583, 41515602 through 41515802, 41515714 through 41515914, 41515737 through 41515937, 41515784 through 41515984, 41516022 through 41516222, 41518673 through 41518873, 41521538 through 41521738, 41521969 through 41522169, 41522770 through 41522970, 41523257 through 41523457, 41523704 through 41523904, and 41524032 through 41524232.

For example, specific genetic variants associated with the CYP2C9 gene may include variants that are located in the exons of the gene as well as variants identified by the following rs IDs: rs146705863, rs9332092, rs9332093, rs9332094, rs9332096, rs61604699, rs4918758, rs4917636, rs9332098, rs9332100, rs9332101, rs9332102, rs9332104, rs12772884, rs9332116, rs9332119, rs9332120, rs2860905, rs28371675, rs28371676, rs28371677, rs28371679, rs28371680, rs28371681, rs28371682, rs4086116, rs9332127, rs28371683, rs9332129, rs28371684, rs4917639, rs9332172, rs9332174, rs10509680, rs9332197, rs17847029, rs9332230, rs9332232, rs2298037, rs9332238, rs1934969, rs146139873, and rs57749228. Additional specific genetic variants associated with the CYP2C9 gene may include genetic variants at the following genomic positions: Chr10: 96709253. Specific CYP2C9 alleles may include the following CYP2C9 star alleles: *1, *2, *3, *4, *5, and *6.

Specific intronic regions associated with the CYP2C9 gene may include the following nucleotide positions on chromosome 10: 96695677 through 96748620, and more specifically the following positions on chromosome 10: 96695677 through 96695877, 96696429 through 96696629, 96696455 through 96696555, 96696574 through 96696774, 96696775 through 96696975, 96696803 through 96697003, 96697152 through 96697352, 96697244 through 96697444, 96697359 through 96697559, 96697720 through 96697920, 96697855 through 96698055, 96697856 through 96698056, 96698590 through 96698790, 96700530 through 96700730, 96700679 through 96700879, 96701501 through 96701701, 96701750 through 96701950, 96702195 through 96702395, 96702237 through 96702437, 96702263 through 96702463, 96702372 through 96702572, 96702496 through 96702696, 96702648 through 96702848, 96702967 through 96703167, 96703009 through 96703209, 96707102 through 96707302, 96707371 through 96707571, 96707408 through 96707608, 96708650 through 96708850, 96709021 through 96709221, 96709153 through 96709353, 96725435 through 96725635, 96731688 through 96731888, 96731997 through 96732197, 96734239 through 96734439, 96740808 through 96741008, 96741065 through 96741265, 96745884 through 96746084, 96745932 through 96746132, 96745978 through 96746178, 96748392 through 96748592, 96748395 through 96748595, 96748405 through 96748605, 96748420 through 96748620.

For example, specific genetic variants associated with the CYP3A4 gene may include variants that are located in the exons of the gene as well as variants identified by the following rs IDs: rs59715127, rs72552794, rs3735451, rs6956344, rs4646440, rs2242480, rs56153749, rs4646437, rs2246709, rs2687116, rs55808838, rs35599367, rs68106838, rs72552800, rs12721636, and rs2740574. Additional specific genetic variants associated with the CYP3A4 gene may include genetic variants at the following genomic positions: Chr7:99364921, Chr7:99365083, Chr7:99365719, Chr7:99365887, Chr7:99365943, Chr7:99365969, Chr7:99366316, Chr7:99367496, Chr7:99375629, Chr7:99381766, Chr7:99381766, Chr7:99381860, Chr7:99382073, Chr7:99382096, Chr7:99382148, Chr7:99382334, Chr7:99382359, Chr7:99382451, and Chr7:99382539. Specific CYP3A4 alleles may include the following CYP3A4 star alleles: *1, *1B, *13, *15A, *15B, *22, *23, and *24.

Specific intronic regions associated with the CYP3A4 gene may include the following nucleotide positions on chromosome 7: 99355390 through 99382640 and more specifically the following positions on chromosome 7: 99355390 through 99355590, 99355583 through 99355783, 99355875 through 99356075, 99359051 through 99359251, 99360770 through 99360970, 99361366 through 99361566, 99363780 through 99363980, 99364821 through 99365021, 99364983 through 99365183, 99365619 through 99365819, 99365787 through 99365987, 99365843 through 99366043, 99365869 through 99366069, 99366216 through 99366416, 99367396 through 99367596, 99375529 through 99375729, 99381666 through 99381866, 99381666 through 99381866, 99381760 through 99381960, 99381973 through 99382173, 99381996 through 99382196, 99382048 through 99382248, 99382234 through 99382434, 99382259 through 99382459, 99382351 through 99382551, 99382440 through 99382640.

For example, specific genetic variants associated with the HLA-A gene may include variants that are located in the exons of the gene as well as variants identified by the following rs IDs: rs3823339, rs1061235, and rs2499. Specific intronic regions associated with the HLA-A gene may include the following nucleotide positions on chromosome 6: 29912868 through 29913642, and more specifically the following positions on chromosome 6: 29912868 through 29913068, 29913198 through 29913398, and 29913442 through 29913642.

For example, specific genetic variants associated with the HLA-B gene may include variants that are located in the exons of the gene as well as variants identified by the following rs IDs: rs13203895, rs2074488, rs2524074, rs2524084, rs2844613, rs28498059, rs13218306, rs12199223, rs9366775, rs9357121, rs4361609, rs2524082, rs12111032, rs2844619, rs2524078, rs3134745, rs6913377, rs7759127, rs6923313, rs10456057, rs12189871, rs12191877, rs16899160, rs16899166, rs16899168, rs2394963, rs2524043, rs2524044, rs2524048, rs2524051, rs2524057, rs2524070, rs2524156, rs2853929, rs2853933, rs2853935, rs2853939, rs3873374, rs3873375, rs6457372, rs6906846, rs7382297, rs7754443, rs9366776, rs9378228, rs9380236, rs9461684, rs9468920, rs9468922, rs9468925, rs9468926, rs2844599, rs9348859, rs2853934, rs2524049, rs2524069, rs9391714, rs2853948, rs7381988, rs9348862, rs2524163, rs2524040, rs10081114, rs10484554, rs12664384, rs16899178, rs16899203, rs16899205, rs16899207, rs16899208, rs2243868, rs2246954, rs2247056, rs2394967, rs2508004, rs2524066, rs2524089, rs2524095, rs2524115, rs2524123, rs2524132, rs2524145, rs2524168, rs2853923, rs2853925, rs2853926, rs28894983, rs28894990, rs3094682, rs3094691, rs364415, rs3873379, rs3873386, rs3905495, rs396038, rs396243, rs396337, rs4406273, rs4523128, rs4543367, rs6905036, rs6918048, rs7750269, rs7760988, rs7761965, rs9264848, rs9264850, rs9264869, rs9264899, rs9264916, rs9264917, rs9264942, rs9357123, rs9366778, rs9368677, rs9380238, rs9380240, rs9461685, rs9468942, rs2894207, rs3915971, rs9295970, rs9264904, rs6457375, rs28732109, rs9348863, rs9468929, rs16899202, rs9394054, rs3873385, rs9368673, rs9368680, rs1634761, rs9264951, rs2524229, rs9264902, rs6457374, rs16867947, rs28894993, rs9295976, rs7755852, rs2156875, rs2507997, rs2596501, rs2596503, rs3134792, rs4394275, rs4540292, rs9295984, rs2844586, rs4394274, and rs2523619.

Specific intronic regions associated with the HLA-B gene may include the following nucleotide positions on chromosome 6: 31243982 through 31318244, and more specifically the following positions on chromosome 6: 31243982 through 31244182, 31240331 through 31240531, 31243921 through 31244121, 31241539 through 31241739, 31243746 through 31243946, 31240253 through 31240453, 31240832 through 31241032, 31242631 through 31242831, 31239996 through 31240196, 31240379 through 31240579, 31240535 through 31240735, 31241661 through 31241861, 31242091 through 31242291, 31242123 through 31242323, 31242549 through 31242749, 31242662 through 31242862, 31243395 through 31243595, 31240888 through 31241088, 31241270 through 31241470, 31245434 through 31245634, 31251824 through 31252024, 31252825 through 31253025, 31256567 through 31256767, 31257996 through 31258196, 31258587 through 31258787, 31251362 through 31251562, 31256912 through 31257112, 31256653 through 31256853, 31256461 through 31256661, 31255400 through 31255600, 31251795 through 31251995, 31244420 through 31244620, 31260297 through 31260497, 31255334 through 31255534, 31253988 through 31254188, 31253778 through 31253978, 31250542 through 31250742, 31251211 through 31251411, 31251260 through 31251460, 31247021 through 31247221, 31245636 through 31245836, 31246967 through 31247167, 31254163 through 31254363, 31256530 through 31256730, 31246271 through 31246471, 31254564 through 31254764, 31253344 through 31253544, 31254836 through 31255036, 31255186 through 31255386, 31258737 through 31258937, 31260118 through 31260318, 31255905 through 31256105, 31249877 through 31250077, 31253828 through 31254028, 31255853 through 31256053, 31244689 through 31244889, 31244980 through 31245180, 31245473 through 31245673, 31246603 through 31246803, 31252647 through 31252847, 31259479 through 31259679, 31257525 through 31257725, 31271369 through 31271569, 31274455 through 31274655, 31272792 through 31272992, 31261037 through 31261237, 31266235 through 31266435, 31266261 through 31266461, 31266287 through 31266487, 31267396 through 31267596, 31261176 through 31261376, 31265162 through 31265362, 31265390 through 31265590, 31269029 through 31269229, 31273495 through 31273695, 31269054 through 31269254, 31266422 through 31266622, 31266017 through 31266217, 31265454 through 31265654, 31265214 through 31265414, 31264812 through 31265012, 31268647 through 31268847, 31275063 through 31275263, 31265637 through 31265837, 31264822 through 31265022, 31262951 through 31263151, 31263540 through 31263740, 31264219 through 31264419, 31264361 through 31264561, 31274593 through 31274793, 31273124 through 31273324, 31262069 through 31262269, 31273645 through 31273845, 31265439 through 31265639, 31272880 through 31273080, 31275074 through 31275274, 31272815 through 31273015, 31265990 through 31266190, 31269282 through 31269482, 31266667 through 31266867, 31273046 through 31273246, 31268329 through 31268529, 31271057 through 31271257, 31272930 through 31273130, 31273395 through 31273595, 31271095 through 31271295, 31271140 through 31271340, 31271530 through 31271730, 31272321 through 31272521, 31272674 through 31272874, 31272708 through 31272908, 31274280 through 31274480, 31262769 through 31262969, 31269073 through 31269273, 31272221 through 31272421, 31267518 through 31267718, 31268732 through 31268932, 31265255 through 31265455, 31274341 through 31274541, 31263651 through 31263851, 31269248 through 31269448, 31269422 through 31269622, 31272453 through 31272653, 31272512 through 31272712, 31263197 through 31263397, 31262361 through 31262561, 31263116 through 31263316, 31266199 through 31266399, 31268480 through 31268680, 31269208 through 31269408, 31271657 through 31271857, 31272744 through 31272944, 31273927 through 31274127, 31275000 through 31275200, 31275131 through 31275331, 31272406 through 31272606, 31272161 through 31272361, 31280723 through 31280923, 31289614 through 31289814, 31281670 through 31281870, 31277888 through 31278088, 31317247 through 31317447, 31314681 through 31314881, 31321111 through 31321311, 31320710 through 31320910, 31312226 through 31312426, 31318077 through 31318277, 31317082 through 31317282, 31317597 through 31317797, 31317924 through 31318124, 31318064 through 31318264, 31318044 through 31318244.

For example, specific genetic variants associated with the HTR2A gene may include variants that are located in the exons of the gene as well as variants identified by the following rs IDs: rs9567733, rs7997012, rs2274639, rs9316233, rs659734, rs1928040, rs9567746, rs17288723, rs6312, and rs6311. Specific HTR2A alleles may include the following: reference allele, −1438A>G, and 102T>C. Specific intronic regions associated with the HTR2A gene may include the following nucleotide positions on chromosome 13: 47401235 through 47471578 and more specifically the following positions on chromosome 13: 47401235 through 47401435, 47411885 through 47412085, 47430163 through 47430363, 47433255 through 47433455, 47435183 through 47435383, 47447136 through 47447336, 47456448 through 47456648, 47457593 through 47457793, 47470724 through 47470924, 47471378 through 47471578.

For example, specific genetic variants associated with the SLC6A4 gene may include variants that are located in the exons of the gene as well as variants identified by the following rs IDs: rs774676466, rs1042173, rs140700, rs57098334, rs2020933, and rs25531. Specific SLC6A4 alleles may include the following: Long (L) and Short (S).

Specific intronic regions associated with the SLC6A4 gene may include the following nucleotide positions on chromosome 17: 28564227 through 28564446 and more specifically the following positions on chromosome 17: 28564227 through 28564427, 28524911 through 28525111, 28543289 through 28543489, 28548496 through 28548696, 28561655 through 28561855, 28564246 through 28564446.

For example, specific genetic variants associated with the UGT1A4 gene may include variants that are located in the exons of the gene as well as variants identified by the following rs IDs: rs3732219, rs3732218, rs2011219, rs1983023, rs45507691, rs3806596, rs3806597, rs2008595, rs10929302, rs2003569, rs60469444, rs34531096, rs76063448, rs4124874, rs3755319, rs11568318, rs11568316, rs1976391, rs4148327, rs873478, rs3213726, rs2302538, rs887829, rs34650714, rs8175347, rs10929303, rs1042640, rs8330, and rs34942353. Additional specific genetic variants associated with the UGT1A4 gene may include genetic variants at the following genomic positions: Chr2:234656479, Chr2:234675628, Chr2:234675608. Specific UGT1A4 alleles may include the following UGT1A4 star alleles: *1a, *3a, and *3b.

Specific intronic regions associated with the UGT1A4 gene may include the following nucleotide positions on chromosome 2: 234627148 through 234681724, and more specifically the following positions on chromosome 2: 234627148 through 234627348, 234627204 through 234627404, 234628276 through 234628476, 234636922 through 234637122, 234637120 through 234637320, 234637607 through 234637807, 234637469 through 234637669, 234637092 through 234637292, 234665682 through 234665882, 234667837 through 234668037, 234652540 through 234652740, 234665491 through 234665691, 234656379 through 234656579, 234652542 through 234652742, 234665559 through 234665759, 234667482 through 234667682, 234665398 through 234665598, 234665437 through 234665637, 234665883 through 234666083, 234675726 through 234675926, 234675528 through 234675728, 234668770 through 234668970, 234675423 through 234675623, 234675508 through 234675708, 234676313 through 234676513, 234668470 through 234668670, 234675729 through 234675929, 234668781 through 234668981, 234681316 through 234681516, 234681444 through 234681644, 234681545 through 234681745, 234681524 through 234681724.

For example, specific genetic variants associated with the UGT2B15 gene may include variants that are located in the exons of the gene as well as variants identified by the following rs IDs: rs4148271, rs72551389, and rs3100. Specific UGT2B15 alleles may include the following UGT2B15 star alleles: *1, and *2. Specific intronic regions associated with the UGT2B15 gene may include the following nucleotide positions on chromosome 4: 69512537 through 69512754, and more specifically the following positions on chromosome 4: 69512537 through 69512737, 69512591 through 69512791, 69512554 through 69512754.

For example, specific genetic variants associated with the ANK3 gene may include variants that are located in the exons of the gene as well as variants identified by the following rs IDs: rs12357206, and rs7911953. Specific intronic regions associated with the ANK3 gene may include the following nucleotide positions on chromosome 10: 61790283 through 61791139 and more specifically the following positions on chromosome 10: 61790283 through 61790483, 61790939 through 61791139.

For example, specific genetic variants associated with the ADRA2A gene may include variants that are located in the exons of the gene as well as variants identified by the following rs IDs: rs1800545. Specific intronic regions associated with the ADRA2A gene may include the following nucleotide positions on chromosome 10: 112837438 through 112837638.

For example, specific genetic variants associated with the BDNF gene may include variants that are located in the exons of the gene as well as variants identified by the following rs IDs: rs7124442, rs11030104, rs7103411, rs962369, and rs7934165. Specific intronic regions associated with the BDNF gene may include the following nucleotide positions on chromosome 11: 27676941 through 27732083 and more specifically the following positions on chromosome 11: 27676941 through 27677141, 27684417 through 27684617, 27700025 through 27700225, 27734320 through 27734520, 27731883 through 27732083.

For example, specific genetic variants associated with the CACNA1C gene may include variants that are located in the exons of the gene as well as variants identified by the following rs IDs: rs10848615, rs2238032, rs10848635, rs1006737, rs2239050, rs216013, and rs2239128. Specific intronic regions associated with the CACNA1C gene may include the following nucleotide positions on chromosome 12: 2218995 through 2757869, and more specifically the following positions on chromosome 12: 2218995 through 2219195, 2222632 through 2222832, 2316095 through 2316295, 2345195 through 2345395, 2447314 through 2447514, 2729532 through 2729732, 2757669 through 2757869.

For example, specific genetic variants associated with the CES1 gene may include variants that are located in the exons of the gene as well as variants identified by the following rs IDs: rs3815583. Specific intronic regions associated with the CES1 gene may include the following nucleotide positions on chromosome 16: 55866942 through 55867142.

For example, specific genetic variants associated with the COMT gene may include variants that are located in the exons of the gene as well as variants identified by the following rs IDs: rs6269, rs2239393, rs933271, rs737865, rs737866, rs4646312, rs5746849, rs4646316, rs9332377, rs174699, rs740603, rs165599, and rs165728. Specific intronic regions associated with the COMT gene may include the following nucleotide positions on chromosome 22: 19949852 through 19957123 and more specifically the following positions on chromosome 22: 19949852 through 19950052, 19950328 through 19950528, 19931307 through 19931507, 19930021 through 19930221, 19930009 through 19930209, 19948237 through 19948437, 19942897 through 19943097, 19952032 through 19952232, 19955592 through 19955792, 19954358 through 19954558, 19945077 through 19945277, 19956681 through 19956881, and 19956923 through 19957123.

For example, specific genetic variants associated with the CYP3A5 gene may include variants that are located in the exons of the gene as well as variants identified by the following rs IDs: rs15524, rs28365094, rs17161788, rs4646453, rs55965422, rs776746, rs28365095, rs28371764, rs2740565, rs55798860, and rs28451617. Specific intronic regions associated with the CYP3A5 gene may include the following nucleotide positions on chromosome 7: 99245814 through 99332865, and more specifically the following positions on chromosome 7: 99245814 through 99246014, 99250375 through 99250575, 99245809 through 99246009, 99260262 through 99260462, 99264473 through 99264673, 99270439 through 99270639, 99277505 through 99277705, 99277493 through 99277693, 99293375 through 99293575, 99332707 through 99332907, and 99332665 through 99332865.

For example, specific genetic variants associated with the CYP4F2 gene may include variants that are located in the exons of the gene as well as variants identified by the following rs IDs: rs3093158. Specific intronic regions associated with the CYP4F2 gene may include the following nucleotide positions on chromosome 19: 16000066 through 16000266.

For example, specific genetic variants associated with the DPYD gene may include variants that are located in the exons of the gene as well as variants identified by the following rs IDs: rs1760217, rs1413241, rs72728438, rs12022243, rs7548189, rs3918290, rs17116806, rs75017182, rs115632870, and rs4970722. Specific intronic regions associated with the DPYD gene may include the following nucleotide positions on chromosome 1: 97602894 through 98352153, and more specifically the following positions on chromosome 1: 97602894 through 97603094, 97722572 through 97722772, 97847774 through 97847974, 97862680 through 97862880, 97867613 through 97867813, 97915514 through 97915714, 97973152 through 97973352, 98045349 through 98045549, 98293721 through 98294921, and 98351953 through 98352153.

For example, specific genetic variants associated with the DRD1 gene may include variants that are located in the exons of the gene as well as variants identified by the following rs IDs: rs265981, rs686, and rs4532. Specific intronic regions associated with the DRD1 gene may include the following nucleotide positions on chromosome 5: 174870802 through 174870250, and more specifically the following positions on chromosome 5: 174870802 through 174871002, 174868600 through 174868800, 174870050 through 174870250.

For example, specific genetic variants associated with the DRD2 gene may include variants that are located in the exons of the gene as well as variants identified by the following rs IDs: rs1124493, rs2283265, rs2440390, rs2734841, rs1076560, rs1110976, rs12363125, rs6279, rs2734833, rs1125394, rs1079598, rs4436578, rs4460839, rs4648317, rs1799978, and rs1799732. Specific intronic regions associated with the DRD2 gene may include the following nucleotide positions on chromosome 11: 113282195 through 113346351, and more specifically the following positions on chromosome 11: 113282195 through 113282395, 113285436 through 113285636, 113286778 through 113286978, 113281676 through 113281876, 113283588 through 113283788, 113284419 through 113284619, 113285816 through 113286016, 113280973 through 113281173, 113292820 through 113293020, 113297085 through 113297285, 113296174 through 113296374, 113306665 through 113306865, 113321696 through 113321896, 113331432 through 113331632, 113346251 through 113346451, and 113346151 through 113346351.

For example, specific genetic variants associated with the DRD3 gene may include variants that are located in the exons of the gene as well as variants identified by the following rs IDs: rs963468, rs167771, rs167770, and rs324026. Specific intronic regions associated with the DRD3 gene may include the following nucleotide positions on chromosome 3: 113862787 through 113891142, and more specifically the following positions on chromosome 3: 113862787 through 113862987, 113876175 through 113876375, 113879462 through 113879662, 113890942 through 113891142.

For example, specific genetic variants associated with the ERCC1 gene may include variants that are located in the exons of the gene as well as variants identified by the following rs IDs: rs3212948, rs2276469, and rs2276470. Specific intronic regions associated with the ERCC1 gene may include the following nucleotide positions on chromosome 19: 45924262 through 45974768, and more specifically the following positions on chromosome 19: 45924262 through 45924462, 45974493 through 45974693, and 45974568 through 45974768.

For example, specific genetic variants associated with the F2 gene may include variants that are located in the exons of the gene as well as variants identified by the following rs IDs: rs1799963. Specific intronic regions associated with the F2 gene may include the following nucleotide positions on chromosome 11: 46760955 through 46761155.

For example, specific genetic variants associated with the F5 gene may include variants that are located in the exons of the gene as well as variants identified by the following rs IDs: rs3766117. Specific intronic regions associated with the F5 gene may include the following nucleotide positions on chromosome 1: 169527756 through 169527956.

For example, specific genetic variants associated with the GNB3 gene may include variants that are located in the exons of the gene as well as variants identified by the following rs IDs: rs11064426, and rs2301339. Specific intronic regions associated with the GNB3 gene may include the following nucleotide positions on chromosome 12: 6953157 through 6954724, and more specifically the following positions on chromosome 12: 6953157 through 6953357, 6954524 through 6954724.

For example, specific genetic variants associated with the GRIK1 gene may include variants that are located in the exons of the gene as well as variants identified by the following rs IDs: rs2832407. Specific intronic regions associated with the GRIK1 gene may include the following nucleotide positions on chromosome 21: 30967408 through 30967608.

For example, specific genetic variants associated with the GRIK4 gene may include variants that are located in the exons of the gene as well as variants identified by the following rs IDs: rs11601979, rs1954787, and rs12800734. Specific intronic regions associated with the GRIK4 gene may include the following nucleotide positions on chromosome 11: 120476890 through 120836854, and more specifically the following positions on chromosome 11: 120476890 through 120477090, 120663263 through 120663463, and 120836654 through 120836854.

For example, specific genetic variants associated with the GSTP1 gene may include variants that are located in the exons of the gene as well as variants identified by the following rs IDs: rs8191439. Specific intronic regions associated with the GSTP1 gene may include the following nucleotide positions on chromosome 11: 67351197 through 67351397.

For example, specific genetic variants associated with the HNF4A gene may include variants that are located in the exons of the gene as well as variants identified by the following rs IDs: rs4812831, rs1800963, rs2071197, rs3212198, rs3212200, rs2273618, rs6103731, rs6130615, rs3818247, and rs3746574. Specific intronic regions associated with the HNF4A gene may include the following nucleotide positions on chromosome 20: 43018160 through 43058118, and more specifically the following positions on chromosome 20: 43018160 through 43018360, 43029185 through 43029385, 43030335 through 43030535, 43044262 through 43044462, 43046829 through 43047029, 43052470 through 43052670, 43047193 through 43047393, 43059337 through 43059537, 43057380 through 43057580, 43057918 through 43058118.

For example, specific genetic variants associated with the HTR1A gene may include variants that are located in the exons of the gene as well as variants identified by the following rs IDs: rs1364043, rs1423691, rs6295, and rs10042486. Specific intronic regions associated with the HTR1A gene may include the following nucleotide positions on chromosome 5: 63250751 through 63261429, and more specifically the following positions on chromosome 5: 63250751 through 63250951, 63251562 through 63251762, 63258465 through 63258665, and 63261229 through 63261429.

For example, specific genetic variants associated with the HTR2C gene may include variants that are located in the exons of the gene as well as variants identified by the following rs IDs: rs3813928, rs3813929, rs518147, and rs1414334. Specific intronic regions associated with the HTR2C gene may include the following nucleotide positions on chromosome X: 113818182 through 114138244, and more specifically the following positions on chromosome X: 113818182 through 113818382, 113818420 through 113818620, 113818482 through 113818682, 114138044 through 114138244.

For example, specific genetic variants associated with the IFNL3 gene may include variants that are located in the exons of the gene as well as variants identified by the following rs IDs: rs11881222. Specific intronic regions associated with the IFNL3 gene may include the following nucleotide positions on chromosome 19: 39734823 through 39735023.

For example, specific genetic variants associated with the IFNL4 gene may include variants that are located in the exons of the gene as well as variants identified by the following rs IDs: rs12979860, and rs8099917. Specific intronic regions associated with the IFNL4 gene may include the following nucleotide positions on chromosome 19: 39738687 through 39743265 and more specifically the following positions on chromosome 19: 39738687 through 39738887, and 39743065 through 39743265.

For example, specific genetic variants associated with the KCNQ1 gene may include variants that are located in the exons of the gene as well as variants identified by the following rs IDs: rs757092, rs58762055, rs2237892, and rs2237895. Specific intronic regions associated with the KCNQ1 gene may include the following nucleotide positions on chromosome 11: 2499078 through 2857294 and more specifically the following positions on chromosome 11: 2499078 through 2499278, 2738847 through 2739047, 2839651 through 2839851, and 2857094 through 2857294.

For example, specific genetic variants associated with the LDLR gene may include variants that are located in the exons of the gene as well as variants identified by the following rs IDs: rs6511720, rs14158, rs7254521, rs5742911, rs2569537, and rs1433099. Specific intronic regions associated with the LDLR gene may include the following nucleotide positions on chromosome 19: 11202206 through 11242758, and more specifically the following positions on chromosome 19: 11202206 through 11202406, 11241944 through 11242144, 11243322 through 11243522, 11243345 through 11243545, 11239953 through 11240153, and 11242558 through 11242758.

For example, specific genetic variants associated with the MTHFR gene may include variants that are located in the exons of the gene as well as variants identified by the following rs IDs: rs786204005, rs1476413, rs17421511, and rs17367504. Specific intronic regions associated with the MTHFR gene may include the following nucleotide positions on chromosome 1: 11852200 through 11862878 and more specifically the following positions on chromosome 1: 11852200 through 11852400, 11857688 through 11857888, 11862678 through 11862878, and 11863113 through 11863313.

For example, specific genetic variants associated with the NQO1 gene may include variants that are located in the exons of the gene as well as variants identified by the following rs IDs: rs1050873, rs3191214, rs10517, and rs1063556. Specific intronic regions associated with the NQO1 gene may include the following nucleotide positions on chromosome 16: 69744674 through 69744847, and more specifically the following positions on chromosome 16: 69744674 through 69744874, 69744755 through 69744955, 69743660 through 69743860, 69744647 through 69744847.

For example, specific genetic variants associated with the NR1H3 gene may include variants that are located in the exons of the gene as well as variants identified by the following rs IDs: rs11039149. Specific intronic regions associated with the NR1H3 gene may include the following nucleotide positions on chromosome 11: 47276575 through 47276775.

For example, specific genetic variants associated with the OPRM1 gene may include variants that are located in the exons of the gene as well as variants identified by the following rs IDs: rs510769, rs3778151, rs9479757, rs558025, rs544093, and rs2281617. Specific intronic regions associated with the OPRM1 gene may include the following nucleotide positions on chromosome 6: 154361919 through 154487521 and more specifically the following positions on chromosome 6: 154361919 through 154362119, 154393580 through 154393780, 154411244 through 154411444, 154441865 through 154442065, 154457393 through 154457593, and 154487321 through 154487521.

For example, specific genetic variants associated with the PPARA gene may include variants that are located in the exons of the gene as well as variants identified by the following rs IDs: rs4253728, rs4823613, rs9626730, rs135550, and rs4253778. Specific intronic regions associated with the PPARA gene may include the following nucleotide positions on chromosome 22: 46609967 through 46630734, and more specifically the following positions on chromosome 22: 46609967 through 46610167, 46598207 through 46598407, 46562083 through 46562283, 46553134 through 46553334, and 46630534 through 46630734.

For example, specific genetic variants associated with the PPARG gene may include variants that are located in the exons of the gene as well as variants identified by the following rs IDs: rs7627605. Specific intronic regions associated with the PPARG gene may include the following nucleotide positions on chromosome 3: 12399170 through 12399370.

For example, specific genetic variants associated with the PTPRD gene may include variants that are located in the exons of the gene as well as variants identified by the following rs IDs: rs1500318, rs10977204, rs77455504, rs1333111, rs10816196, rs12004295, rs424301, rs439467, and rs1535661. Specific intronic regions associated with the PTPRD gene may include the following nucleotide positions on chromosome 9: 8361345 through 10369468 and more specifically the following positions on chromosome 9: 8361345 through 8361545, 8561442 through 8561642, 8821581 through 8821781, 9416862 through 9417062, 9829154 through 9829354, 9926419 through 9926619, 10098443 through 10098643, 10102803 through 10103003, and 10369268 through 10369468.

For example, specific genetic variants associated with the SLC22A1 gene may include variants that are located in the exons of the gene as well as variants identified by the following rs IDs: rs461473, rs35854239, and rs622342. Specific intronic regions associated with the SLC22A1 gene may include the following nucleotide positions on chromosome 6: 160543462 through 160572966, and more specifically the following positions on chromosome 6: 160543462 through 160543662, 160560808 through 160561008, and 160572766 through 160572966.

For example, specific genetic variants associated with the SLC47A1 gene may include variants that are located in the exons of the gene as well as variants identified by the following rs IDs: rs2289669. Specific intronic regions associated with the SLC47A1 gene may include the following nucleotide positions on chromosome 17: 19463243 through 19463443.

For example, specific genetic variants associated with the SLC47A2 gene may include variants that are located in the exons of the gene as well as variants identified by the following rs IDs: rs12943590, and rs34834489. Specific intronic regions associated with the SLC47A2 gene may include the following nucleotide positions on chromosome 17: 19619898 through 19620364, and more specifically the following positions on chromosome 17: 19619898 through 19620098, and 19620164 through 19620364.

For example, specific genetic variants associated with the SLC6A2 gene may include variants that are located in the exons of the gene as well as variants identified by the following rs IDs: rs3785143, and rs12708954. Specific intronic regions associated with the SLC6A2 gene may include the following nucleotide positions on chromosome 16: 55695006 through 55731699, and more specifically the following positions on chromosome 16: 55695006 through 55695206, and 55731499 through 55731699.

For example, specific genetic variants associated with the SLCO1B1 gene may include variants that are located in the exons of the gene as well as variants identified by the following rs IDs: rs2291073, rs4149036, rs77271279, rs4149032, rs11045821, rs11045872, rs4363657, rs4149081, rs11045879, and rs4149015. Specific intronic regions associated with the SLCO1B1 gene may include the following nucleotide positions on chromosome 12: 21325714 through 21283422, and more specifically the following positions on chromosome 12: 21325714 through 21325914, 21327640 through 21327840, 21329732 through 21329932, 21317691 through 21317891, 21332323 through 21332523, 21372244 through 21372444, 21368622 through 21368822, 21377921 through 21378121, 21382519 through 21382719, and 21283222 through 21283422.

For example, specific genetic variants associated with the TCF7L2 gene may include variants that are located in the exons of the gene as well as variants identified by the following rs IDs: rs7917983, rs4132670, rs4506565, rs7903146, rs12243326, rs12255372, rs290487, and rs1056877. Specific intronic regions associated with the TCF7L2 gene may include the following nucleotide positions on chromosome 10: 114732782 through 114925858 and more specifically the following positions on chromosome 10: 114732782 through 114732982, 114767671 through 114767871, 114755941 through 114756141, 114758249 through 114758449, 114788715 through 114788915, 114808802 through 114809002, 114909631 through 114909831, and 114925658 through 114925858.

For example, specific genetic variants associated with the TPMT gene may include variants that are located in the exons of the gene as well as variants identified by the following rs IDs: rs9333570, rs1800584, rs12201199, rs3931660, rs2518463, and rs12529220. Specific intronic regions associated with the TPMT gene may include the following nucleotide positions on chromosome 6: 18134021 through 18148347 and more specifically the following positions on chromosome 6: 18134021 through 18134221, 18130912 through 18131112, 18139702 through 18139902, 18149005 through 18149205, 18143669 through 18143869, and 18148147 through 18148347.

For example, specific genetic variants associated with the TYMS gene may include variants that are located in the exons of the gene as well as variants identified by the following rs IDs: rs2847153, and rs151264360. Specific intronic regions associated with the TYMS gene may include the following nucleotide positions on chromosome 18: 661547 through 673544, and more specifically the following positions on chromosome 18: 661547 through 661747, and 673344 through 673544.

For example, specific genetic variants associated with the UGT1A9 gene may include variants that are located in the exons of the gene as well as variants identified by the following rs IDs: rs2741048, rs2741047, rs4663871, rs4261716, rs7586110, rs3732218, rs3732219, rs1983023, rs45507691, rs3806596, rs3806597, rs2008595, rs10929302, rs2003569, rs60469444, rs34531096, rs76063448, rs4124874, rs3755319, r511568318, rs11568316, rs1976391, rs4148327, rs873478, rs3213726, rs2302538, rs887829, rs34650714, rs8175347, rs10929303, rs1042640, rs8330, and rs34942353. Additional specific genetic variants associated with the UGT1A9 gene may include genetic variants at the following genomic positions: Chr2:234581625, Chr2:234656479, Chr2:234675628, and Chr2:234675608.

Specific intronic regions associated with the UGT1A9 gene may include the following nucleotide positions on chromosome 2: 234581648 through 234681724, and more specifically the following positions on chromosome 2: 234581648 through 234581848, 234581554 through 234581754, 234581487 through 234581687, 234581525 through 234581725, 234593017 through 234593217, 234590427 through 234590627, 234627204 through 234627404, 234627148 through 234627348, 234636922 through 234637122, 234637120 through 234637320, 234637607 through 234637807, 234637469 through 234637669, 234637092 through 234637292, 234665682 through 234665882, 234667837 through 234668037, 234652540 through 234652740, 234665491 through 234665691, 234656379 through 234656579, 234652542 through 234652742, 234665559 through 234665759, 234667482 through 234667682, 234665398 through 234665598, 234665437 through 234665637, 234665883 through 234666083, 234675726 through 234675926, 234675528 through 234675728, 234668770 through 234668970, 234675423 through 234675623, 234675508 through 234675708, 234676313 through 234676513, 234668470 through 234668670, 234675729 through 234675929, 234668781 through 234668981, 234681316 through 234681516, 234681444 through 234681644, 234681545 through 234681745, and 234681524 through 234681724.

For example, specific genetic variants associated with the UGT1A1 gene may include variants that are located in the exons of the gene as well as variants identified by the following rs IDs: rs4148323, rs4148327, rs3213726, rs2302538, rs34650714, rs10929303, rs1042640, rs8330, and rs34942353. Additional specific genetic variants associated with the UGT1A1 gene may include genetic variants at the following genomic positions: Chr2:234675628, and Chr2:234675608. Specific UGT1A1 alleles may include the following UGT1A1 star alleles: *82, and *83.

Specific intronic regions associated with the UGT1A1 gene may include the following nucleotide positions on chromosome 2: 234669044 through 234681724, and more specifically the following positions on chromosome 2: 234669044 through 234669244, 234675726 through 234675926, 234675528 through 234675728, 234675423 through 234675623, 234675508 through 234675708, 234676313 through 234676513, 234675729 through 234675929, 234681316 through 234681516, 234681444 through 234681644, 234681545 through 234681745, and 234681524 through 234681724.

For example, specific genetic variants associated with the LIMPS gene may include variants that are located in the exons of the gene as well as variants identified by the following rs IDs: rs3772810. Specific intronic regions associated with the LIMPS gene may include the following nucleotide positions on chromosome 3: 124462859 through 124463059.

For example, specific genetic variants associated with the VKORC1 gene may include variants that are located in the exons of the gene as well as variants identified by the following rs IDs: rs17886199, rs17884982, rs17884850, rs8050894, rs17708472, rs104894542, rs2359612, rs2884737, rs9934438, rs11540137, rs7294, rs7200749, rs13336384, rs13337470, rs72547528, and rs9923231. Specific intronic regions associated with the VKORC1 gene may include the following nucleotide positions on chromosome 16: 31104347 through 31107789, and more specifically the following positions on chromosome 16: 31104347 through 31104547, 31103445 through 31103645, 31104302 through 31104502, 31104409 through 31104609, 31105253 through 31105453, 31102464 through 31102664, 31103696 through 31103896, 31105454 through 31105654, 31104778 through 31104978, 31102224 through 31102424, 31102221 through 31102421, 31102489 through 31102689, 31105071 through 31105271, 31105292 through 31105492, 31102555 through 31102755, and 31107589 through 31107789.

The design of the panel for detecting the above gene and variant lists may be based upon published research information, FDA approved therapies, and/or independent analysis of the pharmacogenomic effects of certain variants and/or alleles in drug treatments of any nature (such that the nature of treatment may not be limited to only one field or disease state because the pharmacogenomic effects may persist through differing fields of medicine). Current methods for genetic sequencing can rely on techniques used to isolate certain regions of interest of a genome, such as a genome of interest or a portion of the genome to be analyzed. In one embodiment, the regions of interest may be isolated using one or more specific probes, which bind to complementary sections of DNA/RNA in a sample. This detection is made possible by probes which are in the manufactured panel. A probe is a small stretch of DNA or RNA which serves as a starting point for DNA synthesis and allows the detection of a nucleic acid sequence that is complementary to the sequence of the probe. Probes hybridize (bind) with the complementary nucleotides of the template DNA or the target DNA and amplify DNA to make millions of copies of the DNA molecule. Each probe may be a single stranded DNA and is designed to match a specific piece of template DNA. The specificity arises from the fact that each DNA base can only pair with one other DNA base: that is, adenine (A) pairs only with thymine (T) in DNA and uracil (U) in RNA, and guanine (G) pairs only with cytosine (C). In order for copies to be made, the probe binds to the right piece of DNA and the bases match. If the matching occurs, then DNA polymerase (the enzyme that copies the DNA) can bind and amplify the DNA. If the probe does not match the DNA sequence, then the DNA polymerase does not bind and no copies are made. To get exactly the right order of A, G, T and C, a panel can be designed and ordered to include probes that contain the desired sequence of nucleotides.

Probes may be selected to target each of the identified genes and/or variants, and if a panel of probes is not sufficient to target each of the identified genes or variants, one or more spike-in probes that target additional genes and/or variants may be added to the panel to supplement the detection capability of the panel. A spike-in is a targeted probe which may be added to a probe panel to target additional genes or variants for detection during sequencing.

Panel design is an iterative process where a base panel is selected, spike-ins are identified that supplement the panel to allow the detection of additional target genes and/or variants, probes are manufactured according to the panel and added spike-ins, differing concentrations of the probes are optimally selected during titration testing by using differing quantities of each probe to identify the quantity that generates the most reliable detection for each variant, genetic sequencing runs are processed over test sample(s) with known sequences to verify accuracy of the panel, and the result obtained by the panel is compared with the known sequences to confirm that the panel is optimized to detect the intended target genes and variants.

Furthermore, some NGS panels may only include probes for detecting the exon region (coding region) of DNA or RNA. It may be advantageous to expand a base panel to generate sequencing results for the intron regions to identify other biomarkers within the human genome for both research and pharmacogenomic analysis. Spike-ins may be added to a panel to target at least one intron region to cure this deficiency.

FIG. 10 shows another embodiment of a patient report 1000. Specifically, FIG. 10 shows a molecular results portion of the patient report 1000 associated with a patient. The molecular result portion can include a pharmacogenomics results portion including a list of genes 1004, a portion of which include metabolic genes, and a list of phenotypes 1008 of the list of genes 1004. The list of phenotypes 1008 can include poor metabolizer, intermediate metabolizer, normal metabolizer, extensive metabolizer, ultrarapid metabolizer, increased sensitivity, and/or increased risk phenotypes based on molecular data associated with the patient. Genes 1004 may be displayed due to their involvement with metabolism, pharmacodynamic, and/or immunogenicity of selected medications.

Referring now to FIG. 10 as well as FIG. 11, the patient report 1000 can include a classifications portion 1012 including information about different classifications (e.g., gene-drug classifications) that can be included in the report. In some embodiments, the classifications can include standard administrations, dosing considerations, additional risks to consider, and/or contraindications.

The patient report 1000 can also include information about one or more drug types. In some embodiments, the drug types can include antidepressants, antipsychotics, anticonvulsants, anxiolytics, mood stabilizers, antimanics, hypnotics, VMAT2 inhibitors, ADHS medications, and/or other drug types that do not fall into one of the previous categories. Within each drug type, the patient report 1000 may further organize drugs by a drug subtype. As shown, a number of selective serotonin reuptake inhibitors (SSRIs) 1016 can be included in an antidepressant portion 1020 included in the patient report 1000.

The patient report 1000 can order drugs by classification type. Drugs with a single drug classification can be shown first within each drug type and/or subtype. For example, the SSRIs 1016 can include a drug 1024 classified as standard administration. As shown, Vilazodone is classified as standard administration for the patient. The drug 1024 (e.g., Vilazodone) can be listed along with a gene and/or a phenotype 1028 associated with the drug (e.g., CYP3A4 and/or normal metabolizer) and/or a link 1032 (e.g., a hyperlink) to a source document and/or website having information about the drug classification.

For a drugs with conflicting evidence 1036 (e.g., e.g., Citalopram), each drug classification can be listed along with along with a gene and/or a phenotype 1040 associated with the drug (e.g., CYP2C19 and/or normal metabolizer) and/or a link 1044 (e.g., a hyperlink) to a source document and/or website having information about the drug classification.

In some embodiments, for any drugs associated with an "increased risk phenotype," the patient report 1000 can include supplemental information 1048 about the increased risk and/or one or more links 1052 (e.g., a hyperlink) to a source document and/or website having information about the increased risk.

Referring now to FIGS. 10-11 as well as FIG. 12 and FIG. 13, the patient report 1000 can include a number of SNRIs 1056 can be included in the antidepressant portion 1020. Referring now to FIGS. 10-13 as well as FIG. 14, the patient report 1000 can include an antipsychotics portion 1060. Referring now to FIGS. 10-14 as well as FIG. 15, the patient report 1000 can include an anticonvulsants portion 1064. Referring now to FIGS. 10-15 as well as FIG. 16, the patient report 1000 can include an anxiolytics portion 1068 and/or a mood stabilizers portion 1072. Referring now to FIGS. 10-16 as well as FIG. 17, the patient report 1000 can include an antimanics portion 1076, a hypnotics portion 1080, a VMAT2 inhibitors portion 1084, and/or an ADHD medications portion 1088. Referring now to FIGS. 10-17 as well as FIG. 18, the patient report 1000 can include an other medications portion 1092.

Figure 19:
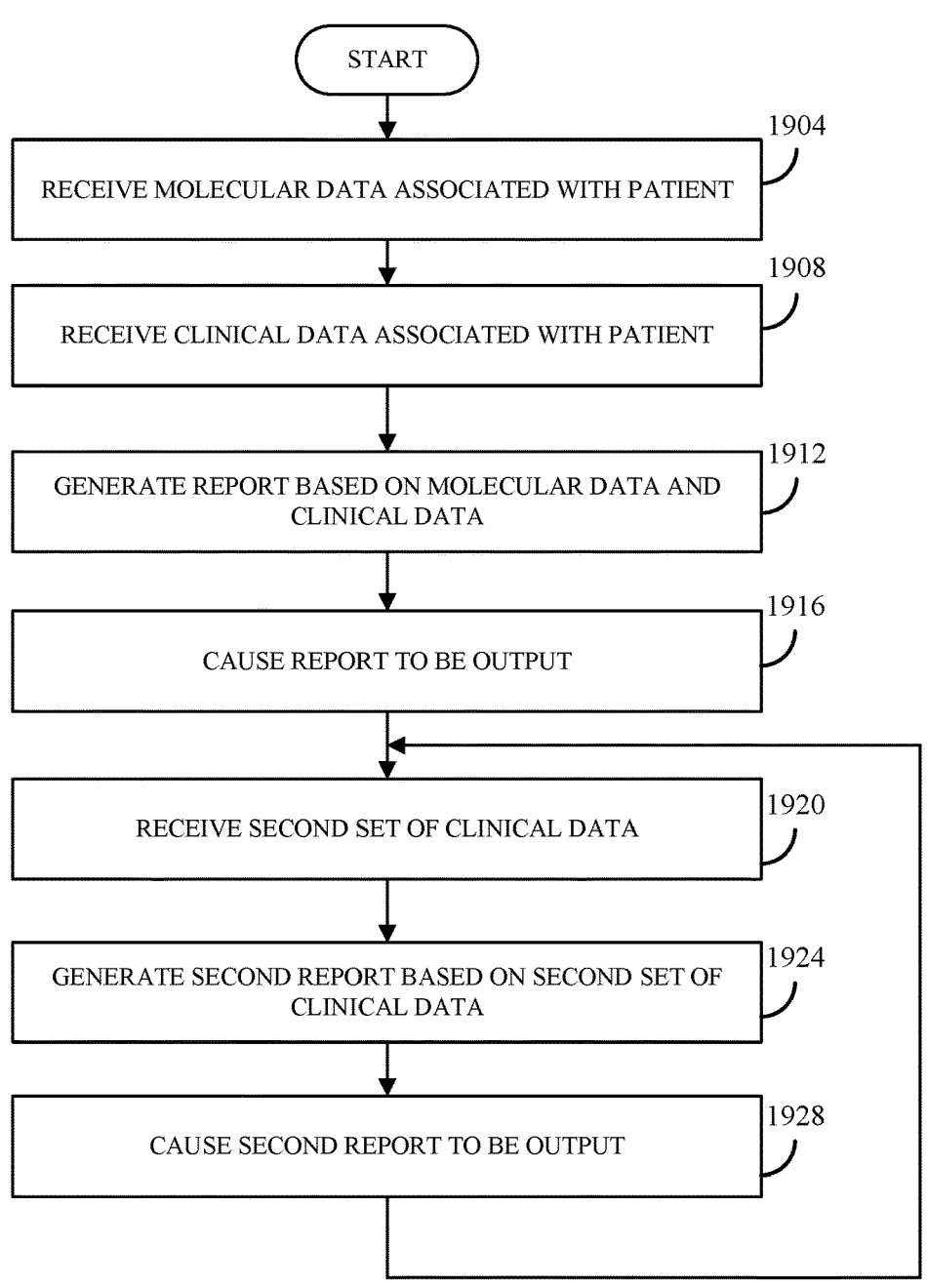
FIG. 19 is an exemplary process for generating treatment information for a patient diagnosed with a psychiatric illness.

Referring now to FIG. 19, an exemplary process 1900 for generating treatment information for a patient diagnosed with a psychiatric illness is shown. In some embodiments, process 1900 can be stored in a non-transitory computer-readable medium. In some embodiments, the process 1900 can be stored as executable instructions in a non-transitory computer-readable medium (e.g., at least one memory) and executed by at least one processor coupled to the computer-readable medium. In some embodiments, the process 1900 can be implemented in the system 10 in FIG. 1.

At 1904, the process 1900 can receive molecular data associated with a patient. In some embodiments, the patient can be diagnoses with at least one psychiatric illness (e.g., depression) as described above. In some embodiments, the molecular data can include a plurality of nucleic acid sequences. At least a portion of the plurality of nucleic acid sequence can be associated with a metabolic gene. In some embodiments, the molecular data can be generated based on a multi-gene panel sequencing reaction upon a sample from the patient. In some embodiments, the molecular data can include a plurality of nucleic acid sequences obtained from whole exome sequence data, mass array data, sequence data from one or more introns associated with metabolic genes, and/or sequence data from one or more promoter regions associated with the metabolic genes.

In some embodiments, at 1904, the process 1900 can align the molecular data to a human reference sequence. In some embodiments, the process 1900 can receive raw molecular data (e.g., stored in BCL, FASTA, and/or FASTQ file formats) and align the raw molecular data to the human reference sequence. In some embodiments, the process 1900 can generate aligned molecular data and store the data in SAM and/or BAM file formats. In some embodiments, the process 1900 can receive molecular data including pre-aligned molecular data.

At 1908, the process 1900 can receive clinical data associated with the patient. The clinical data can include a listing of prior medications the patient has taken and/or a listing of one or more diagnoses. The listing of prior medications can include one or more medication names, medication dosages, and/or patient responses to the medications. The one or more diagnoses can include a most recent set of diagnoses and/or a list of previous diagnoses the patient has had in the past. In some embodiments, the clinical activity described in the second set of clinical data comprises one or more of medication prescribed, dosage of medication, patient compliance, and patient outcome after having taken the prescribed medication.

At 1912, the process 1900 can generate a report based on the molecular data and the clinical data associated with the patient. The process 1900 can generate the report using a therapy engine. The therapy engine can include a knowledge database such as the KDB 40 described above. The knowledge database can include structured data regarding drug-gene interactions, including pharmacogenetic interactions, and precision medicine findings reported in the psychiatric and basic science literature. The knowledge database may include clinically annotated pharmacogenomic classifications for key pharmacodynamic and pharmacokinetic results related to the treatment of depression and other psychiatric diseases. The knowledge database of therapeutic and prognostic evidence, which includes therapeutic response and resistance information, may include information from a combination of external sources, which may include sources such as CPIC guidelines, FDA labeling, PharmGKB, or other proprietary databases that are either public or available by subscription or upon request, as well as literature sources or novel findings from analyzing a repository of clinical and genetic, genomic, or other-omic information. The knowledge database may be maintained over time by individuals with experience, education, and training in the relevant field. In some embodiments, clinical actionability entries in the knowledge database are structured by both (1) the disease and/or the drug-gene interaction to which the evidence applies and (2) the level or strength of evidence.

The knowledge database can include data related to interactions between a specific drug or drugs and one or more nucleic acid sequences associated with drug metabolism, primary drug metabolic pathway data, a cohort data set previously derived from a cohort of psychiatric subjects, the cohort data set including drug or drugs used in a treatment, diagnosis before the treatment and/or treatment outcome for patients in the cohort. In some embodiments, the cohort data is not derived from clinical trial data. In some embodiments, the cohort can include patients that were diagnosed with more than one psychiatric illness. In some embodiments, the knowledge database can include a second cohort data set derived time different than a first cohort set. The second cohort data set can include information from at least one patient in a previously generated cohort. In some embodiments, the knowledge database can include private cohorts updated using treatment outcome information from a number of patients. The knowledge database can store a portion of the clinical data and the second set of clinical data from at least a portion of the patients. Clinical data may, for example, be de-identified, stored in the form of a limited data set, be anonymized, or be pseudoanonymised.

The therapy engine can identify relevant drug-gene interactions based on the molecular data and the clinical data. More specifically, in some embodiments, the process 1900 can identify relevant drug-gene interactions based on at least a portion of the nucleic acid sequences included in the molecular data. In some embodiments, the therapy engine can identify resources related to including phenotypes included in the molecular data and one or more of the psychiatric diseases the patient has been diagnosed with. For example, the therapy engine can match a document about a study on patients having the same diagnoses and phenotype as the patient to the patient. A drug given to patients in the study can also be matched to the patient. In some embodiments, the knowledge database can include a number of drug-gene pairs, each drug-gene pair including a drug and a phenotype and associated with a disease. The process 1900 can search for drug-gene pairs in the knowledge database having the same phenotype as the patient and associated with the same psychiatric illness as the patient.

In some embodiments, the process 1900 can aggregate a list of all the drugs included in the drug gene pairs. The list of drugs can be associated with at least a portion of the nucleic acid sequences included in the molecular data. Each drug in the list of drugs can be associated with a classification. As described above, classifications can include standard administration, dose adjustment and/or dosing consideration, contraindication, and/or additional risks to consider. The classification can be predetermined based on the outcome of a study associated with the drug-gene interaction the drug is included in. For example, a study may determine that drug X is effective for illness Y in patients with phenotype Z, and the drug can be classified as standard administration. Some studies may provide information on the most effective does given other factors such as other diagnoses and/or patient information. The therapy engine can determine what the recommended dosage is based on the clinical data associated with the patient.

In some embodiments, the classifications can be generated based on the listing of prior medications. In some embodiments, the therapy engine can determine if certain drugs are more effective and/or pose risks to the patient based on what medications the patient has taken, what dosages were used, and/or what the outcome of the prior treatments were. Certain studies may be associated with specific cohorts of patients that certain drugs have been ineffective for treating a given psychiatric illness and/or to whom certain drugs pose a potential risk (e.g., of side effects).

Certain drugs may be classified as "contraindicative" due to conflicting evidence. For example, the therapy engine may find a first source that recommends drug X for phenotype Y of a first gene, while another source recommends drug X not be used to treat phenotype Z of the first gene and/or another gene. The therapy engine can output source documents and/or links to source documents for any source relevant to the patient. In particular, sources used to support a drug-gene interaction and/or a classification can be included in the report.

In some embodiments, the therapy engine can output a likely side effect of at least one drug included in the list of drugs. In some embodiments, the patient can be diagnosed with depression, and the therapy engine can determine a sub-type of depression the patient has. In some embodiments, the therapy engine can identify a drug resistance associated with the patient based on the molecular data and/or the clinical data.

In some embodiments, the process 1900 can determine the list of drugs based on the listing of prior medications the patient has received. In some embodiments, the therapy engine can identify studies for alternative drugs to take after other drugs have been proved ineffective on certain patients, such as patients with certain phenotypes.

In some embodiments, the therapy engine can generate the list of drugs based on longitudinal data associated with a cohort of patient similar to the patient. The cohort can be generated as described above. Using longitudinal information to generate the list of drugs can help in diagnosing the patient based on what drugs or drug doses have been proven to work on similar patients in the past. For example, a cohort of patients with one or more of the same phenotypes as the patient can be created. The therapy engine can then determine what drugs may be effective for the patient based on what drugs were effective for the cohort. For example the therapy engine can determine that when drug X was not effective for Y phenotype patients, Z drug was effective 80% of the time in the cohort. Thus, the cohort may be able to provide real-world information on diagnosing patients that is not available in a public clinical document and/or study. It is appreciated that the cohort can be created based on phenotype(s) and/or other factors such as genotype; therapies, geographical location, poverty level, gender, insurance status, and/or a combination of factors.

The process 1900 can generate the report based on any of the information received from the therapy engine, such as drug-gene interactions, drug classifications, dosage amounts, potential side effects, sub-type of depression, source documents, links to source documents (e.g., a hyperlink to a website or source document), and/or other suitable information, as well as molecular information and/or clinical information associated with the patient, such as phenotypes, and/or medication history. In some embodiments, the report can include at least a portion of the patient report 1000 in FIGS. 10-18.

At 1916, the process 1900 can cause the report to be output. In some embodiments, the process 1900 can cause the report to be output to at least one of a display (e.g., display device 16 in FIG. 1) or a memory. In some embodiments, the process 1900 can cause the report to be presented to a user (e.g., using the display device 16). In some embodiments, the user can be a medical practitioner treating the patient. In some embodiments, the process 1900 may then end.

At 1920, the process 1900 can receive a second set of clinical data associated with the patient. The second set of clinical data a listing of prior medications the patient has taken and/or a listing of one or more diagnoses. Importantly, the second set of clinical data can include the clinical data received at 1908 along with updated information associated with the patient. Specifically, the second set of clinical data can include clinical activity of the patient subsequent to presentation of the report. In some embodiments, the second set of clinical data can include one or more of medication prescribed; dosage of medication; patient compliance; and patient outcome after having taken the prescribed medication. The second set of clinical data can help in treating the patient with another medication and/or dosage. The one or more diagnoses can include a most recent set of diagnoses and/or a list of previous diagnoses the patient has had in the past. In some embodiments, the clinical activity described in the second set of clinical data can include one or more of medication prescribed, dosage of medication, patient compliance, and patient outcome after having taken the prescribed medication. In some embodiments, at 1920, the process 1900 can update the therapy engine, including the knowledge database, based on the second set of clinical data.

At 1924, the process 1900 can generate a second report based on the second set of clinical data. The process 1900 may generate the second report in a similar fashion as the report generated at 1912, albeit with updated clinical information for the patient, which can aid in finding an effective treatment plan for the patient. In some embodiments, the process 1900 can execute at least a portion of 1912 at 1924.

At 1928, the process 1900 can cause the second report to be output. In some embodiments, the process 1900 can cause the second report to be output to at least one of a display (e.g., display device 16 in FIG. 1) or a memory. In some embodiments, the process 1900 can cause the second report to be presented to a user (e.g., using the display device 16). In some embodiments, the user can be a medical practitioner treating the patient. In some embodiments, the process 1900 may then end. In some embodiments, the process 1900 may proceed to 1920.

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

We claim:

1. A method for generating treatment information for a patient diagnosed with at least one mental health disorder, the method comprising: at a computer system having one or more processors, and memory storing one or more programs for execution by the one or more processors:

a. obtaining molecular data from a multi-gene panel sequencing reaction performed upon a sample from the patient, the molecular data comprising a plurality of nucleic acid sequences, the nucleic acid sequences comprising sequence data from one or more introns, and sequence data from one or more promoter regions;

b. providing:

(1) a first set of clinical data associated with the patient, the first set of clinical data comprising a listing of prior medications and a listing of the one or more diagnoses; and (2) a first cohort data set, wherein the first cohort data set comprises data from a first cohort of subjects which have been diagnosed with at least one mental health disorder in common with the patient;

c. generating a first report from a therapy engine based on the molecular data, the first set of clinical data, and the first cohort data set, the therapy engine comprising one or more machine learning algorithms (MLAs), and a knowledge database, wherein the therapy engine uses the knowledge database to identify a target gene and determines an importance score of the target gene based on a plurality of metrics;

wherein the report provides:

(1) a listing of nucleic acid sequences that are associated with the diagnosed mental health disorder of the first cohort and that are identified in the molecular data from the patient;

(2) a list of one or more drugs that may be effective for the patient based on the listing of nucleic acids, and the data in the first cohort data set, and the identified target gene and importance score; and d. causing the report to be presented to a user wherein the therapy engine comprises a classifier to identify a drug resistance and wherein the drug resistance is listed on the report.

2. The method of claim 1, further comprising:

e. obtaining a second set of clinical data associated with the patient, wherein the second set of clinical data describes clinical activity of the patient subsequent to presentation of the report; and f. updating the therapy engine with at least a portion of the second set of clinical data.

3. The method of claim 1, wherein the one or more introns and one or more promoters are associated with metabolic genes.

4. The method of claim 1, wherein the patient is diagnosed with more than one mental health disorder.

5. The method of claim 1, wherein the knowledge database comprises:

i. data related to interactions between a specific drug or drugs and one or more nucleic acid sequences associated with drug metabolism;

ii. primary drug metabolic pathway data;

iii. a first cohort data set derived at time 1 from a cohort of subjects, the first cohort data set comprising: drug or drugs used in a treatment, diagnosis before the treatment, treatment outcome; and iv. drug information data collected from one or more of the following sources: scientific publications; scientific publications; a combination of external sources and/or other proprietary databases or information sources that are either public or available by subscription or upon request; literature sources or novel findings from analyzing a repository of clinical and genetic, genomic, or other-omic information.

6. The method of claim 5, wherein at least a portion of the subjects in the cohort were diagnosed with more than one mental health disorder.

7. The method of claim 5, wherein the knowledge database further comprises a second cohort data set derived at a time 2, wherein the second cohort data set comprises information from at least one of the first cohort subjects.

8. The method of claim 7, wherein the knowledge database further comprises an Nth cohort data set derived at time N, wherein the Nth cohort data set comprises information from at least one of the previous cohort subjects.

9. The method of claim 1, wherein the report further provides supporting information for a drug classification, wherein the drug classification is selected from the list comprising: standard administrations, dosing considerations, additional risks to consider, and contraindications.

10. The method of claim 1, wherein the report further provides a listing of drugs associated with the patient diagnosis but which have no known nucleic acid sequence associations.

11. The method of claim 1, wherein the listing of prior medications comprises at least one medication dosage.

12. The method of claim 1, wherein the listing of prior medications comprises at least one patient response to a medication.

13. The method of claim 1, wherein the therapy engine identifies a likely side effect of the drug(s) listed and provides that side effect information on the report.

14. The method of claim 1, wherein the therapy engine identifies a recommended dosage of each drug included in the listing of one or more drugs, and provides that dosage information on the report.

15. The method of claim 1, wherein the therapy engine identifies a next potential drug recommendation by excluding from the report at least one medication included in the listing of prior medications.

16. The method of claim 1, wherein the therapy engine comprises a classifier to identify a sub-type of depression and the mental health disorder the patient is diagnosed with is depression, wherein the sub-type of depression is listed on the report.

17. The method of claim 1, wherein the plurality of metrics comprises at least one of a gene/therapy metric, a gene/drug metric, or a correlation strength metric.

18. A system for generating information about treatment for a patient diagnosed with a mental health disorder, the system comprising:

a. at least one memory; and b. at least one processor coupled to the at least one memory, the system configured to cause the at least en one processor to execute instructions stored in the at least one memory to:

i. obtain molecular data from a multi-gene panel sequencing reaction performed upon a sample from the patient, the molecular data comprising a plurality of nucleic acid sequences, the nucleic acid sequences comprising sequence data from one or more introns, and sequence data from one or more promoter regions;

ii. provide;

(1) a first set of clinical data associated with the patient, the first set of clinical data comprising a listing of prior medications and a listing of the one or more diagnoses; and (2) a first cohort data set, wherein the first cohort data set comprises data from a first cohort of subjects which have been diagnosed with at least one mental health disorder in common with the patient;

iii. generate a first report from a therapy engine based on the molecular data, the therapy engine comprising one or more machine learning algorithms (MLAs), the first set of clinical data, and the first cohort data set, and a knowledge database, wherein the therapy engine uses the knowledge database to identify a target gene and determines an importance score of the target gene based on a plurality of metrics, and wherein the report provides: (1) a listing of nucleic acid sequences that are associated with the diagnosed mental health disorder of the first cohort; (2) a list of one or more drugs that may be effective for the patient based on the listing of nucleic acids and the data in the first cohort data set, and the identified target gene and importance score;

iv. cause the report to be presented to a user wherein the therapy engine comprises a classifier to identify a drug resistance and wherein the drug resistance is listed on the report.

19. A non-transitory computer readable medium having stored thereon program code instructions that, when executed by a processor, cause the processor to:

i. obtain molecular data from a multi-gene panel sequencing reaction performed upon a sample from the patient, the molecular data comprising a plurality of nucleic acid sequences, the nucleic acid sequences comprising sequence data from one or more introns, and sequence data from one or more promoter regions;

ii. provide (1) a first set of clinical data associated with the patient, the first set of clinical data comprising a listing of prior medications and a listing of the one or more diagnoses; and (2) a first cohort data set, wherein the first cohort data set comprises data from a first cohort of subjects which have been diagnosed with at least one mental health disorder in common with the patient;

iii. generate a first report from a therapy engine based on the molecular data, the first set of clinical data, and the first cohort data set, the therapy engine comprising one or more machine learning algorithms (MLAs) and a knowledge database, wherein the therapy ending uses the knowledge database to identify a target gene and determines an importance score of the target gene based on a plurality of metrics, and wherein the report provides: (1) a listing of nucleic acid sequences that are associated with the diagnosed mental health disorder of the first cohort; (2) a list of one or more drugs that may be effective for the patient based on the listing of nucleic acids, the data in the first cohort data set, and the identified target gene and importance score;

iv. cause the report to be presented to a user wherein the therapy engine comprises a classifier to identify a drug resistance and wherein the drug resistance is listed on the report.

* * * * *